United States Patent
Dow

(12) 
(10) Patent No.: US 6,657,063 B1
(45) Date of Patent: Dec. 2, 2003

(54) COMBINATIONS OF $\beta_3$ AGONISTS AND GROWTH HORMONE SECRETAGOGUES

(75) Inventor: Robert L. Dow, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/649,622

(22) Filed: Aug. 28, 2000

Related U.S. Application Data

(62) Division of application No. 09/290,985, filed on Apr. 13, 1999, now abandoned.
(60) Provisional application No. 60/083,650, filed on Apr. 30, 1998.
(51) Int. Cl.[7] .............................................. C07D 213/00
(52) U.S. Cl. ........................ 546/264; 546/193; 514/312; 514/313; 514/318; 514/330; 514/331
(58) Field of Search ................................ 514/330, 312, 514/313, 318, 331; 546/193, 264

(56) References Cited

U.S. PATENT DOCUMENTS 5,672,596 A * 9/1997 Wyvratt et al. ............. 514/183

FOREIGN PATENT DOCUMENTS

| WO | WO 96/35671 | * 11/1996 |
| WO | WO 97/24369 | * 7/1997 |

* cited by examiner

*Primary Examiner*—Christopher S. F. Low
*Assistant Examiner*—David Lukton
(74) *Attorney, Agent, or Firm*—Peter C. Richardson; Gregg C. Benson; Martha A. Gammill

(57) ABSTRACT

This invention is directed to pharmaceutical compositions comprising $\beta_3$ adrenergic agonists including (4-(2-(2-(6-aminopyridin-3-yl)-2(R)-hydroxyethylamino)ethoxy) phenyl)acetic acid and growth hormone or growth hormone secretagogues, prodrugs thereof or pharmaceutically acceptable salts of said compounds or said prodrugs. The invention is also directed to methods of using those compositions in the treatment of obesity, diabetes, hypertension and frailty in animals and particularly in humans.

5 Claims, No Drawings

# US 6,657,063 B1

COMBINATIONS OF β₃ AGONISTS AND GROWTH HORMONE SECRETAGOGUES

CROSS-REFERENCE TO RELATED APPLICATIONS

This application is a divisional of U.S. patent application Ser. No. 09/290,985, filed Apr. 13, 1999 now abandoned, which claims benefit of U.S. Provisional Patent application No. 60/083,650, filed Apr. 30, 1998.

BACKGROUND OF THE INVENTION

This invention relates to pharmaceutical compositions comprising β₃ adrenergic agonists including (4-(2-(2-(6-aminopyridin-3-yl)-2(R)-hydroxyethylamino)ethoxy) phenyl)acetic acid and growth hormone or growth hormone secretagogues, prodrugs thereof or pharmaceutically acceptable salts of said compounds or said prodrugs. These compositions have utility, inter alia, in the treatment of obesity, diabetes, hypertension and frailty in animals and particularly in humans. Accordingly, this invention also relates to methods of using such compositions for the treatment of obesity, diabetes, hypertension and frailty in animals, particularly humans.

Compounds of the Formula I

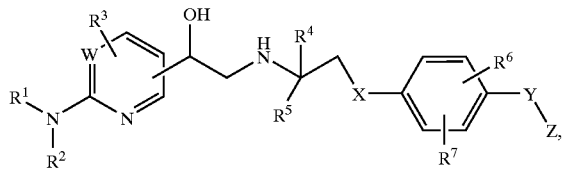

are disclosed in commonly assigned International Patent Application Numbers WO 96/35671 and WO96/35670, each designating, inter alia, the United States, as β₃ adrenergic agonists having utility in treating obesity, the disclosure of which is incorporated herein by reference. The various substituents of the compound of Formula I are as defined in those patent applications. Within the scope of that disclosure is 4-(2-(2-(6-aminopyridin-3-yl)-2(R)-hydroxyethylamino) ethoxy)phenyl)acetic acid, the compound of Formula II,

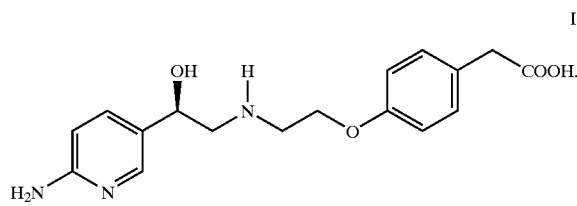

β-Adrenergic agents have been categorized into β₁, β₂, and β₃ subtypes. Agonists of β-receptors promote the activation of adenyl cyclase. Activation of β₁ receptors invokes increases in heart rate. Activation of β₂ receptors induces relaxation of smooth muscle tissue which produces a drop in blood pressure and the onset of skeletal muscle tremors. Activation of β₃ receptors is known to stimulate lipolysis, which is the breakdown of adipose tissue triglycerides to glycerol and fatty acids. Activation of β₃ receptors also stimulates the metabolic rate, thereby increasing energy expenditure. Accordingly, activation of β₃ receptors promotes the loss of fat mass. Compounds that stimulate β₃ receptors are therefore useful as anti-obesity agents.

International Patent Application Publication No. WO 97/16189, designating, inter alia, the United States, the disclosure of which is incorporated herein by reference, discloses the use of selective β₃ receptor agonists in combination with compounds which modify eating behavior for the treatment of obesity.

International Patent Application Publication Number WO 96/24369, designating, inter alia, the United States, which is incorporated herein by reference, discloses growth hormone secretagogues of the Formula III

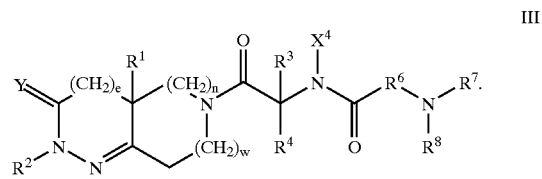

wherein the variables are as defined in WO96/24369.

Commonly assigned U.S. Provisional Application No. 60/050764, filed Jun. 25, 1997, which is incorporated herein by reference, discloses growth hormone secretagogues of the Formula IV

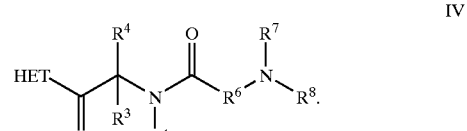

SUMMARY

This invention is directed to pharmaceutical compositions comprising a β₃ adrenergic agonist, a growth hormone secretagogue or growth hormone and a pharmaceutically acceptable carrier or diluent.

A group of preferred compositions, designated the A Group, are those pharmaceutical compositions as disclosed in the immediately preceding paragraph wherein said β₃ adrenergic agonist is a compound of the Formula I:

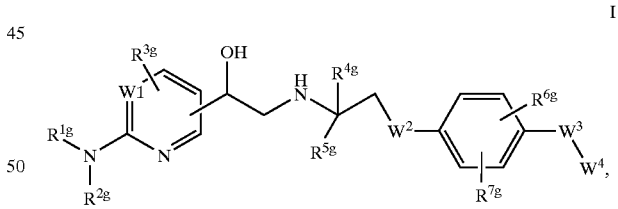

wherein:
$R^{1g}$, $R^{2g}$, $R^{4g}$, and $R^{5g}$ are independently hydrogen or $(C_1-C_6)$alkyl;
$R^{3g}$, $R^{6g}$ and $R^{7g}$ are independently hydrogen, halogen, $(C_1-C_6)$alkyl, nitro, cyano, trifluoromethyl, $SO_2R^{8g}$, $SO_2NR^{9g}R^{10g}$, $NR^{9g}R^{10g}$, $COR^{11g}$, $CO_2R^{9g}$, $(C_1-C_6)$ alkoxy, $NR^{9g}SO_2R^{8g}$, $NR^{9g}COR^{11g}$, $NR^{9g}CO_2R^{9g}$ or $OR^{9g}$;
$R^{8g}$ is independently $(C_1-C_6)$alkyl or $(C_1-C_6)$alkoxy $(C_1-C_6)$alkyl;
$R^{9g}$ and $R^{10g}$ are independently hydrogen, $(C_1-C_6)$alkyl, cycloalkyl$(C_3-C_8)$, or $(C_1-C_6)$alkoxy$(C_1-C_6)$alkyl;
$R^{11g}$ is independently hydrogen, $(C_1-C_6)$alkyl, $NR^{9g}R^{10g}$, $(C_3-C_8)$cycloalkyl, or $(C_1-C_6)$alkoxy$(C_1-C_6)$alkyl;

$W^1$ is N, CH, or, when $R^{3g}$ is bonded to $W^1$, $CR^{3g}$ wherein $R^{3g}$ can be any of the values listed above for $R^{3g}$ in addition to H;

$W^2$ and $W^3$ are independently a direct link, oxygen, sulfur, or $NR^{1g}$ wherein $R^{1g}$ is as defined above;

$W^4$ is $(CH_2)_yOR^{9g}$, $(CH_2)_zCO_2R^{11g}$, $(CH_2)_zCOR^{11g}$, $(CH_2)_zSO_2NR^{9g}R^{10g}$, $(CH_2)_z$—$NR^{9g}SO_2R^{8g}$, $(CH_2)_zP(O)(OR^{1g})(OR^{2g})$, $(CH_2)_z$—O—$(CH_2)_yCO_2R^{11g}$, $(CH_2)_n$—O—$(CH_2)_yCOR^{11g}$, $(CH_2)_z$—O—$(CH_2)_yP(O)(OR^{1g})(OR^{2g})$, $(CH_2)_z$—O—$(CH_2)_ySO_2NR^{9g}R^{10g}$, or $(CH_2)_z$—O—$(CH_2)_yNR^{9g}SO_2R^{8g}$ wherein $R^{1g}$, $R^{2g}$, $R^{8g}$, $R^{9g}$, $R^{10g}$, and $R^{11g}$ are as defined above;

y is 1 to 6;

z is 0 to 6, provided that if $W^3$ is O or S, z is not 0;

pharmaceutically acceptable prodrugs of said compounds; and pharmaceutically acceptable salts of said compounds and said prodrugs.

A group of compositions which is preferred within the A Group are those compositions, designated Group B, wherein said $\beta_3$ adrenergic agonist is (4-(2-(2-(6-aminopyridin-3-yl)-2(R)-hydroxyethylamino)ethoxy)phenyl)acetic acid, a prodrug thereof, or a pharmaceutically acceptable salt of said $\beta_3$ adrenergic agonist or said prodrug.

A more preferred group of compositions within the B Group are those compositions comprising growth hormone.

Another more preferred group of compositions within the B Group are those compositions comprising (N-(1(R)-((1,2-dihydro-1-methanesulfonyl-spiro(3H-indole-3,4'-piperidin)-1'-yl)carbonyl)-2-(phenylmethyloxy)ethyl)-2-amino-2-methylpropanamide.

Yet another more preferred group of compositions within the B Group are those compositions, designated Group C, wherein said growth hormone secretagogue is a compound of the Formula IV:

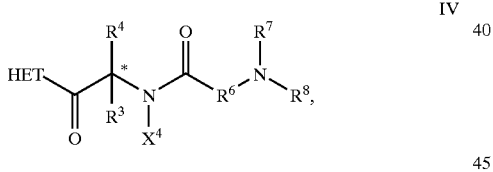

IV or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein HET is a heterocyclic moiety selected from the group consisting of

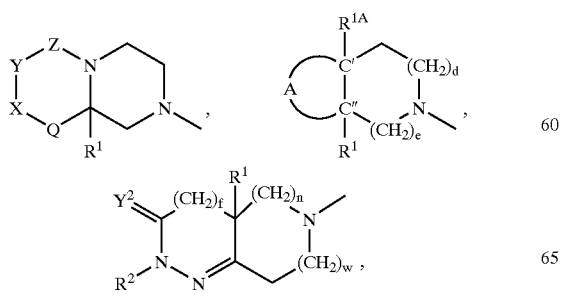

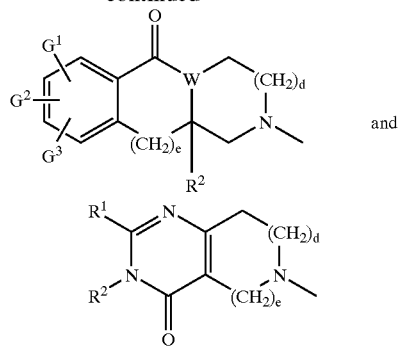

and d is 0, 1 or 2;
e is 1 or 2;
f is 0 or 1;
n and w are 0, 1 or 2, provided that n and w cannot both be 0 at the same time;
$Y^2$ is oxygen or sulfur;
A is a divalent radical, where the left hand side of the radical as shown below is connected to C″ and the right hand side of the radical as shown below is connected to C′, selected from the group consisting of —$NR^2$—C(O)—$NR^2$—, —$NR^2$—S(O)$_2$—$NR^2$—, —O—C(O)—$NR^2$—, —$NR^2$—C(O)—O—, —C(O)—$NR^2$C(O)—, —C(O)—$NR^2$—C($R^9R^{10}$)—, —C($R^9R^{10}$)—$NR^2$—C(O)—, —C($R^9R^{10}$)—C($R^9R^{10}$)—C($R^9R^{10}$)—, —S(O)$_2$—C($R^9R^{10}$)—C($R^9R^{10}$)—, —C($R^9R^{10}$)—O—C(O)—, —C($R^9R^{10}$)—O—C($R^9R^{10}$)—, —$NR^2$—C(O)—C($R^9R^{10}$)—, —O—C(O)—C($R^9R^{10}$)—, —C($R^9R^{10}$)—C(O)—$NR^2$—, —C(O)—$NR^2$—C(O)—, —C($R^9R^{10}$)—C(O)—O—, —C(O)—$NR^2$—C($R^9R^{10}$)—C($R^9R^{10}$)—, —C(O)—O—C($R^9R^{10}$)—, —C($R^9R^{10}$)—C($R^9R^{10}$)—C($R^9R^{10}$)—C($R^9R^{10}$)—, —S(O)$_2$—$NR^2$—C($R^9R^{10}$)—C($R^9R^{10}$)—, —C($R^9R^{10}$)—C($R^9R^{10}$)—$NR^2$—C(O)—, —C($R^9R^{10}$)—C($R^9R^{10}$)—O—C(O)—, —$NR^2$—C(O)—C($R^9R^{10}$)—C($R^9R^{10}$)—, —$NR^2$—S(O)$_2$—C($R^9R^{10}$)—C($R^9R^{10}$)—, —O—C(O)—C($R^9R^{10}$)—C($R^9R^{10}$)—, —C($R^9R^{10}$)—C($R^9R^{10}$)—C(O)—$NR^2$—, —C($R^9R^{10}$)—C($R^9R^{10}$)—C(O)—, —C($R^9R^{10}$)—$NR^2$—C(O)—O—, —C($R^9R^{10}$)—O—C(O)—$NR^2$, —C($R^9R^{10}$)—$NR^2$—C(O)—$NR^2$—, —$NR^2$—C(O)—O—C($R^9R^{10}$)—, —$NR^2$—C(O)—$NR^2$—C($R^9R^{10}$)—, —$NR^2$—S(O)$_2$—$NR^2$—C($R^9R^{10}$)—, —S(O)$_2$—$NR^2$—C($R^9R^{10}$)—, —O—C(O)—$NR^2$—C($R^9R^{10}$)—, —C(O)—N=C($R^{11}$)—$NR^2$—, —C(O)—$NR^2$—C($R^{11}$)=N—, —C($R^9R^{10}$)—$NR^{12}$—C($R^9R^{10}$)—, —$NR^{12}$—C($R^9R^{10}$)—, —$NR^{12}$—C($R^9R^{10}$)—C($R^9R^{10}$)—, —C(O)—O—C($R^9R^{10}$)—C($R^9R^{10}$)—, —$NR^2$—C($R^{11}$)=N—C(O)—, —C($R^9R^{10}$)—C($R^9R^{10}$)—N($R^{12}$)—, —C($R^9R^{10}$)—$NR^{12}$—, —N=C($R^{11}$)—$NR^2$—C(O)—, —C($R^9R^{10}$)—C($R^9R^{10}$)—$NR^2$—S(O)$_2$—, —C($R^9R^{10}$)—C($R^9R^{10}$)—S(O)$_2$—$NR^2$—, —C($R^9R^{10}$)—C($R^9R^{10}$)—C(O)—O—, —C($R^9R^{10}$)—S(O)$_2$—C($R^9R^{10}$)—, —C($R^9R^{10}$)—C($R^9R^{10}$)—S(O)$_2$—, —O—C($R^9R^{10}$)—C($R^9R^{10}$)—, —C($R^9R^{10}$)—C($R^9R^{10}$)—O—, —C($R^9R^{10}$)—C(O)—C($R^9R^{10}$)—, —C(O)—C($R^9R^{10}$)—C($R^9R^{10}$)— and —C($R^9R^{10}$)—$NR^2$—S(O)$_2$—$NR^2$—;

Q is a covalent bond or $CH_2$;
W is CH or N;
X is $CR^9R^{10}$, $C=CH_2$ or $C=O$;
Y is $CR^9R^{10}$, O or $NR^2$;
Z is $C=O$, $C=S$ or $S(O)_2$;
$G^1$ is hydrogen, halo, hydroxy, nitro, amino, cyano, phenyl, carboxyl, $-CONH_2$, $-(C_1-C_4)$alkyl optionally independently substituted with one or more phenyl, one or more halogens or one or more hydroxy groups, $-(C_1-C_4)$alkoxy optionally independently substituted with one or more phenyl, one or more halogens or one or more hydroxy groups, $-(C_1-C_4)$alkylthio, phenoxy, $-COO(C_1-C_4)$alkyl, N,N-di-$(C_1-C_4)$alkylamino, $-(C_2-C_6)$alkenyl optionally independently substituted with one or more phenyl, one or more halogens or one or more hydroxy groups, $-(C_2-C_6)$alkynyl optionally independently substituted with one or more phenyl, one or more halogens or one or more hydroxy groups, $-(C_3-C_6)$cycloalkyl optionally independently substituted with one or more $(C_1-C_4)$alkyl groups, one or more halogens or one or more hydroxy groups, $-(C_1-C_4)$alkylamino carbonyl or di-$(C_1-C_4)$alkylamino carbonyl;
$G^2$ and $G^3$ are each independently selected from the group consisting of hydrogen, halo, hydroxy, $-(C_1-C_4)$alkyl optionally independently substituted with one to three halo groups and $-(C_1-C_4)$alkoxy optionally independently substituted with one to three halo groups;
$R^1$ is hydrogen, $-CN$, $-(CH_2)_qN(X^6)C(O)X^6$, $-(CH_2)_qN(X^6)C(O)(CH_2)_t-A^1$, $-(CH_2)_qN(X^6)S(O)_2(CH_2)_t-A^1$, $-(CH_2)_qN(X^6)S(O)_2X^6$, $-(CH_2)_q N(X^{6)C(O)N(X6)}(CH_2)_t-A^1$, $-(CH_2)_qN(X^6)C(O)N(X^6)(X^6)$, $-(CH_2)_qC(O)N(X^6)(X^6)$, $-(CH_2)_qC(O)N(X^6)(CH_2)_t-A^1$, $-(CH_2)_qC(O)OX^6$, $-(CH_2)_qC(O)O(CH_2)_t-A^1$, $-(CH_2)_qOX^6$, $-(CH_2)_qOC(O)X^6$, $-(CH_2)_qOC(O)(CH_2)_t-A^1$, $-(CH_2)_qOC(O)N(X^6)(CH_2)_t-A^1$, $-(CH_2)_qOC(O)N(X^6)(X^6)$, $-(CH_2)_qC(O)X^6$, $-(CH_2)_qC(O)(CH_2)_t-A^1$, $-(CH_2)_qN(X^6)C(O)OX^6$, $-(CH_2)_qN(X^6)S(O)_2N(X^6)(X^6)$, $-(CH_2)_qS(O)_mX^6$, $-(CH_2)_qS(O)_m(CH_2)_t-A^1$, $-(C_1-C_{10})$alkyl, $-(CH_2)_t-A^1$, $-(CH_2)_q-(C_3-C_7)$cycloalkyl, $-(CH_2)_q-Y^1-(C_1-C_6)$alkyl, $-(CH_2)_q-Y^1-(CH_2)_t-A^1$ or $-(CH_2)_q-Y^1-(CH_2)_t-(C_3-C_7)$cycloalkyl;
where the alkyl and cycloalkyl groups in the definition of $R^1$ are optionally substituted with $(C_1-C_4)$ alkyl, hydroxy, $(C_1-C_4)$alkoxy, carboxyl, $-CONH_2$, $-S(O)_m(C_1-C_6)$alkyl, $-CO_2(C_1-C_4)$ alkyl ester, 1H-tetrazol-5-yl or 1, 2 or 3 fluoro groups;
$Y^1$ is O, $S(O)_m$, $-C(O)NX^6-$, $-CH=CH-$, $-C\equiv C-$, $-N(X^6)C(O)-$, $-C(O)NX^6-$, $-C(O)O-$, $-OC(O)N(X^6)-$ or $-OC(O)-$;
q is 0, 1, 2, 3 or 4;
t is 0, 1, 2 or 3;
said $-(CH_2)_q$ group and $-(CH_2)_t$ group in the definition of $R^1$ are optionally independently substituted with hydroxy, $(C_1-C_4)$alkoxy, carboxyl, $-CONH_2$, $-S(O)_m(C_1-C_6)$alkyl, $-CO_2(C_1-C_4)$ alkyl ester, 1H-tetrazol-5-yl, 1, 2 or 3 fluoro groups or 1 or 2 $(C_1-C_4)$alkyl groups;
$R^{1A}$ is selected from the group consisting of hydrogen, F, Cl, Br, I, $(C_1-C_6)$alkyl, phenyl$(C_1-C_3)$alkyl, pyridyl$(C_1-C_3)$alkyl, thiazolyl$(C_1-C_3)$alkyl and thienyl$(C_1-C_3)$alkyl, provided that $R^{1A}$ is not F, Cl, Br or I when a heteroatom is vicinal to C";

$R^2$ is hydrogen, $(C_1-C_8)$alkyl, $-(C_0-C_3)$alkyl-$(C_3-C_8)$ cycloalkyl, $-(C_1-C_4)$alkyl-$A^1$ or $A^1$;
where the alkyl groups and the cycloalkyl groups in the definition of $R^2$ are optionally substituted with hydroxy, $-C(O)OX^6$, $-C(O)N(X^6)(X^6)$, $-N(X^6)(X^6)$, $-S(O)_m(C_1-C_6)$alkyl, $-C(O)A^1$, $-C(O)(X^6)$, $CF_3$, CN or 1, 2 or 3 independently selected halo groups;
$R^3$ is selected from the group consisting of $A^1$, $(C_1-C_{10})$alkyl, $-(C_1-C_6)$alkyl-$A^1$, $-(C_1-C_6)$alkyl-$(C_3-C_7)$cycloalkyl, $-(C_1-C_5)$alkyl-$X^1-(C_1-C_5)$ alkyl, $-(C_1-C_5)$alkyl-$X^1-(C_0-C_5)$alkyl-$A^1$ and $-(C_1-C_5)$alkyl-$X^1-(C_1-C_5)$alkyl-$(C_3-C_7)$ cycloalkyl;
where the alkyl groups in the definition of $R^3$ are optionally substituted with $-S(O)_m(C_1-C_6)$alkyl, $-C(O)OX^3$, 1, 2, 3, 4 or 5 independently selected halo groups or 1, 2 or 3 independently selected $-OX^3$ groups;
$X^1$ is O, $S(O)_m$, $-N(X^2)C(O)-$, $-C(O)N(X^2)-$, $-OC(O)-$, $-C(O)O-$, $-CX^2=CX^2-$, $-N(X^2)C(O)O-$, $-OC(O)N(X^2)-$ or $-C\equiv C-$;
$R^4$ is hydrogen, $(C_1-C_6)$alkyl or $(C_3-C_7)$cycloalkyl, or $R^4$ is taken together with $R^3$ and the carbon atom to which they are attached and form $(C_5-C_7)$cycloalkyl, $(C_5-C_7)$cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;
$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;
$R^6$ is a bond or is

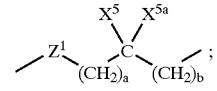

where a and b are each independently 0, 1, 2 or 3;
$X^5$ and $X^{5a}$ are each independently selected from the group consisting of hydrogen, $CF_3$, $A^1$ and optionally substituted $(C_1-C_6)$alkyl;
the optionally substituted $(C_1-C_6)$alkyl in the definition of $X^5$ and $X^{5a}$ is optionally substituted with a substituent selected from the group consisting of $A^1$, $OX^2$, $-S(O)_m(C_1-C_6)$ alkyl, $-C(O)OX^2$, $(C_3-C_7)$cycloalkyl, $-N(X^2)(X^2)$ and $-C(O)N(X^2)(X^2)$;
or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then only one of $X^5$ or $X^{5a}$ is on the carbon atom and only one of $R^7$ or $R^8$ is on the nitrogen atom and further provided that when two alkylene bridges are formed then $X^5$ and $X^{5a}$ cannot be on the carbon atom and $R^7$ and $R^8$ cannot be on the nitrogen atom;
or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;

or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$Z^1$ is a bond, O or $N-X^2$, provided that when a and b are both 0 then $Z^1$ is not $N-X^2$ or O;

$R^7$ and $R^8$ are each independently hydrogen or optionally substituted $(C_1-C_6)$alkyl;

where the optionally substituted $(C_1-C_6)$alkyl in the definition of $R^7$ and $R^8$ is optionally independently substituted with $A^1$, $-C(O)O-(C_1-C_6)$alkyl, $-S(O)_m(C_1-C_6)$alkyl, 1 to 5 halo groups, 1 to 3 hydroxy groups, 1 to 3 $-O-C(O)(C_1-C_{10})$alkyl groups or 1 to 3 $(C_1-C_6)$alkoxy groups; or $R^7$ and $R^8$ can be taken together to form $-(CH_2)_r-L-(CH_2)_r-$;

where L is $C(X^2)(X^2)$, $S(O)_m$ or $N(X^2)$;

$R^9$ and $R^{10}$ are each independently selected from the group consisting of hydrogen, fluoro, hydroxy and $(C_1-C_5)$alkyl optionally independently substituted with 1–5 halo groups;

$R^{11}$ is selected from the group consisting of $(C_1-C_5)$alkyl and phenyl optionally substituted with 1–3 substitutents each independently selected from the group consisting of $(C_1-C_5)$alkyl, halo and $(C_1-C_5)$alkoxy;

$R^{12}$ is selected from the group consisting of $(C_1-C_5)$ alkylsulfonyl, $(C_1-C_5)$alkanoyl and $(C_1-C_5)$alkyl where the alkyl portion is optionally independently substituted by 1–5 halo groups;

$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, on one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, $-OX^6$, $-C(O)N(X^6)(X^6)$, $-C(O)OX^6$, oxo, $(C_1-C_6)$ alkyl, nitro, cyano, benzyl, $-S(O)_m(C_1-C_6)$alkyl, 1H-tetrazol-5-yl, phenyl, phenoxy, phenylalkyloxy, halophenyl, methylenedioxy, $-N(X^6)(X^6)$, $-N(X^6)C(O)(X^6)$, $-S(O)_2N(X^6)(X^6)$, $-N(X^6)S(O)_2$-phenyl, $-N(X^6)S(O)_2X^6$, $-CONX^{11}X^{12}$, $-S(O)_2NX^{11}X^{12}$, $-NX^6S(O)_2X^{12}$, $-NX^6CONX^{11}X^{12}$, $-NX^6S(O)_2NX^{11}X^{12}$, $-NX^6C(O)X^{12}$, imidazoyl, thiazolyl and tetrazolyl, provided that if $A^1$ is optionally substituted with methylenedioxy then it can only be substituted with one methylenedioxy;

where $X^{11}$ is hydrogen or optionally substituted $(C_1-C_6)$alkyl;

the optionally substituted $(C_1-C_6)$alkyl defined for $X^{11}$ is optionally independently substituted with phenyl, phenoxy, $(C_1-C_6)$alkoxycarbonyl, $-S(O)_m(C_1-C_6)$alkyl, 1 to 5 halo groups, 1 to 3 hydroxy groups, 1 to 3 $(C_1-C_{10})$alkanoyloxy groups or 1 to 3 $(C_1-C_6)$alkoxy groups;

$X^{12}$ is hydrogen, $(C_1-C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, $CH_3$, $OCH_3$, $OCF_3$ and $CF_3$;

or $X^{11}$ and $X^{12}$ are taken together to form $-(CH_2)_r-L^1-(CH_2)_r-$;

$L^1$ is $C(X^2)(X^2)$, O, $S(O)_m$ or $N(X^2)$;

r for each occurrence is independently 1, 2 or 3;

$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with $-S(O)_m(C_1-C_6)$alkyl, $-C(O)OX^3$, 1 to 5 halo groups or 1–3 $OX^3$ groups;

$X^3$ for each occurrence is independently hydrogen or $(C_1-C_6)$alkyl;

$X^6$ for each occurrence is independently hydrogen, optionally substituted $(C_1-C_7)$alkyl, $(C_2-C_6)$ halogenated alkyl, optionally substituted $(C_3-C_6)$ cycloalkyl, $(C_3-C_7)$-halogenated cycloalkyl, where optionally substituted $(C_1-C_6)$alkyl and optionally substituted $(C_3-C_7)$cycloalkyl in the definition of $X^6$ is optionally independently mono- or di-substituted with $(C_1-C_4)$alkyl, hydroxy, $(C_1-C_4)$alkoxy, carboxyl, $CONH_2$, $-S(O)_m(C_1-C_6)$alkyl, carboxylate $(C_1-C_4)$ alkyl ester or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$ as a ring member;

$X^7$ is hydrogen or $(C_1-C_6)$alkyl optionally substituted with hydroxy;

m for each occurrence is independently 0, 1 or 2.

A preferred group within the C Group are those compositions, designated Group D, wherein said growth hormone secretagogue is 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, a prodrug thereof or a pharmaceutically acceptable salt of said growth hormone secretagogue or said prodrug.

A more preferred group within the D Group are those compositions comprising (4-(2-(2-(6-aminopyridin-3-yl)-2 (R)-hydroxyethylamino)ethoxy)phenyl)acetic acid and 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, a prodrug of either entity or a pharmaceutically acceptable salt of either entity.

Another preferred group within the C Group are those compositions, designated Group E, wherein said growth hormone secretagogue is 2-amino-N-(1-(R)-(2,4-difluoro-benzyloxymethyl)-2-oxo-2-(3-oxo-3a-(R)-pyridin-2-yl)-2-(2,2,2-trifluoro-ethyl)-2,3,3a,4,6,7-hexahydro-pyrazolo-[4,3-c]pyridin-5-yl)-ethyl)-2-methylpropionamide, a prodrug thereof or a pharmaceutically acceptable salt of said growth hormone secretagogue or said prodrug.

A more preferred group within the E Group are those compositions comprising (4-(2-(2-(6-aminopyridin-3-yl))-2(R)-hydroxyethylamino)ethoxy)phenyl)acetic acid and 2-amino-N-(1-(R)-(2,4-difluorobenzyloxymethyl)-2-oxo-2-(3-oxo-3a-(R)-pyridin-2-yl)-2-(2,2,2-trifluoro-ethyl)-2,3,3a,4,6,7-hexahydro-pyrazolo-[4,3-c]pyridin-5-yl)-ethyl)-2-methyl-propionamide, a prodrug of either entity or a pharmaceutically acceptable salt of either entity.

Yet another preferred group within the C Group are those compositions, designated Group F, wherein said growth hormone secretagogue is 2-amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, a prodrug thereof or a pharmaceutically acceptable salt of said growth hormone secretagogue or said prodrug.

A more preferred group within the F Group are those compositions comprising (4-(2-(2-(6-aminopyridin-3-yl))-2(R)-hydroxyethylamino)ethoxy)phenyl)acetic acid and 2-amino-N-{(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, a prodrug of either entity or a pharmaceutically acceptable salt of either entity.

This invention is also directed to methods for treating diabetes, obesity, hyperglycemia, frailty associated with obesity or frailty associated with aging or for enhancing the quality of sleep in a mammal comprising administering to said mammal in need of such treatment a therapeutically effective amount of a $\beta_3$ adrenergic agonist and a growth hormone secretagogue or growth hormone.

In the methods set forth in the preceding paragraph, an especially preferred method, designated Method A, is wherein said $\beta_3$ adrenergic agonist is a compound of formula I above, a prodrug thereof or a pharmaceutically acceptable salt of said compound or said prodrug.

A preferred method within Method A, designated Method B, is wherein said $\beta_3$ adrenergic agonist is (4-(2-(2-(6-aminopyridin-3-yl))-2(R)-hydroxyethylamino)ethoxy)phenyl)acetic acid, a prodrug thereof or a pharmaceutically acceptable salt of said $\beta_3$ adrenergic agonist or said prodrug.

A preferred method within Method B, designated Method C, comprises growth hormone.

A preferred method within Method C comprises treating diabetes in a mammal.

Another preferred method within Method C comprises treating hyperglycemia in a mammal.

Another preferred method within Method C comprises treating obesity in a mammal.

Another preferred method within Method C comprises treating frailty associated with obesity in a mammal.

Another preferred method within Method C comprises treating frailty associated with aging in a mammal.

Another preferred method within Method C comprises enhancing the quality of sleep of a mammal.

A preferred method within Method B, designated Method D, is wherein said growth hormone secretagogue is a compound of Formula IV above, a prodrug thereof or a pharmaceutically acceptable salt of said compound or said prodrug.

A preferred method within Method D, designated Method E, is wherein said growth hormone secretagogue is 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, a prodrug thereof or a pharmaceutically acceptable salt of said growth hormone secretagogue or said prodrug.

A preferred method within Method E comprises treating diabetes in a mammal.

Another preferred method within Method E comprises treating hyperglycemia in a mammal.

Another preferred method within Method E comprises treating obesity in a mammal.

Another preferred method within Method E comprises treating frailty associated with obesity in a mammal.

Another preferred method within Method E comprises treating frailty associated with aging in a mammal.

Another preferred method within Method E comprises enhancing the quality of sleep of a mammal.

Yet another preferred method within Method D, designated Method F, is wherein said growth hormone secretagogue is 2-amino-N-(1-(R)-(2,4-difluoro-benzyloxymethyl)-2-oxo-2-(3-oxo-3a-(R)-pyridin-2-yl)-2-(2,2,2-trifluoro-ethyl)-2,3,3a,4,6,7-hexahydro-pyrazolo-[4,3-c]pyridin-5-yl)-ethyl)-2-methyl-propionamide, a prodrug thereof or a pharmaceutically acceptable salt of said growth hormone secretagogue or said prodrug.

A preferred method within Method F comprises treating diabetes in a mammal.

Another preferred method within Method F comprises treating hyperglycemia in a mammal.

Another preferred method within Method F comprises treating obesity in a mammal.

Another preferred method within Method F comprises treating frailty associated with obesity in a mammal.

Another preferred method within Method F comprises treating frailty associated with aging in a mammal.

Another preferred method within Method F comprises enhancing the quality of sleep of a mammal.

Yet another preferred method within Method D, designated Method G, is wherein said growth hormone secretagogue is 2-amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, a prodrug thereof or a pharmaceutically acceptable salt of said growth hormone secretagogue or said prodrug.

A preferred method within Method G comprises treating diabetes in a mammal.

Another preferred method within Method G comprises treating hyperglycemia in a mammal.

Another preferred method within Method G comprises treating obesity in a mammal.

Another preferred method within Method G comprises treating frailty associated with obesity in a mammal.

Another preferred method within Method G comprises treating frailty associated with aging in a mammal.

Another preferred method within Method G comprises enhancing the quality of sleep of a mammal.

This invention is also directed to methods of increasing the content of lean meat in edible animals comprising administering to an edible animal an amount of a $\beta_3$ adrenergic agonist and a growth hormone secretagogue or growth hormone.

In the methods set forth in the immediately preceding paragraph, a preferred method, designated Method H, is wherein said $\beta_3$ adrenergic agonist is a compound of Formula I above, a prodrug thereof or a pharmaceutically acceptable salt of said compound or said prodrug.

A preferred method within Method H, designated Method I, is wherein said $\beta_3$ adrenergic agonist is (4-(2-(2-(6-aminopyridin-3-yl)-2(R)-hydroxyethylamino)ethoxy) phenyl)acetic acid, a prodrug thereof or a pharmaceutically acceptable salt of said $\beta_3$ adrenergic agonist or said prodrug.

A preferred method within Method I comprises growth hormone.

Another preferred method within Method I, designated Method J, is wherein said growth hormone secretagogue is a compound of Formula IV above, a prodrug thereof or a pharmaceutically acceptable salt of said compound or said prodrug.

A preferred method within Method J is wherein said growth hormone secretagogue is 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, a prodrug thereof or a pharmaceutically acceptable salt of said growth hormone secretagogue or said prodrug.

Another preferred method within Method J is wherein said growth hormone secretagogue is 2-amino-N-(1-(R)-(2,4-difluoro-benzyloxymethyl)-2-oxo-2-(3-oxo-3a-(R)-pyridin-2-yl)-2-(2,2,2-trifluoro-ethyl)-2,3,3a,4,6,7-hexahydro-pyrazolo-[4,3-c]pyridin-5-yl)-ethyl)-2-methyl-propionamide, a prodrug thereof or a pharmaceutically acceptable salt of said compound or said prodrug.

Another preferred method within Method J is wherein said growth hormone secretagogue is 2-amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, a prodrug thereof or a pharmaceutically acceptable salt of said compound or said prodrug.

This invention is also directed to kits comprising:
a. an amount of a $\beta_3$ adrenergic agonist, a prodrug thereof or a pharmaceutically acceptable salt of said $\beta_3$ adrenergic agonist or said prodrug in a first unit dosage form;
b. an amount of a growth hormone secretagogue or growth hormone, a prodrug thereof or a pharmaceutically acceptable salt of said growth hormone secretagogue or said prodrug in a second unit dosage form; and
c. a container.

In the kits set forth in the immediately preceding paragraph, a preferred kit, designated Kit A, is wherein said $\beta_3$ adrenergic agonist is a compound of Formula I above, a prodrug thereof or a pharmaceutically acceptable salt of said compound or said prodrug.

A preferred kit within Kit A, designated Kit B, is wherein said $\beta_3$ adrenergic agonist is (4-(2-(2-(6-aminopyridin-3-yl)-2(R)-hydroxyethylamino)ethoxy)phenyl)acetic acid, a prodrug thereof or a pharmaceutically acceptable salt of said $\beta_3$ adrenergic agonist or said prodrug.

A preferred kit within Kit B comprises growth hormone.

Another preferred kit within Kit B, designated Kit C, is wherein said growth hormone secretagogue is a compound of the Formula IV above, a prodrug thereof or a pharmaceutically acceptable salt of said growth hormone secretagogue or said prodrug.

A preferred kit within Kit C is wherein said growth hormone secretagogue is 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, a prodrug thereof or a pharmaceutically acceptable salt of said growth hormone secretagogue or said prodrug.

Another preferred kit within Kit C is wherein said growth hormone secretagogue is 2-amino-N-(1-(R)-(2,4-difluoro-benzyloxymethyl)-2-oxo-2-(3-oxo-3a-(R)-pyridin-2-yl)-2-(2,2,2-trifluoro-ethyl)-2,3,3a,4,6,7-hexahydro-pyrazolo-[4,3-c]pyridin-5-yl)-ethyl)-2-methyl-propionamide, a prodrug thereof or a pharmaceutically acceptable salt of said growth hormone secretagogue or said prodrug.

Another preferred kit within Kit C is wherein said growth hormone secretagogue is 2-amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, a prodrug thereof or a pharmaceutically acceptable salt of said growth hormone secretagogue or said prodrug.

This invention also relates to compositions, methods and kits for treating insulin resistant conditions such as Non-Insulin Dependent Diabetes Mellitus (NIDDM) and reduced glycemic control associated with obesity and aging in a mammal in need thereof which comprises administering to said mammal an effective amount of a $\beta_3$ adrenergic agonist, a prodrug thereof or a pharmaceutically acceptable salt of said $\beta_3$ adrenergic agonist or said prodrug and a growth hormone secretagogue, a prodrug thereof or a pharmaceutically acceptable salt of said growth hormone secretagogue or said prodrug. The compounds of Formula I are particularly preferred $\beta_3$ adrenergic agonists. The compounds of Formula IV are particularly preferred growth hormone secretagogues.

This invention also provides a method of using a composition comprising a $\beta_3$ adrenergic agonist and a growth hormone secretagogue or growth hormone to treat diabetes, obesity, hyperglycemia, frailty associated with obesity or frailty associated with aging or for enhancing the quality of sleep in a mammal comprising administering to said mammal in need of such treatment a therapeutically effective amount of said composition.

Included within the scope of the present invention is a method of using a combination of this invention, i.e., a $\beta_3$ adrenergic agonist and a growth hormone secretagogue or growth hormone, for enhancing and improving the quality of sleep. The combination is useful in enhancing or improving sleep quality as well as preventing and treating sleep disorders and disturbances in a mammal. In addition, the use of the combination of this invention increases sleep efficiency and augments sleep maintenance. The combination of this invention may further be used in a method for preventing and treating sleep disorders and sleep disturbances in a mammal. The present invention further provides a pharmaceutical composition for enhancing or improving sleep quality and increasing sleep efficiency and sleep maintenance.

The present method of using a combination of this invention further provides the following: an increase in the value which is calculated from the time that a subject sleeps divided by the time that a subject is attempting to sleep; a decrease in sleep latency, i.e., the time it takes to fall asleep; a decrease in difficulties in falling asleep; a decrease in the number of awakenings during sleep; a decrease in nocturnal arousals; a decrease in the time spent awake following the initial onset of sleep; an increase in the total amount of sleep; and increase in the amount and percentage of rapid eye movement (REM) sleep; an increase in the duration and occurrence of REM sleep; a reduction in the fragmentation of REM sleep; an increase in the amount and percentage of stage 2 sleep; an enhancement of EEG-delta activity during sleep; a decrease in the number of awakenings; a decrease in nocturnal arousals, especially early morning awakenings; an increase in daytime alertness; an increased satisfaction with the intensity of sleep; and increased sleep maintenance. Secondary outcomes which may be provided by the present invention include enhanced cognitive function and increased memory retention.

The present invention is further useful for the prevention of sleep disorders and sleep disturbances including: sleep problems associated with insomnia, hypersomnia, sleep apnea, narcolepsy, nocturnal dysomnias, night terror, insomnias associated with depression or with emotional/mood disorders, as well as sleep walking and enuresis, as well as sleep disorders which accompany aging, sleep disorders associated with obesity, conditions associated with circadian rhythmicity, mental and physical disorders associated with travel across time zones and with rotating shift-work schedules, or syndromes such as fibromyalgia which are manifested by non-restorative sleep and muscle pain or sleep apnea which is associated with respiratory disturbances during sleep.

The present invention has several advantagous veterinary features. For the pet owner or veterinarian who wishes to increase leanness and trim unwanted fat from pet animals, the present invention provides the means by which this can be accomplished. For poultry, cattle and swine raisers, using the method of the present invention yields leaner animals which command higher prices from the meat industry.

DETAILED DESCRIPTION OF THE INVENTION

The compounds of Formula I, including (4-(2-(2-(6-aminopyridin-3-yl)-2(R)-hydroxyethylamino)ethoxy) phenyl)acetic acid, which are used in the method and pharmaceutical compositions of the instant invention, are readily prepared according to methods well known to those skilled in the art particularly as described in International Patent Application Publication No. WO 96/35671. Specifically, the compounds of Formula I are prepared by reacting a carboxylic acid ester derivative or other protected carboxylic acid derivative of a compound of formula I with a base such as potassium hydroxide in an aqueous solvent such as ethanol/water, methanol/water or the like. The reaction mixture is stirred at a temperature of about 0° C. to about 25° C. until the reaction is complete as determined by thin layer chromatography or other analytical technique. Generally, the reaction mixture is stirred for four hours. The product is generally isolated by adjusting the pH of the reaction mixture to the isoelectric point of the compound of Formula I and filtering to obtain the solid product. When the carboxylic acid ester derivative used in this method is racemic, the product is the racemate of a compound of Formula I.

The compound of Formula II which is used in the methods and compositions of the instant invention is an optically active compound and is designated the 2(R) enantiomer. This enantiomer is prepared from the racemate according to resolution methods well known to those skilled in the art.

Alternatively, the compound of Formula II may be prepared from optically active intermediates as set forth below.

The compound of Formula II can be synthesized from compounds of Formula V

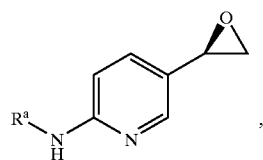

V wherein $R^a$ is a suitable amine protecting group, by a coupling reaction with an amine of Formula VI

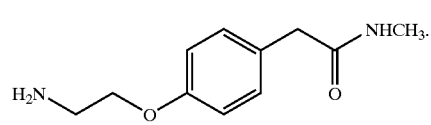

VI

This amine is prepared as set forth in Preparation Nine below or may be otherwise prepared according to methods well known to those skilled in the art. This coupling reaction is typically carried out by reacting said amine with an epoxide of Formula V in a polar aprotic solvent such as dimethyl sulfoxide, dimethyl formamide, acetonitrile or a lower alkanol such as ethanol, 2-propanol or butanol at a temperature from about −10° C. to about 125° C. Preferably, the solvent is dimethyl sulfoxide and the reaction is carried out at a temperature from about 0° C. to about 80° C.

The compounds of Formula V may be prepared by treating a compound of Formula VII

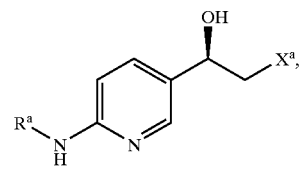

VII wherein $R^a$ is a suitable amine protecting group and $X^a$ is a suitable leaving group such as halo or organosulfonyloxy, with a non-nucleophilic base. Generally, it is preferred that the non-nucleophilic base be selected from the group consisting of sodium hydroxide, potassium hydroxide, sodium hydride, potassium tert-butoxide or 1,8-diazabicyclo[5.4.0]undec-7-ene. The reaction is preferably conducted by stirring the substrate compound of Formula VII together with the appropriate non-nucleophilic base in a reaction inert solvent at a temperature of about −20° C. to about 100° C. Where used herein, the term reaction inert solvent refers to any solvent or solvent system which does not interact with starting materials, reagents, intermediates or products in a manner which adversely affects the reaction or the yield of the desired product. With respect to this particular reaction, it is preferred that the solvent is a polar, non-hydroxylic solvent such as an ether derivative including but not limited to tetrahydrofuran, dioxane and dimethoxyethane; chlorinated hydrocarbons including but not limited to carbon tetrachloride, chloroform and methylene chloride; aromatic hydrocarbons including but not limited to benzene, toluene and xylene; dimethylformamide; dimethylsulfoxide or any mixture of these solvents. Generally the most preferred solvent is tetrahydrofuran.

When the compounds of Formula VII disclosed herein are organosulfonyloxy derivatives, said compounds may be prepared by reacting an appropriate compound of Formula VIII

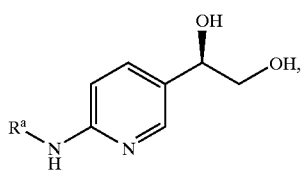

VIII wherein $R^a$ is a suitable amine protecting group, with an organosulfonyl chloride in the presence of a suitable base. Suitable bases which may be used to effect this transformation include the lower trialkylamines, pyridine and pyridine derivatives. Preferred bases within those groups include but are not limited to triethylamine, diisopropylethylamine, 2,4,6-collidine and 2,6-lutidine. Pyridine is the most preferred base. Suitable organosulfonyl chlorides include methanesulfonyl chloride, p-nitrobenzenesulfonyl chloride, m-nitrobenzenesulfonyl chloride, p-toluenesulfonyl chloride and benzenesulfonyl chloride. A generally preferred organosulfonyl chloride derivative is p-toluenesulfonyl chloride. The reaction is conveniently conducted by stirring the desired substrate compound of Formula VIII together with the appropriate organosulfonyl chloride in a reaction inert solvent at a temperature of about −20° C. to about 50° C. It is preferred that the solvent is a polar solvent such as an ether derivative including but not limited to tetrahydrofuran, dioxane and dimethoxyethane; chlorinated hydrocarbons including but not limited to carbon tetrachloride, chloroform and methylene chloride; aromatic hydrocarbons including but not limited to benzene, toluene and xylene; dimethylformamide; N-methyl-2-pyrrolidinone; dimethylacetamide; pyridine or any mixture of these solvents. Generally the most preferred solvent is pyridine. Due to the presence of chloride ion in this reaction, the reaction product may be contaminated with 2-chloro derivatives. These mixtures can be converted entirely to the 2-chloro derivatives as described below.

To prepare the compounds of Formula VII wherein X is halo, the 2-organosulfonyloxy derivatives of the compound of Formula VII or mixtures thereof containing 2-chloro derivatives of the compound of Formula VII are reacted with a halogenating agent in a reaction inert solvent. The reaction may be conducted conveniently at a temperature of from about 25° C. to the reflux temperature of the solvent utilized. It is generally preferred to conduct the reaction at the reflux temperature. Halogenating agents are compounds which are capable of transferring a halo group to an organic substrate, said substrate having a leaving group which can be displaced by said halide ion. Preferred halogenating agents are lithium halides. A particularly preferred chlorinating agent used to prepare the compounds of Formula VII wherein $X^a$ is chloro is lithium chloride. A preferred solvent is ethanol.

The compounds of Formula VIII disclosed herein may be prepared by reacting an appropriate compound of Formula IX

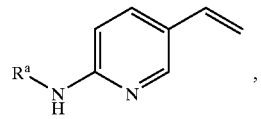

IX wherein $R^a$ is a suitable amine protecting group, with a catalyst comprised of osmium (VIII) oxide or an osmium salt, in the presence of an auxiliary oxidizing agent, and optionally in the presence of a chiral auxiliary ligand such as (DHQD)$_2$PHAL or (DHQD)$_2$PYR and an auxiliary base. When it is desirable to use a catalyst other than osmium (VIII) oxide in this reaction, the catalyst is generally selected from osmium metal, potassium osmate (VI) dihydrate and osmium (III) chloride. Generally, it is preferred to use osmium tetroxide as the catalyst when conducting this reaction. Auxiliary oxidizing agents that may be employed include but are not limited to potassium ferricyanide, sodium ferricyanide, potassium persulfate, sodium persulfate, potassium chlorate, sodium chlorate and N-methylmorpholine-N-oxide (the latter oxidizing agent may only be used in the absence of chiral auxiliary ligands such as (DHQD)$_2$PHAL or (DHQD)$_2$PYR). It may also be desirable to use a mixture of auxiliary oxidizing agents to achieve optimum performance in this reaction. An especially suitable mixture of auxiliary oxidizing agents is sodium persulfate and potassium ferricyanide. Chiral auxiliary ligands that may be used, in addition to those already recited, include hydroquinidine indolinediyl diether ((DHQD)IND), hydroquinine phthalazinediyl diether ((DHQ)$_2$PHAL), hydroquinine pyrimindinediyl diether ((DHQ)$_2$PYR), hydroquinine indolinediyl diether ((DHQ)IND), hydroquinidine phenanthrinediyl diether (DHQD-PHN) and hydroquinine phenanthrinediyl diether (DHQ-PHN). The reaction is typically conducted by stirring the desired substrate compound of Formula IX together with the appropriate reagents recited above in a polar solvent at a temperature of about −10° C. to about 70° C. The reaction is conveniently conducted at about 20° C. Polar solvents which are generally useful in this reaction include water, a lower alkanol, an ether or a mixture of any of these solvents. A lower alkanol is an alcohol containing from one to four carbon atoms.

The dihydroxylation reaction disclosed in the preceding paragraph may be conducted either in the presence or in the absence of a chiral auxiliary ligand. When the reaction is conducted in the absence of a chiral auxiliary ligand, the diol product is racemic. When the reaction is conducted in the presence of a chiral auxiliary ligand, the dihydroxylation reaction proceeds stereoselectively, resulting in an essentially optically pure diol product.

The compounds of Formula IX disclosed herein may be prepared by reacting a compound of Formula X

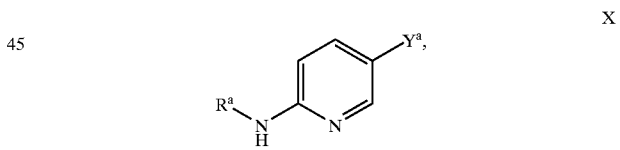

X wherein $R^a$ is a suitable amine protecting group and $Y^a$ is halo, with ethylene gas in the presence of a base, a phosphine derivative and a palladium catalyst. Suitable bases for the reaction include lower trialkylamines, sodium carbonate, potassium carbonate, sodium bicarbonate and potassium bicarbonate. Generally, triethylamine is preferred. Suitable phosphine derivatives include triarylphosphines such as triphenylphosphine, diphenyl-2-pyridylphosphine and tri-ortho-tolylphosphine, with the latter being generally preferred. When $Y^a$ is iodo, the palladium catalyst may be selected from a variety of palladium salts and complexes such as but not limited to palladium metal on carbon or some other suitable solid support, allylpalladium chloride dimer, palladium (II) chloride, palladium (II) acetate, palladium (0) tetrakis(triphenylphosphine), palladium (II) bis(triphenylphosphine) chloride, palladium (0) bis(dibenzylideneacetone) and palladium (0) bis(benzonitrile).

When $Y^a$ is bromo or trifluoromethanesulfonyloxy, the palladium catalyst may be selected from a variety of palladium salts and complexes such as but not limited to allylpalladium chloride dimer, palladium (II) chloride, palladium (II) acetate, palladium (0) tetrakis(triphenylphosphine), palladium (II) bis(triphenylphosphine) chloride, palladium (0) bis(dibenzylideneacetone), palladium (0) bis(benzonitrile and allylpalladium chloride dimer. Palladium (II) acetate is especially preferred. The reaction is typically conducted by stirring the compound of Formula VI together with the above recited reagents in a polar solvent at a temperature of about 20° C. to about 150° C. under an atmosphere of ethylene at a pressure of about 1 atmosphere to about 10 atmospheres. The preferred polar solvents for use in this reaction include, but are not limited to ethers, such as tetrahydrofuran, dimethoxyethane and dioxane; lower trialkylamines, such as triethylamine, diisopropylethylamine and tributylamine; aromatic hydrocarbons, such as benzene, toluene and xylene; dimethylformamide; N-methyl-2-pyrrolidone; acetonitrile; dimethylacetamide; or a mixture of any of these solvents. Acetonitrile is an especially preferred solvent.

The compounds of Formula VI above are prepared according to procedures well known to those skilled in the art or in a manner analogous to the procedures set forth in Preparations Six to Nine below.

The compounds of Formula X above are prepared from the commercially or otherwise readily available 2-amino-3-bromo-pyridine according to procedures well known to those skilled in the art or in a manner analogous to that set forth in Preparation One.

If not commercially available, the necessary starting materials for the chemical reactions disclosed herein may be prepared by procedures which may be selected from standard organic chemical techniques found in standard organic textbook references. The techniques found therein may be applied directly to the synthesis of known starting materials described directly in that reference or may be applied by analogy to compounds having similar functionality to achieve predictable results.

The second compound of this invention is a growth hormone secretagogue or growth hormone per se.

A representative first class of growth hormone secretagogues is set forth in PCT Application Publication No. WO97124369, which is incorporated herein by reference, as compounds having the structural Formula:

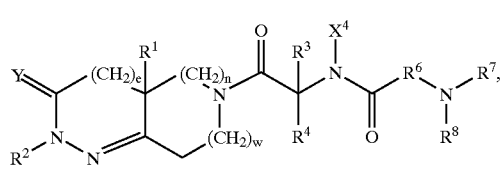

III wherein the various substituents are as defined in WO97/24369. Said compounds are prepared as disclosed therein.

2-Amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, having the following structure:

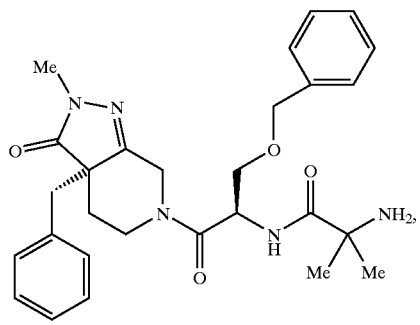

and 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c] pyridin-5-yl)-ethyl)-2-methyl-propionamide, having the following structure:

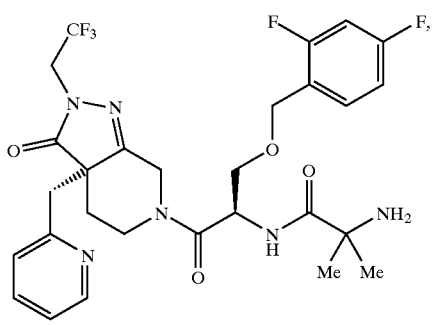

are both within the scope of the disclosure of International Patent Application Publication Number WO97/24369.

A representative second class of growth hormone secretagogues is set forth in U.S. Pat. No. 5,206,235, which is incorporated herein by reference, as having the following structure:

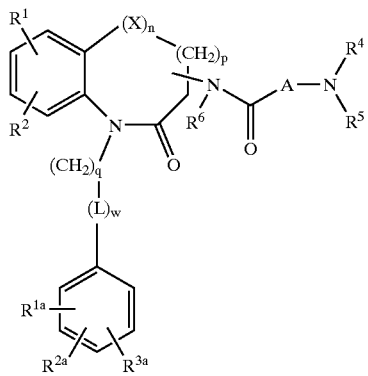

wherein the various substituents are as defined in U.S. Pat. No. 5,206,235. Said compounds are prepared as disclosed therein.

The most preferred compounds within this class are identified as having the following structures:

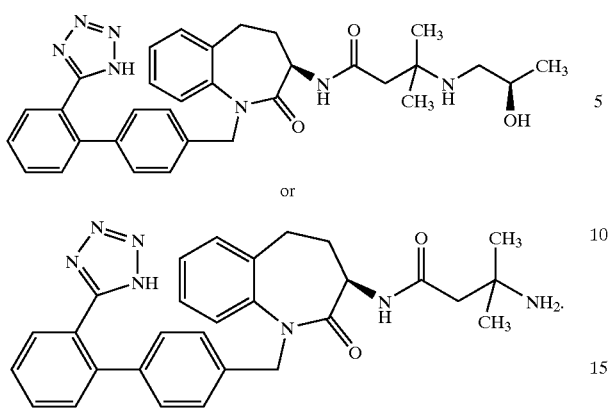
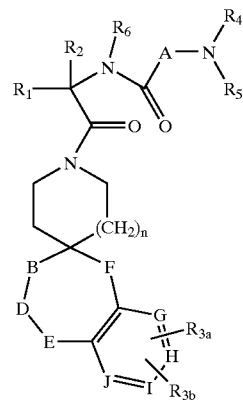

A representative third class of growth hormone secretagogues is set forth in U.S. Pat. No. 5,283,241, which is incorporated herein by reference, as having the following structural formula:

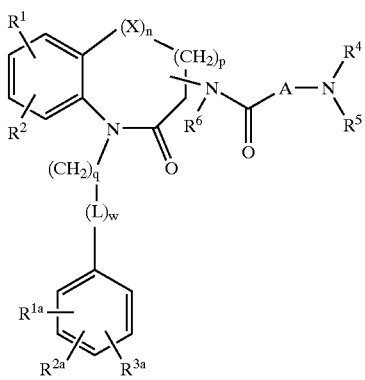

wherein the various substituents are as defined in U.S. Pat. No. 5,283,241. Said compounds are prepared as disclosed therein.

A representative fourth class of growth hormone secretagogues is disclosed in PCT Publication No. WO97/41879, designating, inter alia, the United States and which is incorporated herein by reference, as compounds having the following structural formulas:

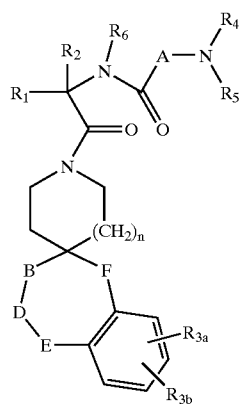

wherein the various substituents are as defined in WO97/41879. Said compounds are prepared as disclosed therein.

The most preferred compounds within this fourth class which may be employed in the present invention are identified as having the following structure:

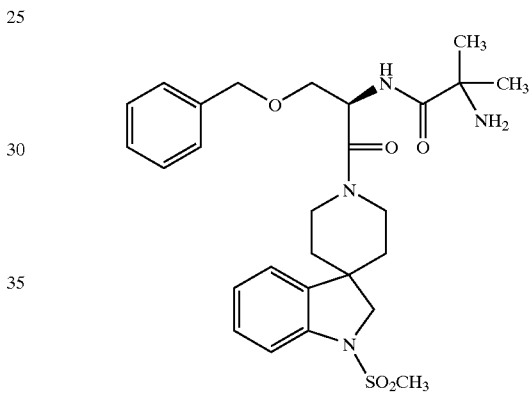

and pharmaceutically acceptable salts thereof, in particular, the methanesulfonate salt.

A representative fifth class of growth hormone secretagogues is disclosed in U.S. Pat. No. 5,492,916, which is incorporated herein by reference, as being compounds of the structural Formula I:

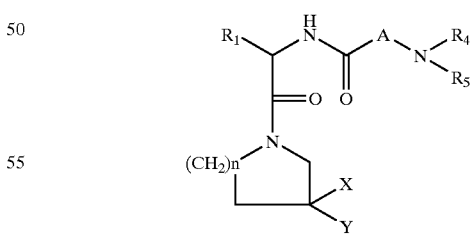

wherein the various substituents are as defined in U.S. Pat. No. 5,492,916. Said compounds are prepared disclosed therein.

A representative sixth class of growth hormone secretagogues is set forth in U.S. Provisional Application No. 60/050764, filed Jun. 25, 1997, having Pfizer docket number PC9598JDC, as compounds having the structural Formula:

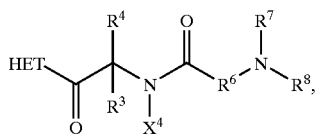

IV wherein the various substituents are as defined in said Provisional Application No. 60/050764. Said compounds are prepared as disclosed therein or as described herein.

The preparation of the compounds of Formula IV of the present invention can be carried out in sequential or convergent synthetic routes. Syntheses detailing the preparation of the compounds of Formula IV in a sequential manner are presented in the following reaction schemes.

Many protected amino acid derivatives are commercially available, where the protecting groups, Prt, Prt' or Prt", are, for example, BOC, CBZ, FMOC, benzyl or ethoxycarbonyl groups. Other protected amino acid derivatives can be prepared by literature methods well-known to one skilled in the art. Some substituted piperazines and piperidines are commercially available, and many other piperazines and 4-substituted piperidines are known in the literature. Various heterocyclic substituted piperidines and piperazines can be prepared following literature methods using derivatized heterocyclic intermediates. Alternatively, the heterocyclic rings of such compounds can be derivatized by standard means, such as coupling with CDI, hydrogenation of aromatic heterocycles, etc. as is well-known to those skilled in the art.

Many of the schemes illustrated below describe compounds which contain protecting groups Prt, Prt' or Prt", which can be any suitable protecting group known to those skilled in the art. Benzyloxycarbonyl groups can be removed by a number of methods including, catalytic hydrogenation with hydrogen in the presence of a palladium or platinum catalyst in a protic solvent such as methanol. Preferred catalysts are palladium hydroxide on carbon or palladium on carbon. Hydrogen pressures from 1–1000 psi can be employed; pressures from 10 to 70 psi are preferred. Alternatively, the benzyloxycarbonyl group can be removed by transfer hydrogenation.

Removal of BOC protecting groups can be carried out using a strong acid such as trifluoroacetic acid or hydrochloric acid with or without the presence of a cosolvent such as dichloromethane or methanol at a temperature of about −30° to 70° C., preferably about −5° to about 35° C.

Benzyl groups on amines can be removed by a number of methods including catalytic hydrogenation with hydrogen in the presence of a palladium catalyst in a protic solvent such as methanol. Hydrogen pressures from 1–1000 psi can be employed; pressures from 10 to 70 psi are preferred. The addition and removal of these and other protecting groups are discussed in detail by T. Greene in Protective Groups in Organic Synthesis, John Wiley & Sons, New York, 1981.

The variables shown in the following schemes are as described for compounds of Formula IV, above, unless otherwise indicated.

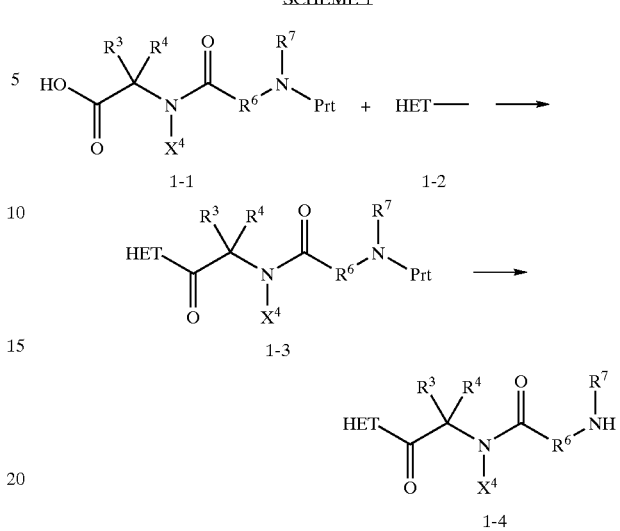

As illustrated in Scheme 1, coupling of a heterocyclic amine (HET at the NH) of formula 1-2, as defined for Formula IV, with a protected amino acid of formula 1-1, where Prt is a suitable protecting group, is conveniently carried out in an inert solvent such as dichloromethane or DMF by a coupling reagent such as EDC, DCC or DEC in the presence of HOBT or HOAT. In the case where amine 1-2 is present as the hydrochloride salt, it is preferable to add one equivalent of a suitable base such as triethylamine to the reaction mixture. Alternatively, the coupling can be effected with a coupling reagent such as BOP in an inert solvent such as methanol or with PPM in a solvent like ethyl acetate. Such coupling reactions are generally conducted at temperatures of about −30° to about 80° C., preferably 0° to about 25° C. For a discussion of other conditions used for coupling peptides see Houben-Weyl, Vol. XV, part II, E. Wunsch, Ed., George Theime Verlag, 1974, Stuttgart. Separation of unwanted side products and purification of intermediates is achieved by chromatography on silica gel, employing flash chromatography (W. C. Still, M. Kahn and A. Mitra, J. Org. Chem. 43 2923 1978), by crystallization, or by trituration. Transformation of 1-3 into an intermediate of formula 1-4 can be carried out by removal of the protecting group Prt as described above.

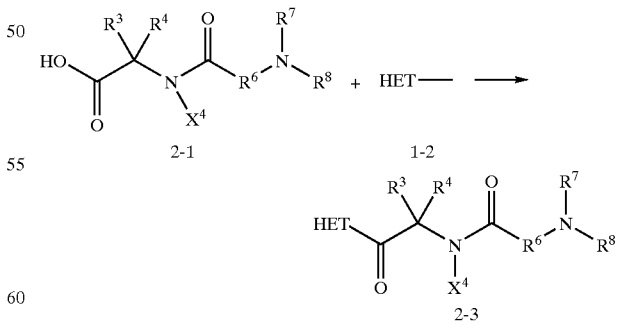

As illustrated in Scheme 2, coupling of a heterocyclic amine of formula 1-2, as defined in claim 1, with an amino acid of formula 2-1, where $R^7$ and $R^8$ are not hydrogen, is conveniently carried out in a manner similar to that described in Scheme 1.

SCHEME 3

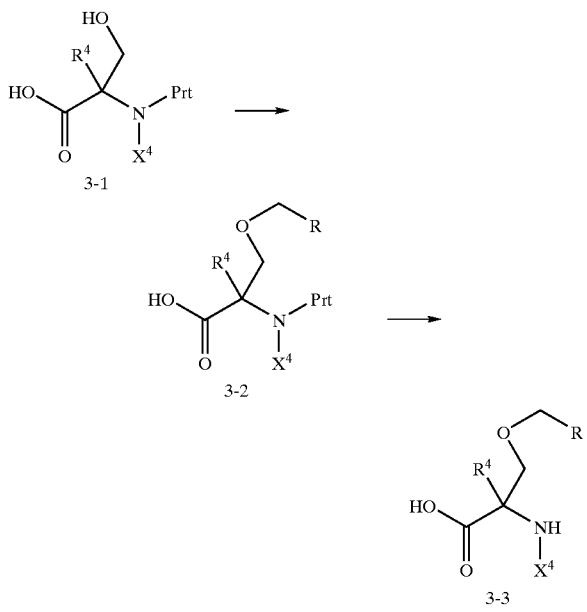

As illustrated in Scheme 3, an intermediate ether of formula 3-2 can be prepared by treating an amino acid of formula 3-1, where Prt is a suitable protecting group, with a base such as potassium carbonate or sodium hydride followed by an alkyl halide, benzyl halide, tosylate or mesylate such as benzylbromide in a suitable solvent such as DMF or THF. Deprotection of the amine transforms 3-2 into 3-3. Alternatively, many amino acids of formula 3-3 are commercially available. R is a group defined for $R^3$ in Formula IV, above.

SCHEME 4

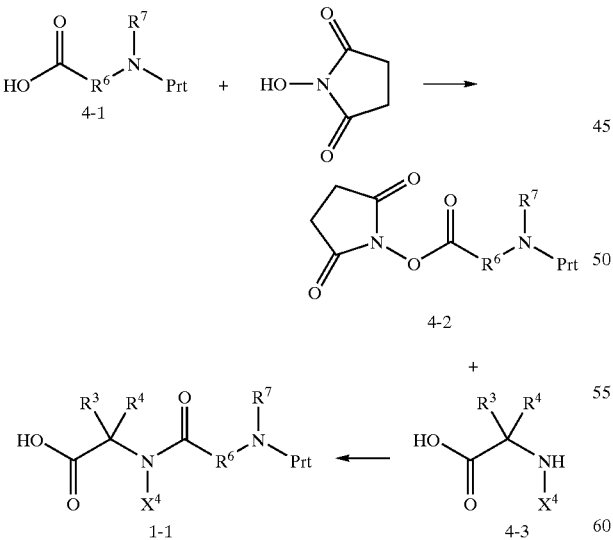

As illustrated in Scheme 4, intermediates of formula 4-2 can be prepared by treating an acid of formula 4-1 with hydroxysuccinimide in the presence of a coupling agent such as EDC in an inert solvent such as methylene chloride. Treating 4-2 with an amino acid of formula 4-3 in a solvent such as DMF in the presence of a base such as diisopropylethylamine produces compounds of formula 1-1.

SCHEME 5

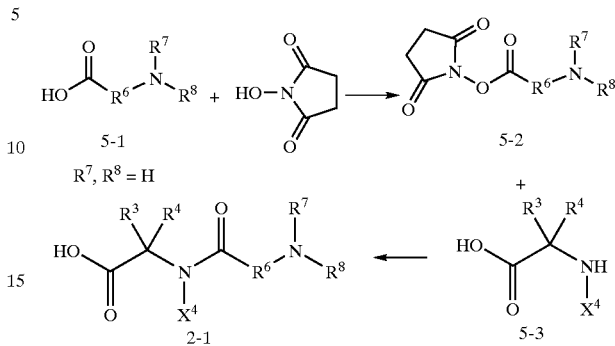

As illustrated in Scheme 5, dipeptides of formula 2-1, where $R^7$ and $R^8$ are not hydrogen, is conveniently synthesized by the procedures described in Scheme 4.

SCHEME 6

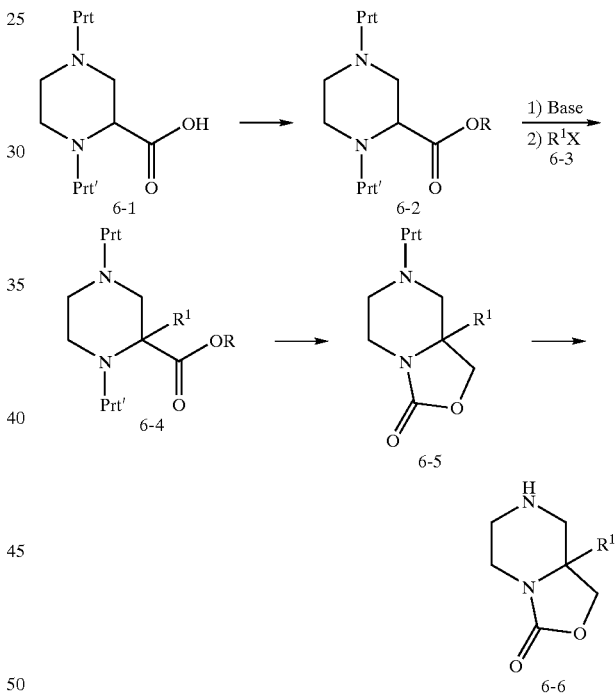

Intermediate esters of formula 6-2, where Prt and Prt' are protecting groups, preferably Prt' is a carbamate protecting group such as CBZ, can be prepared by treating an acid of formula 6-1 with a base such as potassium carbonate followed by an alkyl halide such as iodomethane in a suitable solvent such as DMF. Alternatively, an ester of formula 6-2 can be prepared by reacting an acid of formula 6-1 with diazomethane. For the preparation of compound 6-2 see Bigge, C. F. et al., Tet. Lett., 1989, 30, 5193–5196. Intermediate 6-4 is generated by alkylating ester 6-2 with a reagent such as an alkyl halide, tosylate or mesylate with a base such as NaHMDS in a suitable solvent system such as DMF/THF at a temperature of about −78° C.

Intermediate carbamates of formula 6-5 can be prepared by reacting an intermediate of formula 6-4 with a hydride such as sodium borohydride or superhydride. Transforma-

SCHEME 7

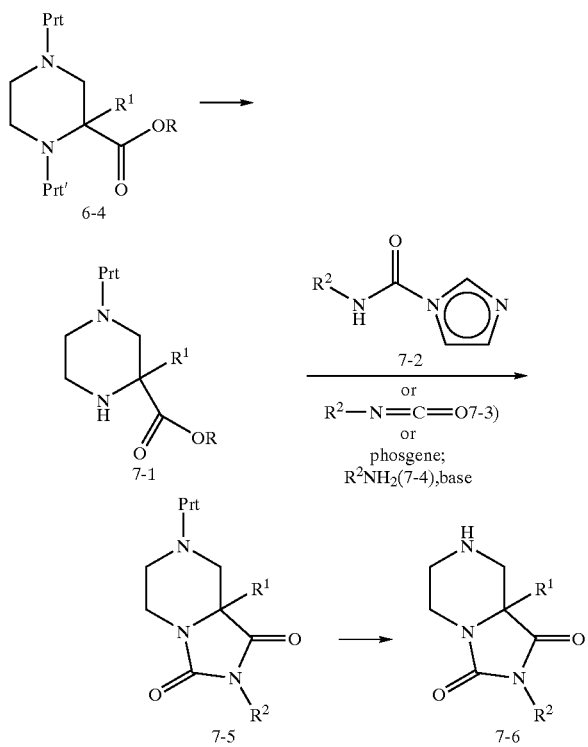

Transformation of intermediate 6-4 to 7-1 can be achieved by removal of the protecting group Prt' as described above. Intermediate ureas of formula 7-5 can be prepared by reacting an intermediate of formula 7-1 with either an acyl imidizolide of formula 7-2, an isocyanate of formula 7-3, or phosgene (or other phosgene equivalent) followed by an amine of formula 7-4 in the presence of a suitable base such as triethylamine. When $R^1$ is —$CH_2$-pyridyl it is preferred to use an isocyanate or acyl imidizolide. Transformation of 7-5 to 7-6 can be achieved by removal of the protecting group Prt as described above.

SCHEME 8

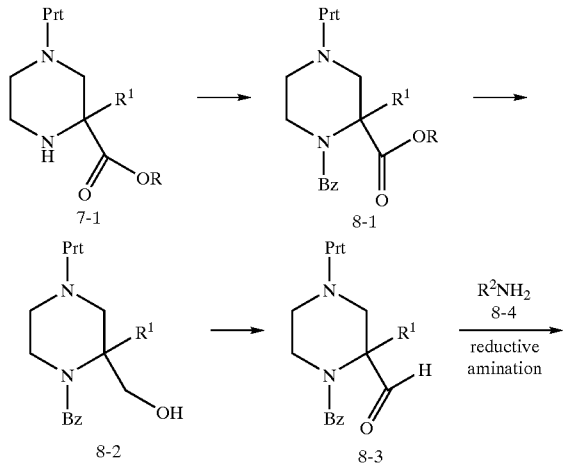

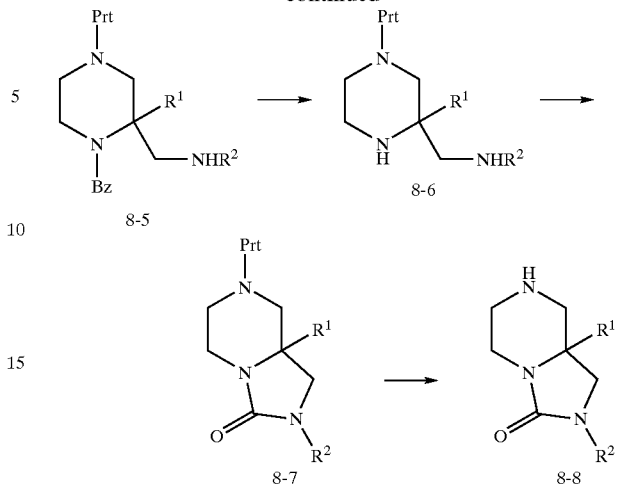

An intermediate benzylamine of formula 8-1 can be prepared by treating an amine of formula 7-1 with a base such as diisopropylethylamine followed by a benzyl halide such as benzyl bromide in a suitable solvent such as acetonitrile. Alternatively, 8-1 can be prepared by treating 7-1 with benzaldehyde and a suitable reducing agent such as $NaCNBH_3$ or $Na(OAc)_3BH$ in a suitable solvent such as methanol or dichloromethane. An alcohol of the formula 8-2 can be prepared by reducing an intermediate of the formula 8-1 with a reducing agent such as superhydride in a suitable solvent such as THF. An alcohol of the formula 8-2 can be oxidized to an aldehyde of the formula 8-3 with an oxidizing agent such as oxalyl chloride/DMSO in a suitable solvent such as dichloromethane at a temperature of about −78° C., with the later addition of a base such as triethylamine to neutralize the reaction mixture (Swern-type oxidation, see Mancuso, A. J., Swern, D., Synthesis, 1981, pp. 165–185). Compounds of formula 8-5 can be prepared by treating an aldehyde of formula 8-3 with an amine of formula 8-4 in the presence of a suitable reducing agent which include alkali metal borohydrides and cyanoborohydrides. The preferred reducing agent is sodium cyanoborohydride. Sodium borohydride and sodium triacetoxyborohydride may also be used. For a general review of reductive aminations see R. F. Borch, Aldrichimica Acta, 8, 3–10 (1975). Removal of the benzyl group to give 8-6 can be accomplished by a number of reductive methods including hydrogenation in the presence of platinum or palladium catalyst in a protic solvent such as methanol. Cyclization of a diamine of formula 8-6 with CDI or other phosgene equivalents generates a compound of formula 8-7. Removal of the protecting group, as described above, transforms 8-7 into 8-8.

SCHEME 9

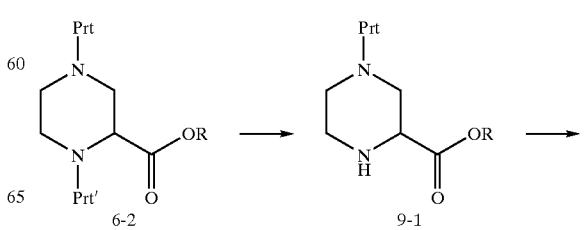

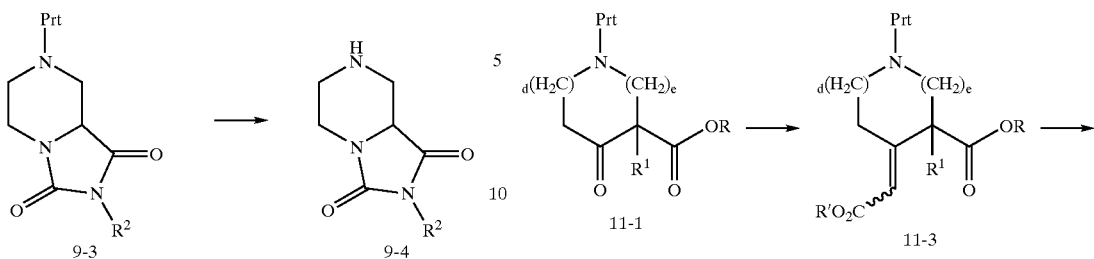

As illustrated in Scheme 9, an intermediate hydantoin of formula 9-4 can be prepared in three steps. An ester of formula 9-1, prepared by cleavage of Prt' from 6-2, can be acylated with an acyl imidizolide of formula 7-2, an isocyanate of formula 7-3, or phosgene (or other phosgene equivalent) followed by an amine of formula 7-4 in the presence of a suitable base such as triethylamine. Transformation of 9-3 to 9-4 can be accomplished by removal of the protecting group Prt as described above.

SCHEME 10

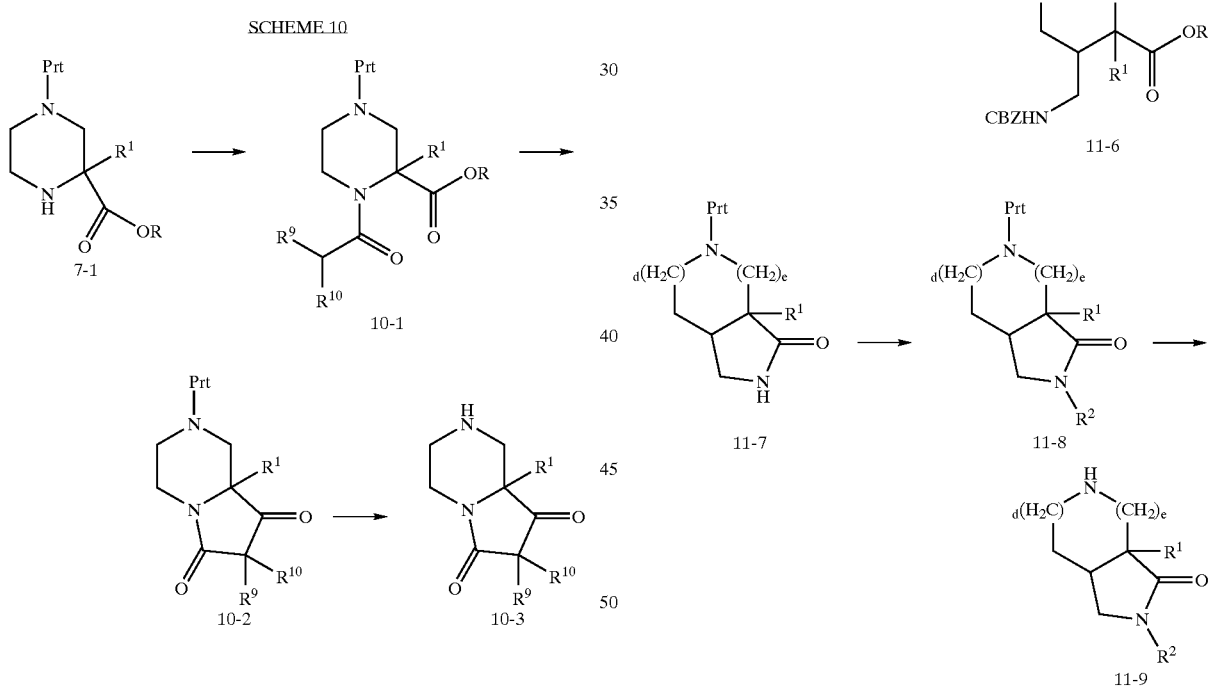

Intermediates of formula 10-1 can be prepared by treating a compound of formula 7-1 with an acyl chloride or other activated carboxylic acid derivative and a suitable base, such as TEA or N,N-diisopropylethylamine. Cyclization of a compound of formula 10-1 occurs upon treating 10-1 with a strong base such as LHMDS at a suitable temperature, about −78° C. to 40° C., to produce an intermediate of formula 10-2. When $R^9$ and/or $R^{10}$ is H, 10-2 may be alkylated with a reagent such as methyl iodide in the presence of a base like NaH to give 10-2 where $R^9$ and $R^{10}$ are not H. Removal of the protecting group, as described above, transforms 10-2 to 10-3.

Intermediate α,β-unsaturated esters of formula 11-3 (R is an alkyl group ) can be prepared by olefinating 11-1 with a reagent such as the anion generated upon treating trimethylphosphonoacetate with a strong base such as potassium tert-butoxide in a suitable solvent such as THF. Catalytic hydrogenation, such as with Pd on carbon in the presence of hydrogen, preferably at 1-4 atmospheres, in a suitable solvent, such as ethyl acetate or methanol, reduces the double bond of 11-3 to produce 11-4. Selective hydrolysis of the less hindered ester group in 11-4 can be performed with a base such as an alkali metal hydroxide in an appropriate solvent, such as a mixture of water, methanol, and/or dioxane. A carboxylic acid of formula 11-5, thus produced can be transformed to 11-6 by converting 11-5 to an acyl azide, such as with DPPA and TEA in benzene, followed by rearrangement to an isocyanate by heating to reflux in a solvent such as benzene, which is then reacted with benzyl alcohol to form 11-6. A lactam of formula 11-7 can be prepared by removal of the CBZ protecting group from the amine in 11-6, followed by cyclization of the amine with the adjacent ester group. Deprotection of this material provides 11-9, $R^2$=H. Alternatively, amide 11-7 can be alkylated by deprotonation with a strong base such as sodium hydride, LHMDS, or KHMDS in a suitable solvent such as DMF or THF followed by treatment with an alkylating agent such as an alkyl halide, mesylate or tosylate. The product, 11-8, may then be deprotected, as described above, to provide 11-9. One skilled in the art will recognize that substitution next to the lactam nitrogen could have been introduced by alkylating ester 11-4 or by olefinating 11-1 to give a tetra-substituted olefin analogous to 11-3.

SCHEME 12

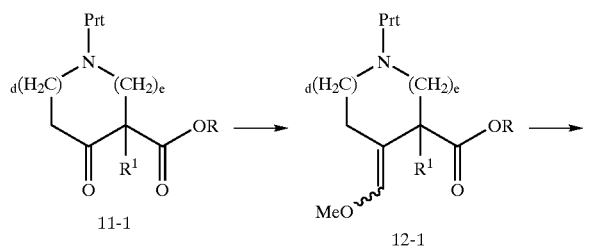

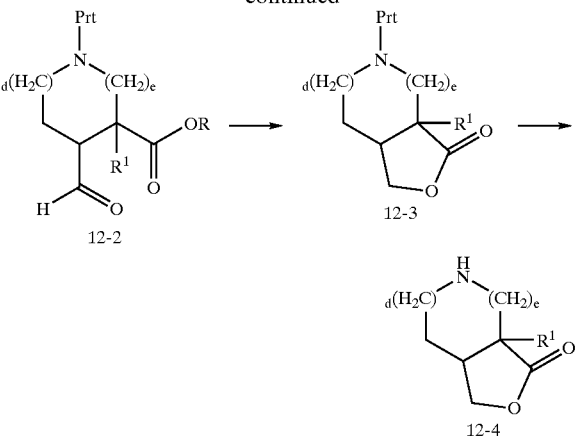

Intermediate enol ethers of formula 12-1 can be prepared by treating 11-1 (R is an alkyl group) with a reagent, such as methoxymethyl triphenylphosphonium chloride and a strong base, such as potassium tert-butoxide, in a suitable solvent such as THF. Hydrolysis of an enol ether of formula 12-1 under acidic conditions produces aldehyde 12-2. Reduction of the aldehyde group to an alcohol, for example with sodium borohydride in methanol, followed by cyclization converts 12-2 to a lactone of formula 12-3. Deprotection of the nitrogen, as described above, affords 12-4. One skilled in the art will recognize that an $R^{14}$ substituent could have been introduced by alkylating aldehyde 12-2. In addition, substitution next to the lactone oxygen ($R^9$/$R^{10}$) could be introduced by olefinating 11-1 to give a tetra-substituted olefin and by treating the latter ketone or aldehyde (12-2) with an alkyl metal such as a Grignard reagent.

SCHEME 13

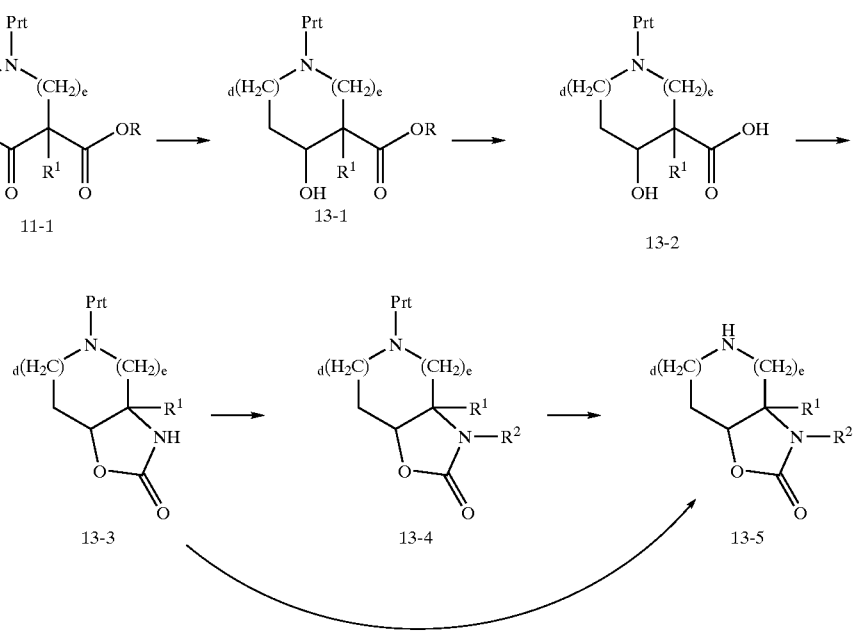

Reduction of the ketone in 11-1 (R is an alkyl group) to an alcohol with a suitable reducing reagent, such as with sodium borohydride in methanol, converts 11-1 to 13-1. Hydrolysis of the ester group in 13-1 according to the method discussed in Scheme 11 produces acid 13-2. Transformation of 13-2 to 13-3 can be achieved by converting 13-2 to acyl azides, for instance with DPPA and TEA in a solvent such as benzene, followed by rearrangement to isocyanates, which then react intramolecularly with the adjacent alcohol to form carbamate 13-3. Deprotection of 13-3 as described above would provides 13-5 where $R^2$ is H. Alternatively, carbamate 13-3 can be alkylated by deprotonation with a strong base such as sodium hydride, LHMDS, or KHMDS in a suitable solvent such as DMF or THF followed by treatment with an alkylating agent such as an alkyl halide ($R^2$-halide), mesylate or tosylate. Removal of the protecting group, as described above, transforms 13-4 to 13-5. One skilled in the art will recognize that an $R^{1A}$ substituent could have been introduced by treating ketone 11-1 with an alkyl metal reagent, such as methyl magnesium bromide, at a suitable temperature for a Grignard reaction.

Removal of the carbamate protecting group, Prt, from 11-1 (R is an alkyl group) produces 14-1. Reprotection, such as with a benzyl group gives 14-2. Treating 14-2 with hydroxylamine yields an oxime of formula 14-3. The oxime and ester groups in 14-3 can be reduced to an amine and alcohol, respectively, to form 14-4 with a suitable reducing reagent, such as with LAH in THF. Transformation of 14-4 to a carbamate of formula 14-5 can be achieved by reaction of 14-4 with CDI or another phosgene equivalent in the presence of a base like TEA and solvent such as DME. Deprotection of 14-5 produces 14-7 where $R^2$ is H. Alternatively, alkylation of the carbamate as described above (Scheme 13) affords 14-6, which can be deprotected, as described above, to give 14-7.

SCHEME 15

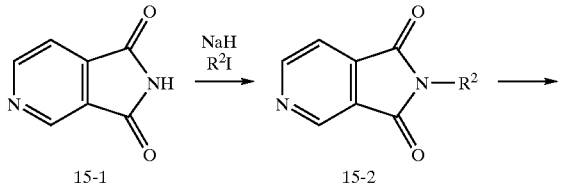

SCHEME 14

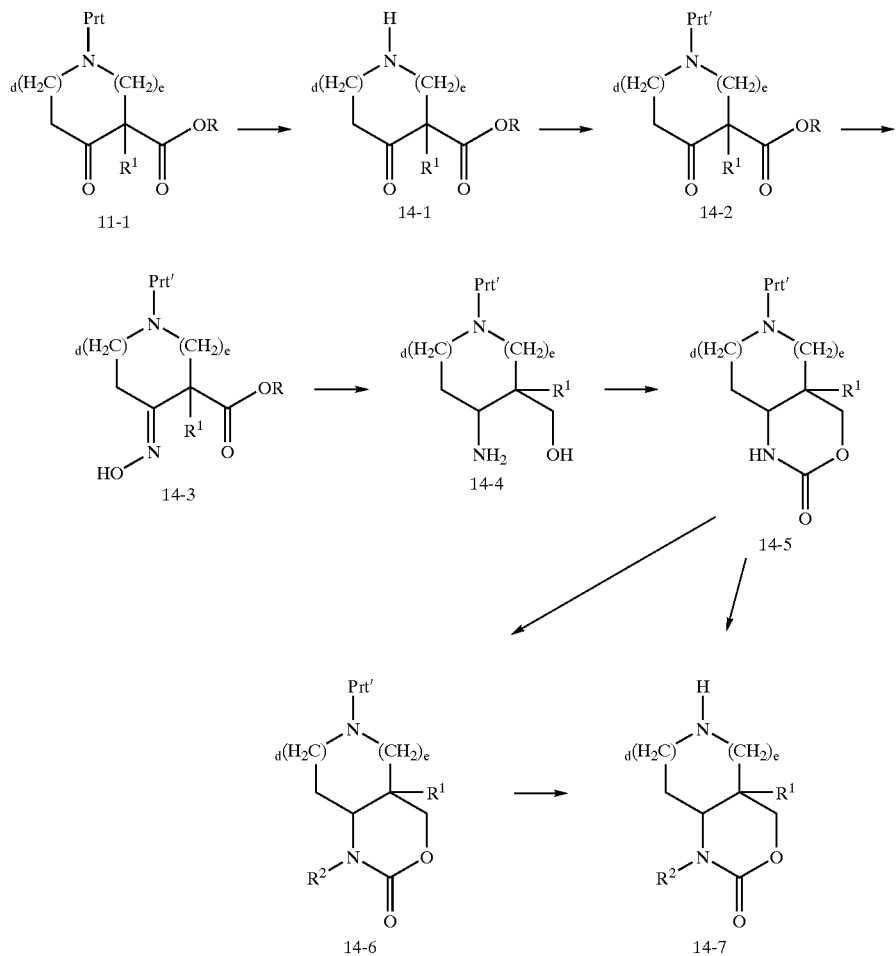

33

-continued

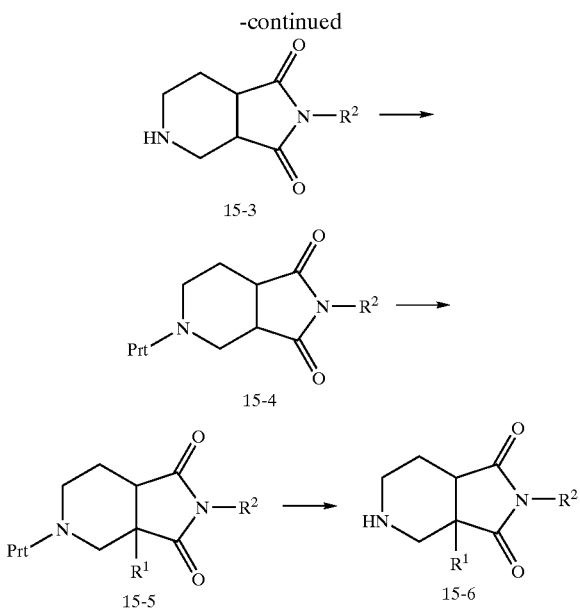

Treating 15-1 with a strong base such as sodium hydride in a suitable solvent such as DMF, followed by treatment with an alkylating agent, such as an alkyl halide, mesylate or tosylate, produces an N-substituted imide of formula 15-2. Reduction of the pyridine ring by catalytic hydrogenation, such as with Pd on carbon in an ethanolic HCl solution converts 15-2 to 15-3. Protection of the nitrogen, such as with a benzyl group, gives 15-4. A compound of the formula 15-5 can be generated upon deprotonation of 15-4 with a suitable strong base such as LHMDS in a solvent such as THF at a temperature of about −78° C., followed by alkylation with an electrophile such as an alkyl halide such as benzyl bromide. Cleavage of the protecting group, as described above, then gives 15-6.

34

SCHEME 16

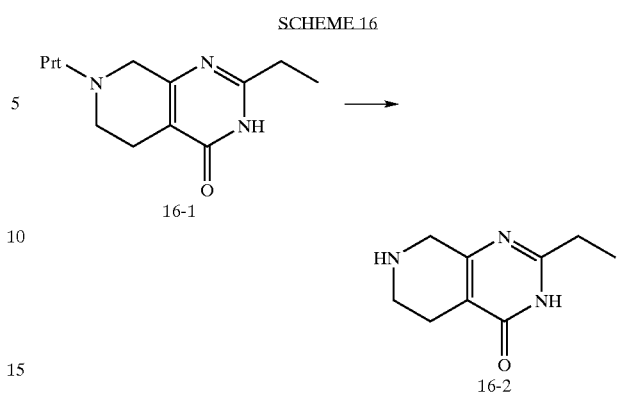

Deprotection of 16-1 as described above produces 16-2.

SCHEME 17

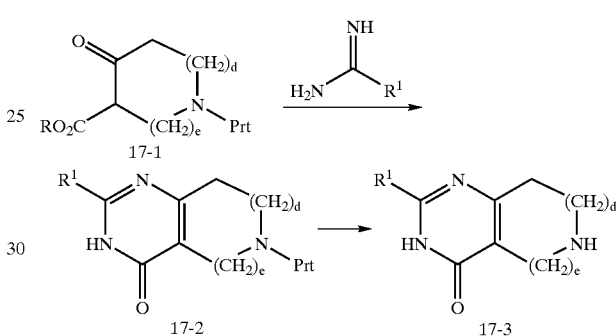

Condensation of 17-1 (R is an alkyl group) with an amidine in a solvent such as ethanol at an elevated temperature, preferably refluxing solvent, produces a heterocyclic intermediate of formula 17-2. Deprotection of 17-2, as described above, gives an intermediate of formula 17-3.

SCHEME 18

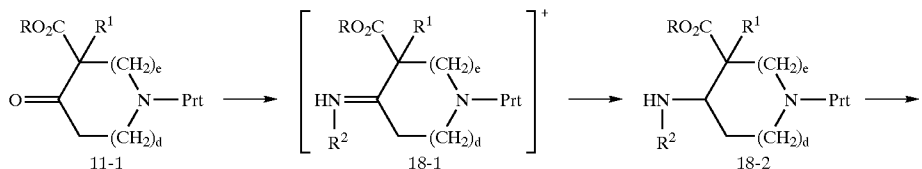

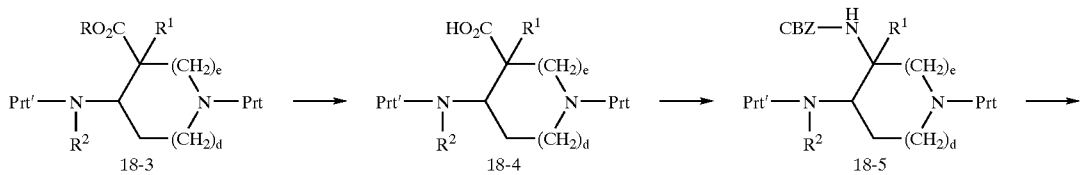

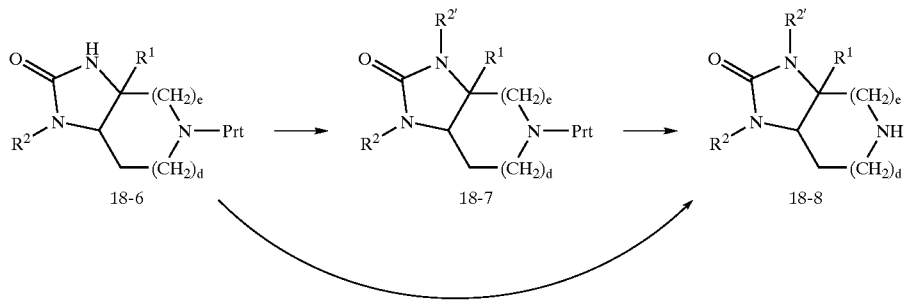

An intermediate amine of formula 18-2 can be prepared from a ketone of formula 11-1 (R is an alkyl group) by reductive amination as described above (see Scheme 8). Protection of the secondary amine in 18-2 produces 18-3. Intermediate carboxylic acids of formula 18-4 can be prepared by hydrolysis of the ester group of formula 18-3 (see Scheme 11). Transformation of 18-4 to 18-5 can be achieved through an intermediate acyl azide as described above (see Scheme 11). Cyclization of an intermediate of formula 18-5 at a suitable temperature after removing Prt' yields an intermediate urea of formula 18-6. Deprotection of 18-6 provides 18-8 where $R^{2'}$ is H. Alternatively, urea 18-6 can be alkylated by deprotonation with a strong base such as sodium hydride, LHMDS, or KHMDS in a suitable solvent such as DMF or THF followed by treatment with an alkylating agent such as an alkyl halide, mesylate or tosylate. Removal of the protecting group transforms 18-7 to 18-8 where $R^2$ and $R^{2'}$ are each alkyl.

As illustrated in Scheme 19, reduction of a ketoester of formula 19-1, such as with sodium borohydride in methanol, preferably at 0° C., produces an alcohol of formula 19-2. An intermediate of formula 19-3 can be prepared by protection of the hydroxyl group in an intermediate of formula 19-2 with a suitable protecting group, such as forming a tetrahydropyranyl acetal or silyl ether. Transformation of the ester of formula 19-3 to amide 19-5 can be achieved as described above (see Scheme 11). Deprotection of the hydroxy group of 19-5 yields the free alcohol intermediate, which can be oxidized to an intermediate ketone of formula 19-6 with a suitable oxidizing agent, such as pyridinium chlorochromate or a Swern-type reagent (see Scheme 8). Transformation of 19-6 to a cyclized carbamate of formula 19-7 can be achieved by treating 19-6 with an alkyl metal, such as a Grignard reagent, in a suitable solvent such as THF, followed by cyclization. Removal of the protecting group then yields 19-9 wherein $R^2$ is H. Alternatively, the carbamate of 19-7 may be alkylated as described above (see Scheme 13) to afford 19-8, which can then be deprotected to provide

SCHEME 19

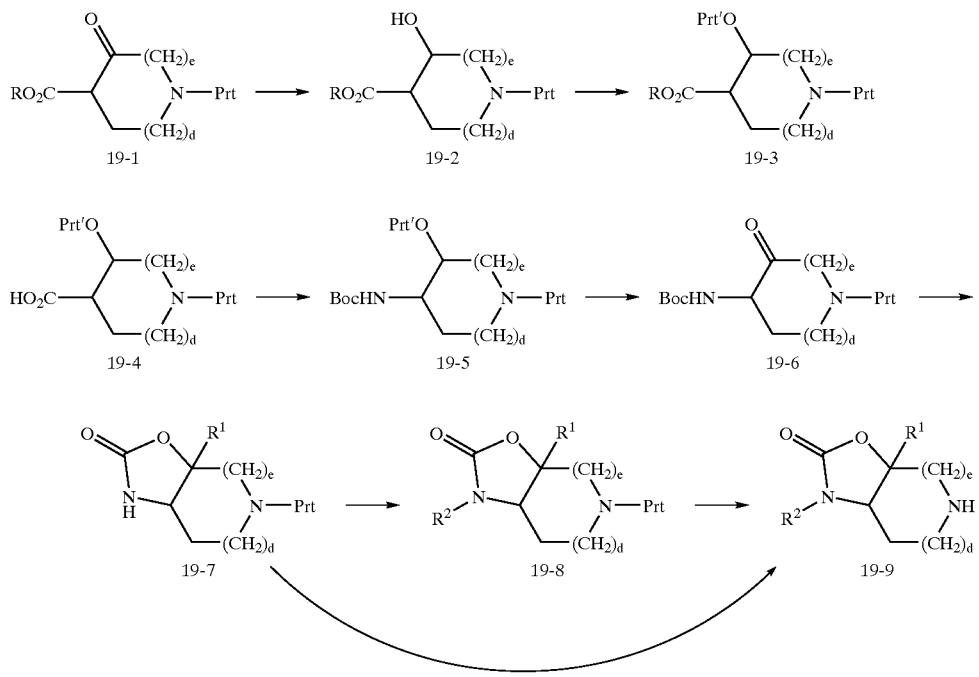

19-9. Those skilled in the art will recognize that an $R^{1A}$ substituent could have been introduced by alkylating ketoester 19-1.

SCHEME 20

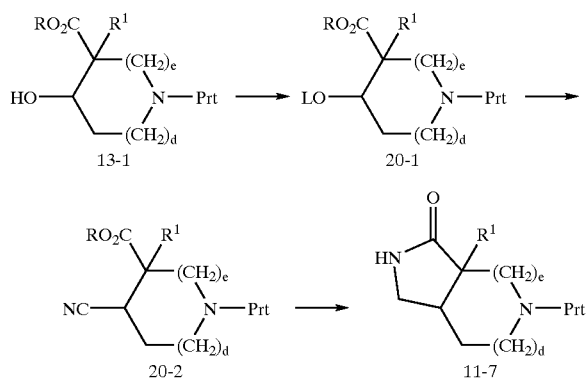

An alternate synthesis of lactam 11-7 is illustrated in Scheme 20. An alcohol of formula 13-1 can be converted to an intermediate nitrile of formula 20-1 by first activating the hydroxyl of 13-1 (R is an alkyl group), such as with methanesulfonyl chloride or methanesulfonic acid in a suitable solvent, such as methylene chloride in the presence of an amine base. Subsequent reaction of 20-1 (LO— is an activated hydroxyl) with a cyanide salt, such as potassium cyanide, then yields an intermediate nitrile of formula 20-2, which can be transformed to 11-7 by catalytic hydrogenation of the nitrile to amine, which then reacts with the ester group to form lactam (11-7). Those skilled in the art will recognize that an $R^1A$ substituent could be introduced by alkylating nitrile 20-2.

SCHEME 21

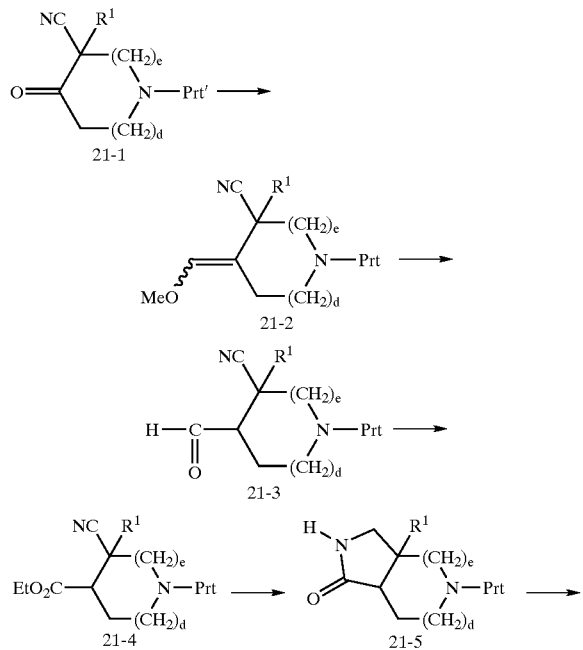

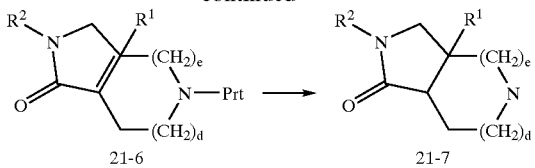

Nitriles of formula 21-1 can be prepared from esters, acid halides and acids of formula 11-1 by a variety of known methods (for examples, see R. Larock pages 976, 980 and 988 in Comprehensive Organic Transformations: A Guide to Functional Group Preparations, VCH Publishers, 1989).

Homologation of ketones of formula 21-1 to provide 21-3 as described above (Scheme 12) yields an aldehyde of formula 21-3. Oxidation of the aldehyde group in 21-3, such as with sodium hypochlorite, provides an acid which can be esterified to give 21-4 by a number of methods described above (Scheme 6). Reduction of the nitrile group in a compound of formula 21-4, such as by catalytic hydrogenation over Pd on carbon, gives an amine which will cyclize to give a lactam of formula 21-5. Deprotection of 21-5 yields 21-7, $R^2$ is H. Alternatively, alkylation of the amide of formula 21-5 as described above (Scheme 11) yields an N-substituted amide of formula 21-6, which can be deprotected to provide 21-7. Those skilled in the art will recognize that an $R^{1A}$ substituent could have been introduced by alkylating ester 21-4.

SCHEME 22

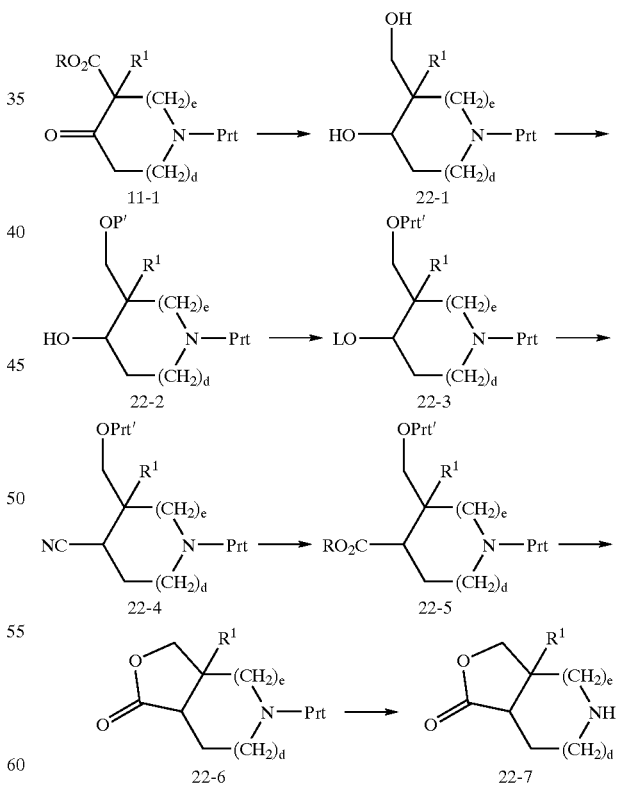

Intermediate alcohols of formula 22-1 can be prepared by reducing the ketone and ester groups of 11-1 (R is an alkyl group), such as with a metal borohydride or lithium aluminum hydride in a suitable solvent such as THF. Selective protection of the primary hydroxyl group of the intermediate of formula 22-1 with a suitable protecting group, such as a trialkylsilyl ether or pivaloyl ester gives a secondary alcohol of formula 22-2. An intermediate nitrile of formula 22-4 can be prepared from the alcohol of formula 22-2 by methods described above (see Scheme 20). An intermediate nitrile of formula 22-4 can be transformed to an ester of formula 22-5 by alcoholysis of nitrile 22-4, for instance with aqueous HCl or sodium hydroxide in ethanol. Removal of the alcohol protecting group and reaction of the hydroxyl group with the adjacent ester group in 22-5 forms a lactone of formula 22-6. Deprotection as described above yields 22-7. Those skilled in the art will recognize that an $R^{1A}$ substituent could have been introduced by treating ketone 11-1 with the appropriate alkyl metal reagent. Substitution ($R^9$, $R^{10}$) adjacent to the lactone oxygen could then be introduced by treating the ester with the appropriate alkyl metal reagent (the ketone would have to be reduced if $R^{1A}$ is not O).

recognize that an $R^{1A}$ substituent could have been introduced by conjugate addition to the unsaturated nitrile (23-1), such as with an alkyl cuprate. In addition, $R^9$, $R^{10}$ substituents can be introduced next to the lactam carbonyl by alkylating nitrile 23-2.

SCHEME 24

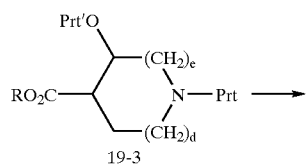

SCHEME 23

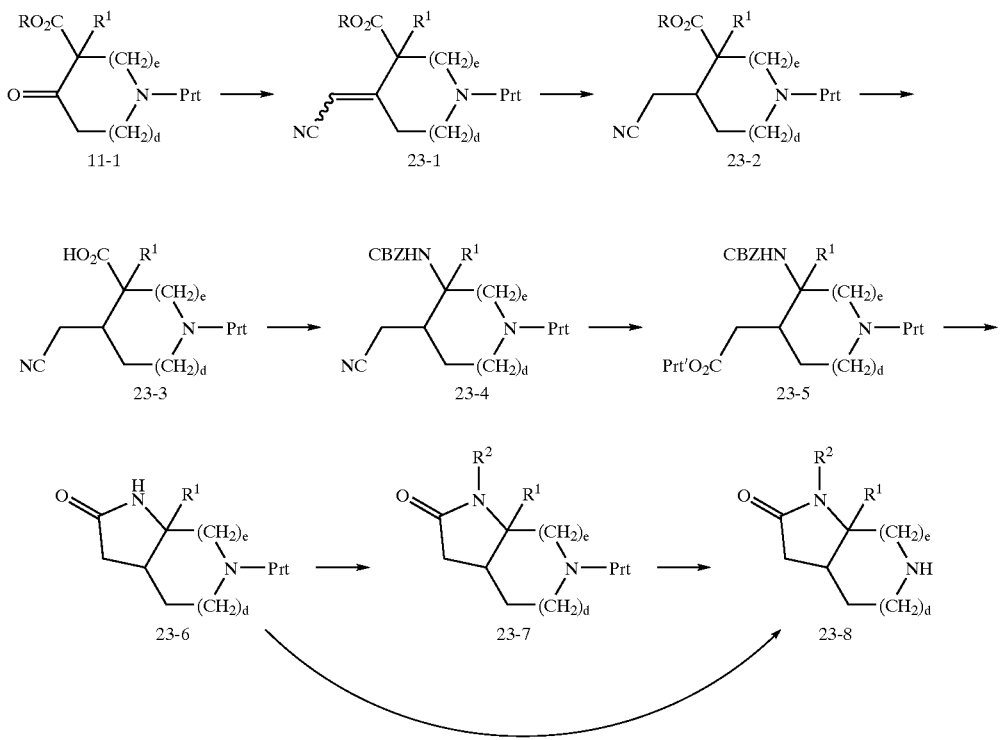

Intermediate α,β-unsaturated nitriles of formula 23-1 can be prepared by olefinating 11-1 (R is an alkyl group) with a reagent such as cyanomethyltriphenylphosphonium chloride and a strong base, such as KHMDS, in a suitable solvent, such as THF. Reduction of the double bond in 23-1, such as with sodium borohydride in pyridine, produces nitrile 23-2. The ester group of formula 23-2 can then be transformed to a carbamate of formula 23-4 by methods described above (see Scheme 11). Alcoholysis of the nitrile of 23-4 in an alcoholic solvent under acidic condition produces an ester of formula 23-5. A lactam of formula 23-6 can be prepared by removal of the CBZ protecting group, followed by cyclization of the amine with the adjacent ester group. Deprotection at this stage provides 23-8, $R^2$ is H. Alternatively, alkylation of the amide (according to Scheme 11) provides an N-substituted lactam, which can be converted to 23-8 by deprotection as described above. One skilled in the art will -continued

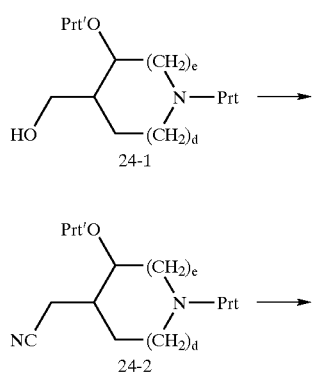

-continued

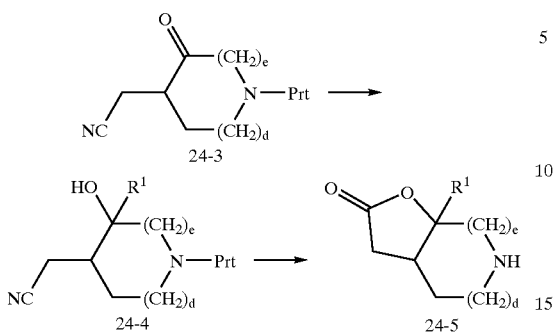

As illustrated in Scheme 24, an alcohol of formula 24-1 can be prepared from 19-3 (R is an alkyl group) by reduction of the ester with a reducing reagent such as lithium borohydride in a solvent such as THF. A nitrile of formula 24-2 can be prepared from the alcohols of formula 24-1 by methods described above (see Scheme 20). Deprotection of the alcohol of 24-2 followed by oxidation of the hydroxyl as previously described (see Scheme 19) produces a ketone 24-3. Treating 24-3 with an alkyl metal such as a Grignard reagent in a suitable solvent such as THF gives an intermediate of formula 24-4. The cyano group of 24-4 can then be converted to an ester by alcoholysis as described above (Scheme 22). Reaction of the tertiary alcohol with the neighboring ester forms a lactone which can then be deprotected to give 24-5. One skilled in the art will recognize that an $R^{1A}$ substituent could be introduced by alkylating ester 19-3. In addition, $R^9$, $R^{10}$ substituents could be introduced adjacent to the lactone carbonyl by alkylation before final deprotection.

SCHEME 25

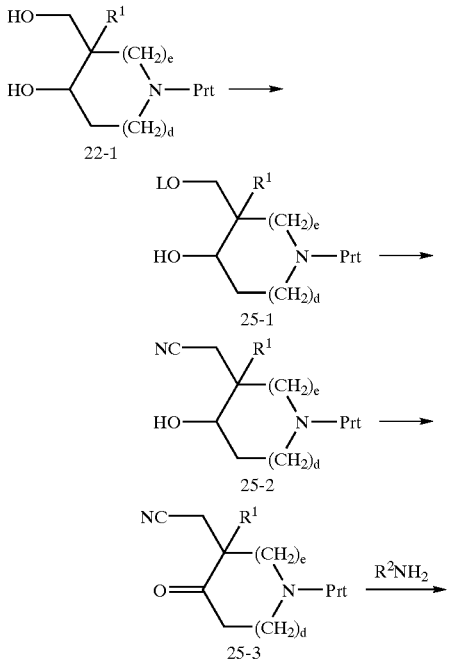

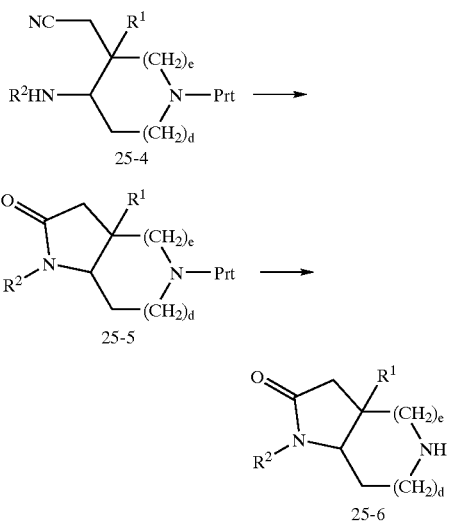

Intermediate of formula 25-1 (LO— is an activated hydroxyl) can be prepared by selective activation of the primary hydroxyl, for instance by tosylation of the less hindered hydroxyl group of 20-1 with tosyl chloride in a suitable solvent. Treating 25-1 with a reagent such as potassium cyanide in a suitable solvent produces a nitrile of formula 25-2. Oxidation of the alcohol (see Scheme 19) of formula 25-2 gives a ketone of formula 25-3. Transformation of 25-3 to 25-4 can be achieved by reductive amination as was described above (see Scheme 8). The cyano amine of formula 25-4 can be converted to a lactam of formula 25-5 by treating 25-4 with a strong acid or base in a protic solvent such as ethanol. Removal of the protecting group on the secondary nitrogen can then provide lactam 25-6. One skilled in the art will recognize that $R^9$, $R^{10}$ substituents could be introduced by alkylation of lactam 25-5.

SCHEME 26

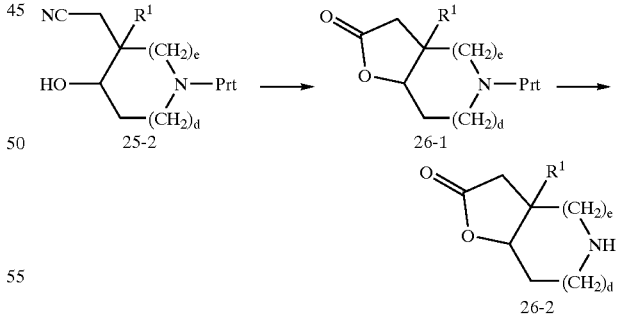

A lactone of formula 26-1 can be prepared by treating a cyano alcohol of formula 25-2 with a strong acid such as HCl, or a strong base such as NaOH, in a protic solvent such as EtOH. Deprotection, as described above, of the secondary amine of formula 26-1 gives 26-2. One skilled in the art will recognize that $R^9$, $R^{10}$ substituents can be introduced by alkylation of lactone 26-1.

SCHEME 27

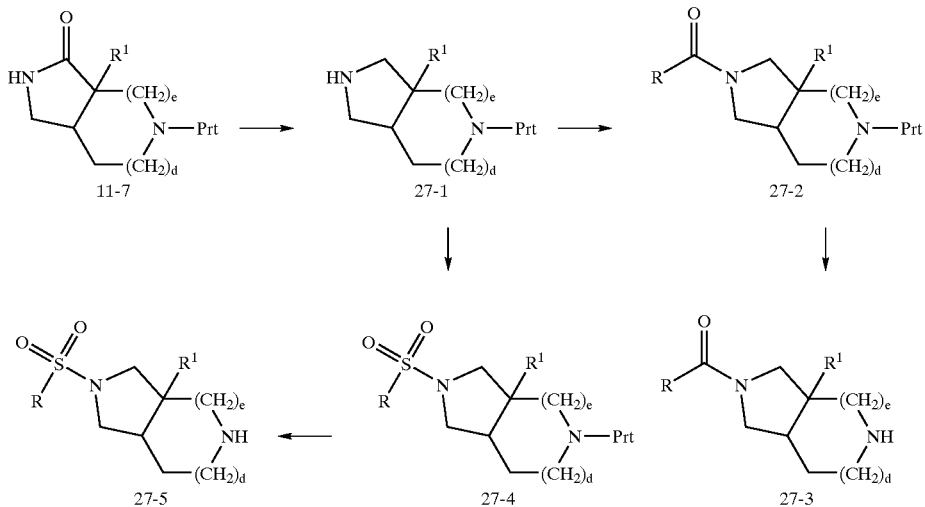

Intermediates of formula 27-1 can be prepared by reducing a lactam of formula 11-7 to a pyrrolidine with a suitable reducing reagent such as borane or lithium aluminum hydride in a suitable solvent such as THF. Treating 27-1 with an acyl chloride of formula RCOCl (where R is an alkyl group) in a suitable solvent produces an intermediate amide of formula 27-2. Removal of the protecting group of the amide of formula 27-2 by the method described previously gives an amide of formula 27-3.

A sulfonamide of formula 27-5 can be prepared by treating 27-1 with a sulfonate such as tosyl chloride in the presence of a base such as pyridine to yield 27-4, followed by removal of the protecting group as previously described.

SCHEME 28

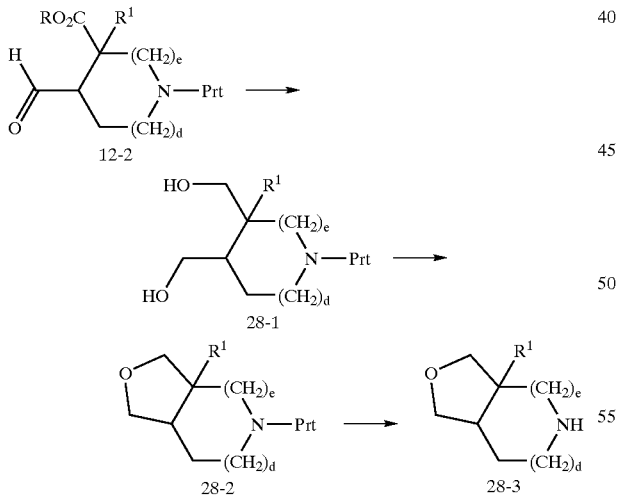

Intermediate diols of formula 28-1 (R is an alkyl group) can be prepared by treating 12-2 with a suitable reducing agent, such as lithium borohydride, in an appropriate solvent, such as THF. Methods for converting diol 28-1 to furan 28-2 include dehydration under acidic conditions, dehydration with a reagent such as $Ph_3P(OEt)_2$, or reaction with a reagent such as toluenesulfonylchloride in the presence of a base followed by displacement of the activated alcohol with the remaining hydroxyl group. Removal of the protecting group from 28-2 subsequently forms a compound of formula 28-3. One skilled in the art will recognize that an $R^{1A}$ substituent can be added by alkylating aldehyde 12-2. In addition, $R^9$, $R^{10}$ substituents can be introduced by treating 12-2 with an alkyl metal reagent.

SCHEME 29

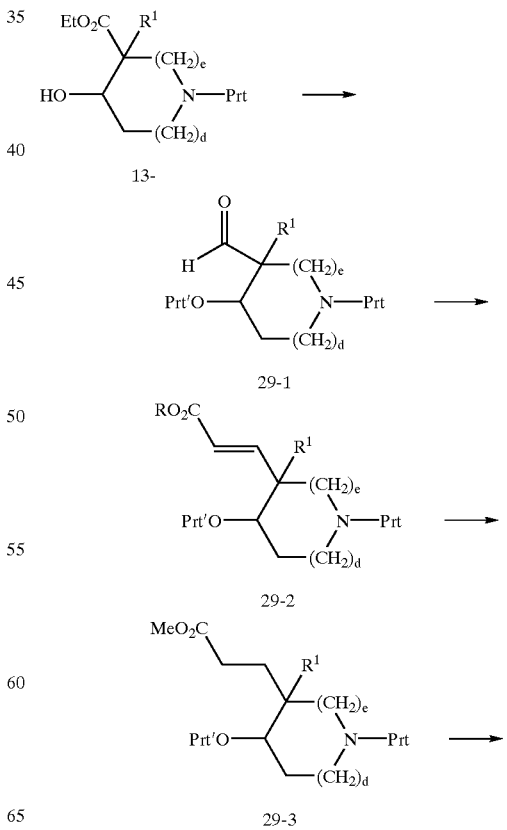

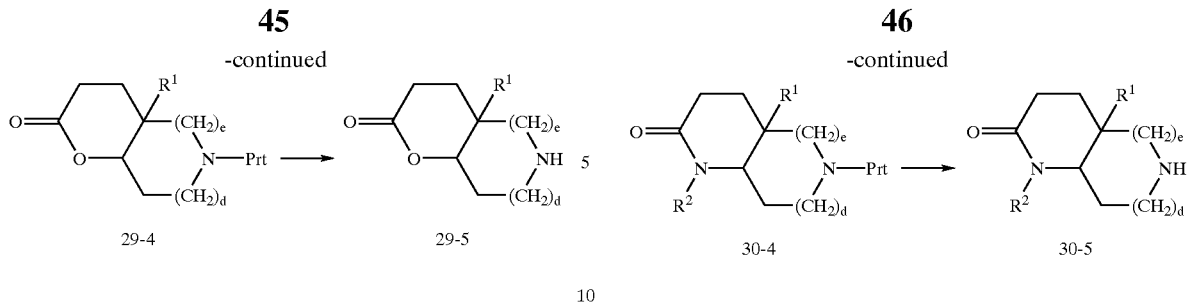

Intermediate aldehydes of formula 29-1 can be prepared by protecting the secondary alcohol of 13-1 such as with a silyl ether, followed by reduction of the ester with a reducing reagent such as diisobutylaluminum hydride at −78° C. in a suitable solvent. Alternatively, 13-1 can be reduced to the primary alcohol with a reagent such as lithium borohydride, and then oxidized to the aldehyde with a variety of reagents described above (see Scheme 8). Homologation of aldehydes of formula 29-1 to saturated esters of formula 29-3 can be performed as previously described (see similar homologation of ketones in Scheme 11). Deprotection of the secondary alcohol of 29-3, followed by cyclization produces lactones of formula 29-4. Deprotection of 29-4 will then give 29-5. An $R^9$ substituent β to the lactone carbonyl may be introduced by conjugate addition to unsaturated ester 29-2, such as with an alkyl cuprate. In addition, $R^9$, $R^{10}$ substituents could be introduced next to the lactone carbonyl by alkylating lactone 29-4.

Intermediate ketones of formula 30-1 can be prepared by deprotecting the secondary hydroxyl of 29-3 (R is an alkyl group), followed by oxidation of the alcohol to a ketone (see Scheme 19). Reductive amination of 30-1 with a primary amine as previously described (see Scheme 8) produces intermediate 30-3. Cyclization of 30-3 at a suitable temperature yields a lactam of formula 30-4, which can be deprotected to give 30-5. One skilled in the art will recognize that $R^9$, $R^{10}$ substituents can be introduced by alkylation of lactam 30-4.

SCHEME 30

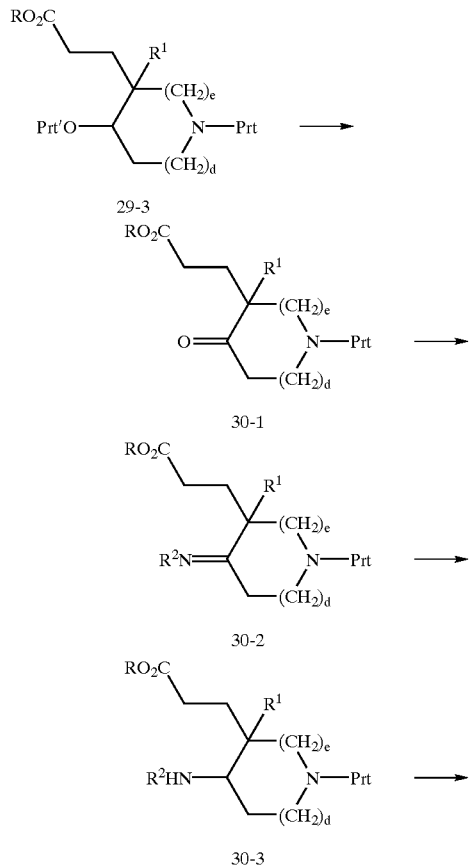

SCHEME 31

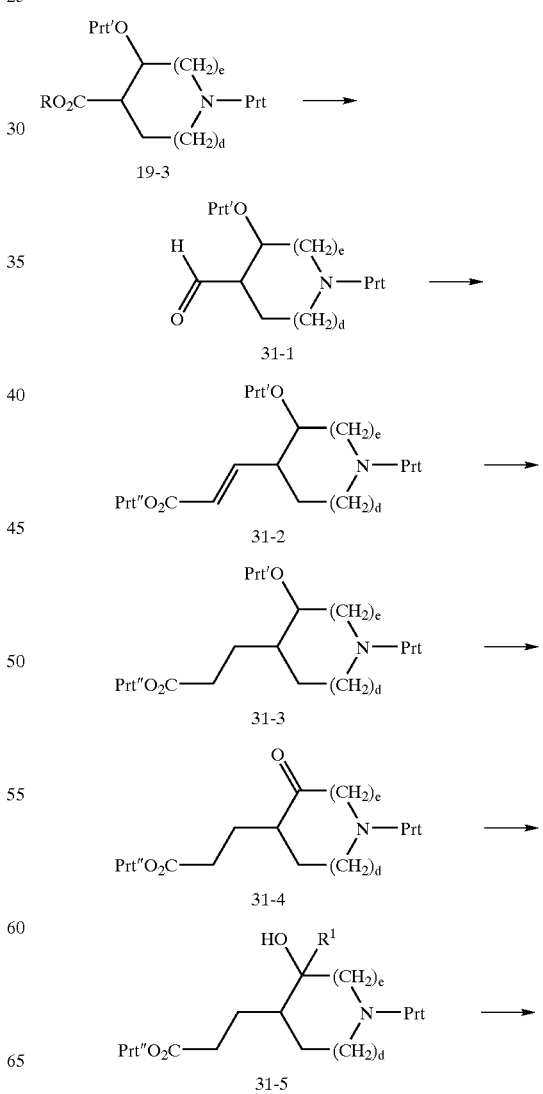

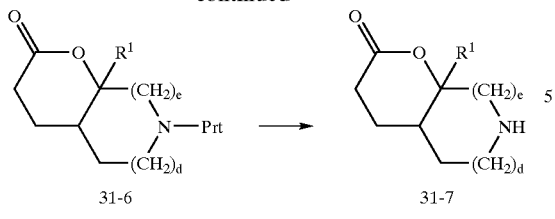

Homologation of 19-3 (R is an alkyl group) to an ester of formula 31-3 can be performed analogously to routes described above (see Scheme 29). Removal of Prt' of 31-3 gives a secondary alcohol which can be oxidized as was previously described (see Scheme 19) to produce a ketone of formula 31-4. Treating 31-4 with an alkyl metal reagent, such as a Grignard reagent, in a suitable solvent produces intermediate 31-5, which can be cyclized to form lactone 31-6. Removal of the protecting group then produces 31-7. One skilled in the art will recognize that an $R^{1A}$ substituent may be introduced by alkylation of ester 19-3. A substituent β to the lactone carbonyl may be introduced by conjugate addition to unsaturated ester 31-2, such as with an alkyl cuprate. Also, $R^9$, $R^{10}$ substituents can be introduced next to the lactone by alkylation of 31-6.

SCHEME 32

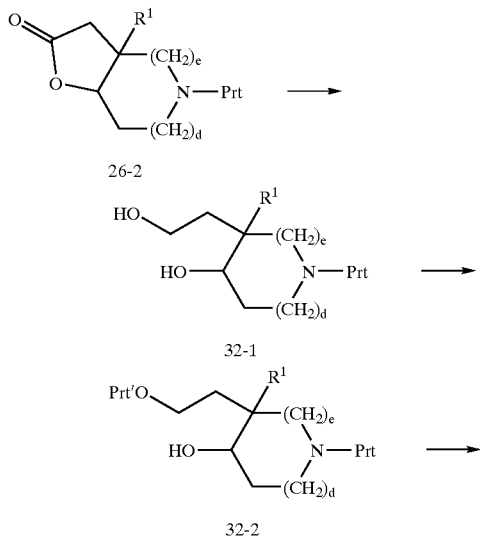

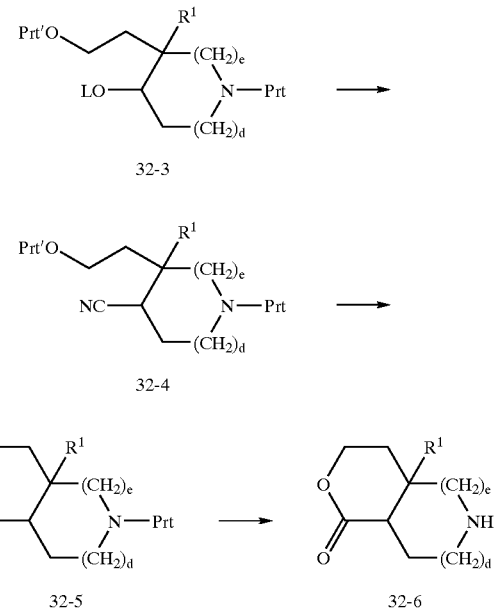

Intermediate diols of formula 32-1 can be prepared by reducing the lactone group of 26-2 with a reagent such as lithium aluminum hydride in a suitable solvent such as THF at a suitable temperature. Selective protection at the less hindered hydroxy group of 32-1, such as with t-butyldimethylsilyl chloride using triethylamine in the presence of DMAP in a solvent such as dichloromethane, produces alcohol 32-2. Conversion of alcohol 32-2 to a nitrile of formula 32-4 may be accomplished as described above (LO— is an activated hydroxyl group) (see Scheme 20). Alcoholysis of the cyano group of formula 32-4 (see Scheme 22), deprotection of the alcohol, and subsequent lactonization forms lactones of formula 32-5. Deprotection of an amine of formula 32-5 gives a lactone of formula 32-6. One skilled in the art will recognize that $R^9$, $R^{10}$ substituents can be introduced β- to the ring oxygen in lactone 32-6 by alkylating lactone 26-2. Substitution α to the lactone ring oxygen may be introduced by treating 26-2 with an alkyl metal reagent.

SCHEME 33

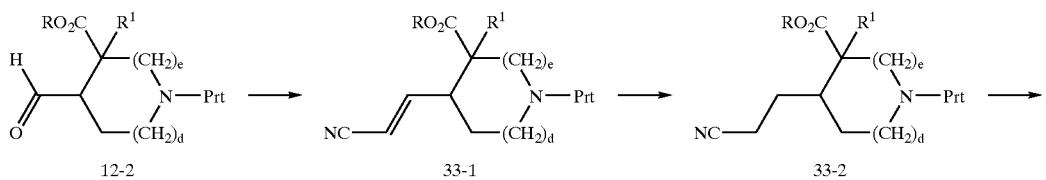

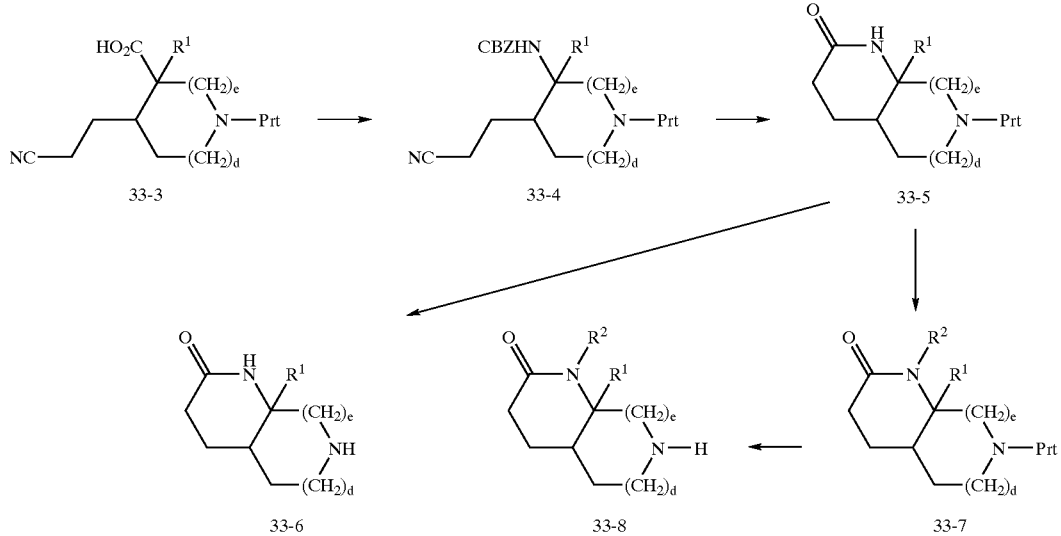

Intermediate nitriles of formula 33-2 can be prepared by homologating 12-2 (R is an alkyl group), analogous to the ketone homologation described in Scheme 23. Conversion of ester 33-2 to carbamates of formula 33-4 can be accomplished as described above (see Scheme 11). Alcoholysis of the cyano group of 33-4 as described above (see Scheme 22) and removal of the CBZ protecting group, followed by cyclization of the amine with the adjacent ester group produces a lactam of formula 33-5. Deprotection of 33-5 gives the lactam of formula 33-6.

Alternatively, alkylation of 33-5 in the usual fashion (see Scheme 11) gives 33-7, which can be deprotected to give 33-8. One skilled in the art will recognize that an $R^{1A}$ substituent may be introduced by alkylating aldehyde 12-2. An $R^9$ substitutuent may be introduced by conjugate addition to the unsaturated nitrile (33-1). $R^9$, $R^{10}$ substitution can be introduced next to the lactam by alkylation of 33-7.

SCHEME 34

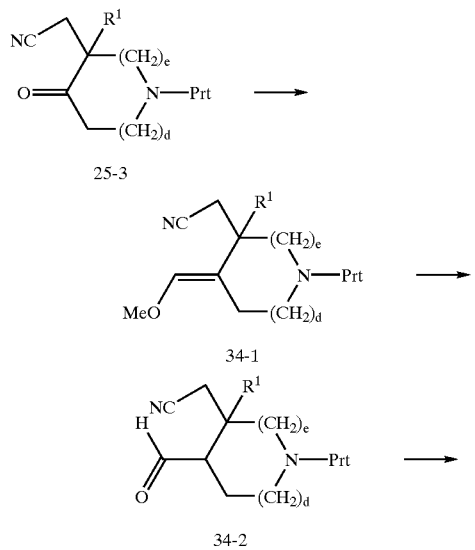

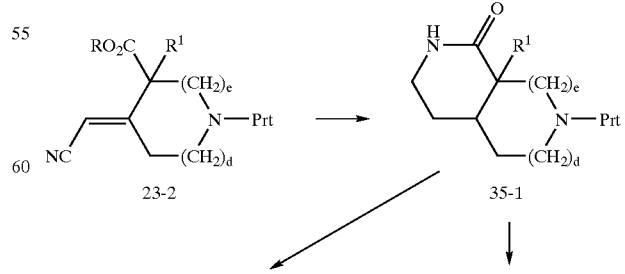

The homologation of 25-3 to give a lactam of formula 34-5 can be analogously performed according to the procedures described in Scheme 21. One skilled in the art will recognize that an $R^{1A}$ substituent may be introduced by alkylating 34-4 (R is an alkyl group). $R^9$, $R^{10}$ substitution may be introduced by alkylating nitrile 34-1.

SCHEME 35

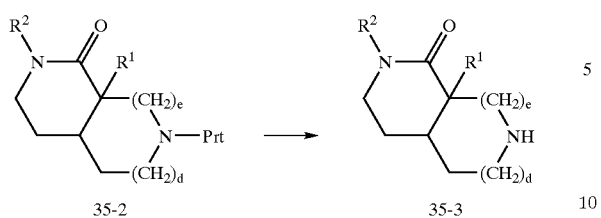

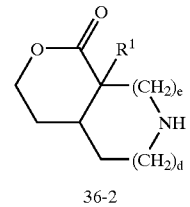

As illustrated in Scheme 35, catalytic hydrogenation of a nitrile of formula 23-2 (R is an alkyl group) gives an amine, followed by cyclization of the amine with the adjacent ester group to give lactams of formula 35-1. Deprotection of 35-1 gives 35-3, $R^2$ is H. Alternatively, alkylation of lactam 35-1 as described above (see Scheme 11) provides N-substituted amides of formula 35-2. Deprotection of 35-2 affords 35-3. One skilled in the art will recognize that an $R^{1A}$ substituent may be introduced by conjugate addition to the unsaturated nitrile.

As illustrated in Scheme 36, selective reduction of the carboxylic acid group of 11-5 to an alcohol, such as by treating 11-5 (R is an alkyl group) with borane in a suitable solvent, followed by cyclization of the alcohol and ester produces a lactone of the formula 36-1. Deprotection of 36-1 then gives 36-2.

SCHEME 37

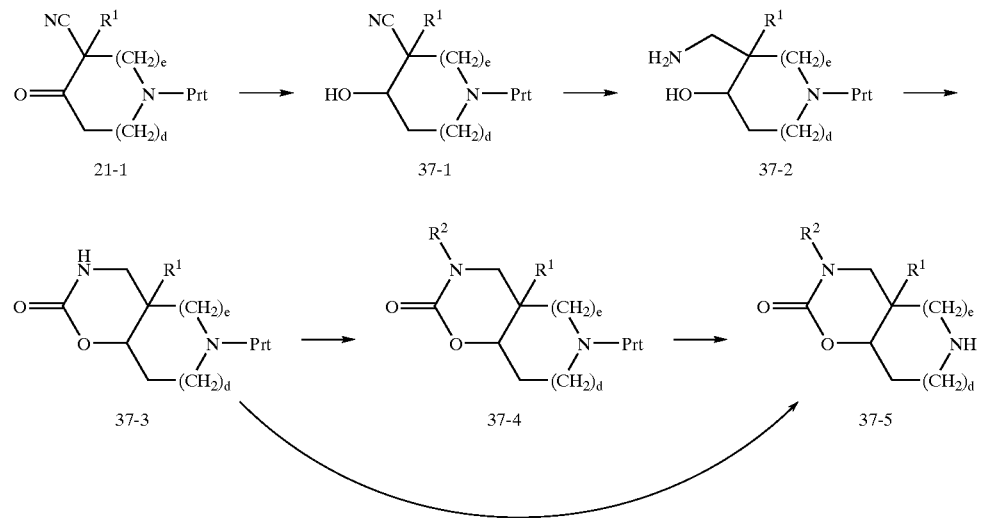

Intermediate alcohols of formula 37-1 can be prepared by reducing the ketone of 21-1, such as with sodium borohydride in a solvent such as methanol at a temperature of about 0° C. Reduction of the cyano group to an amine, such as by catalytic hydrogenation, affords aminoalcohol 37-2. Treating 37-2 with a reagent like CDI or other phosgene equivalent in the presence of a base like TEA (see Scheme 14) produces a cyclized carbamate of formula 37-3. Deprotection of 37-3 then gives 37-5, $R^2$ is H. Alternatively, 37-3 may be alkylated as described above (see Scheme 13) to give an N-substituted carbamate of formula 37-4, which is deprotected to give 37-5. One skilled in the art will recognize that an $R^{1A}$ substituent may be introduced by addition to ketone 21-1.

SCHEME 36

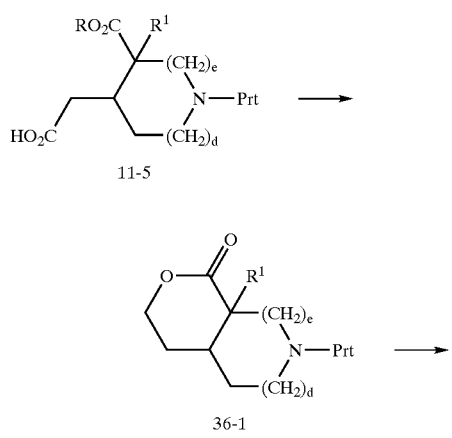

SCHEME 38

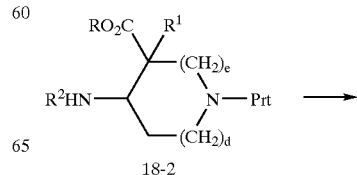

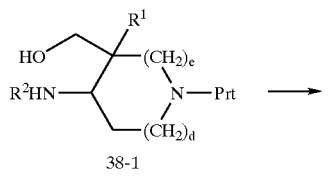

38-1

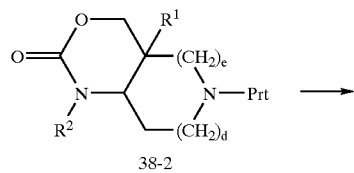

38-2

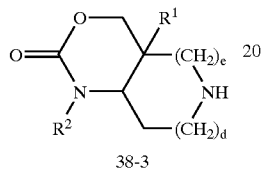

38-3

Intermediate aminoalcohols of formula 38-1 can be prepared by reducing an ester of formula 18-2 (R is an alkyl group), such as with lithium borohydride. Treating 38-1 with a phosgene equivalent as described in Scheme 14 produces a cyclized carbamate of formula 38-2. Deprotection subsequently provides 38-3.

Intermediate imines of formula 39-1 can be prepared by condensing the ketone of 21-1 with a primary amine under dehydrating conditions, such as azeotropic distillation using a solvent like benzene. Catalytic hydrogenation to reduce the nitrile and imine converts 39-1 to 39-2. Treating 39-2 with a reagent like CDI, phosgene, or triphosgene in the presence of a base like TEA produces the cyclized and N-substituted ureas of formula 39-3. Deprotection of this material provides 39-5 where the $R^2$ attached to the (2)-nitrogen is H. Alkylation of 39-3, such as with sodium hydride and an alkyl halide produces the N,N'-substituted ureas of formula 39-4, which can be deprotected to provide 39-5 where the $R^2$ attached to the (2)-nitrogen is an alkyl group.

SCHEME 39

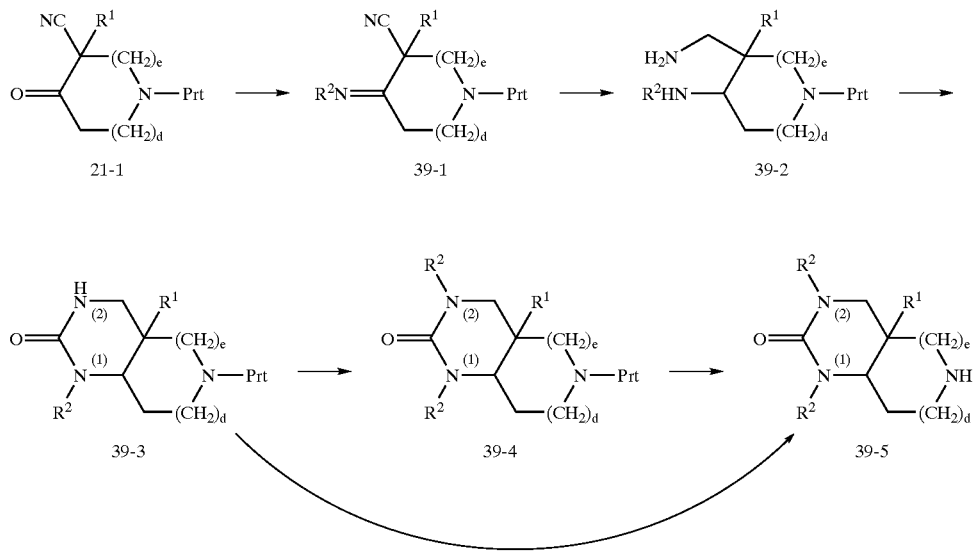

SCHEME 40

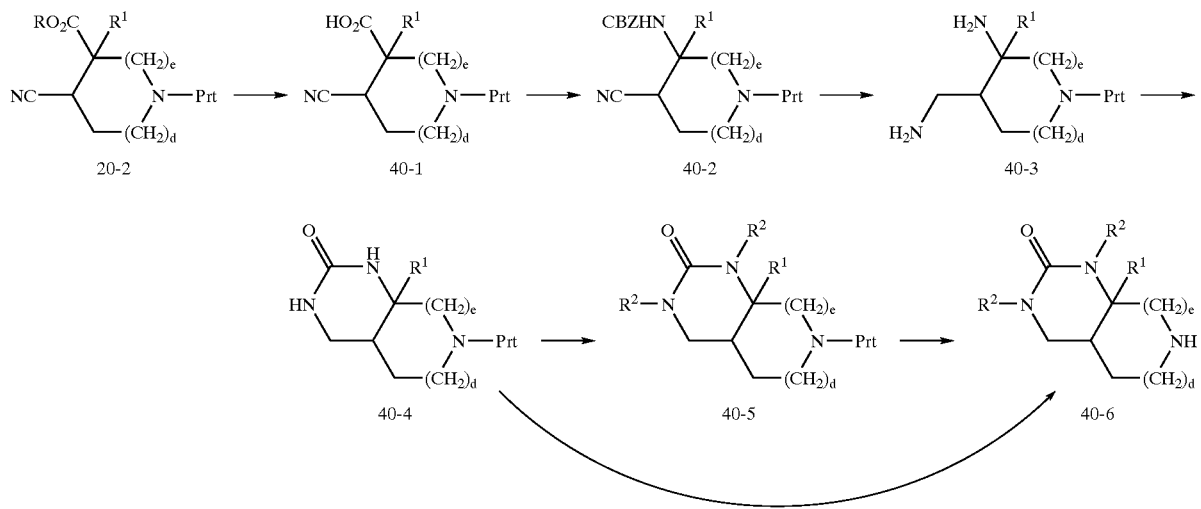

As illustrated in Scheme 40, ester 20-2 (R is an alkyl group) can be converted to carbamate 40-2 as described above (see Scheme 11). Catalytic hydrogenation of 40-2 will reduce the nitrile and cleave the CBZ group to provide a diamine of formula 40-3. Acylating 40-3 with a reagent such as CDI, phosgene, or triphosgene in the presence of a base like TEA produces the cyclized ureas of formula 40-4. Deprotection at this stage provides 40-6 where each $R^2$ is H. Alternatively, alkylation of 40-4, such as by deprotonation with a strong base like sodium hydride followed by reaction with an alkylating reagent like an alkyl halide, tosylate or mesylate produces the N,N'-substituted ureas of formula 40-5. Deprotection then provides 40-6 where each $R^2$ is alkyl. One skilled in the art will recognize that an $R^{1A}$ substituent may be introduced by alkylation of nitrile 20-2.

Intermediate esters of formula 41-1 (R is an alkyl group) can be prepared by alcoholysis of the cyano group in 40-2 with ethanolic HCl. Reducing the ester group in 41-1, such as with lithium borohydride in THF produces an alcohol of formula 41-2. Catalytic hydrogenation to remove the CBZ group to yield an amine as previously described converts 41-2 to 41-3. Treating 41-3 with a reagent like CDI or other phosgene equivalent in the presence of a base like TEA produces a carbamate of formula 41-4. Deprotection at this stage provides 41-6 where $R^2$ is H. Alternatively, transformation of 41-4 to N-substituted carbamates of formula 41-5 can be achieved by deprotonating 41-4 with a stong base such as sodium hydride in a solvent like DMF, followed by alkylation with a reagent such as an alkyl halide, tosylate or mesylate. Deprotection then converts 41-5 to 41-6 where $R^2$ is alkyl.

SCHEME 41

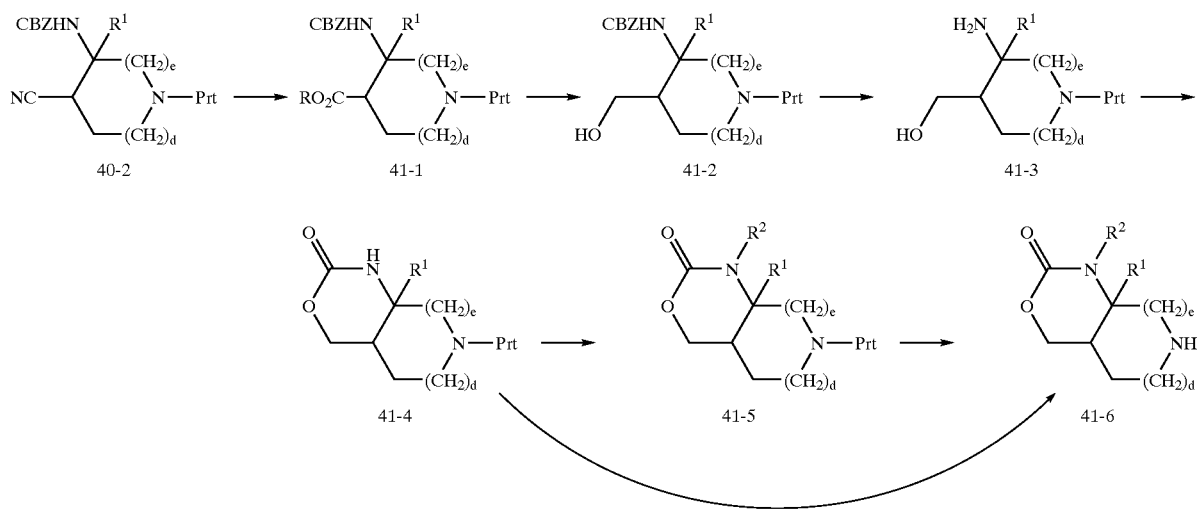

SCHEME 42

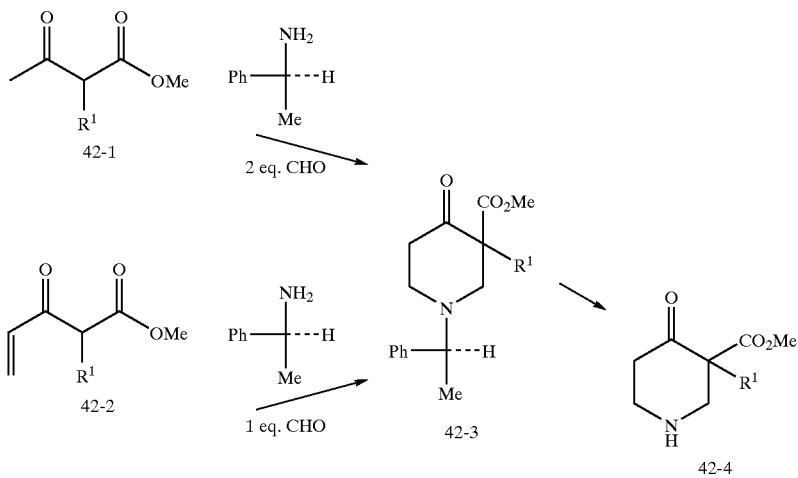

Reaction of a ketoester of formula 42-1 with a chiral amine such as alpha-methylbenzylamine with a suitable aldehyde such as formaldehyde, or reaction of a vinyl ketoester of formula 42-2 with a chiral amine such as alpha-methylbenzylamine with a suitable aldehyde such as formaldehyde, affords a compound of formula 42-3 via a double Mannich reaction. Compound 42-3 is equivalent to 11-1 where d and e are 1, and may be deprotected with a suitable catalyst such as palladium in the presence of hydrogen to give 42-4. In addition, 42-3 could be isolated as a single diastereomer (by selective cyclization or separation of diastereomers), thereby providing 42-4 as a single enantiomer.

SCHEME 43

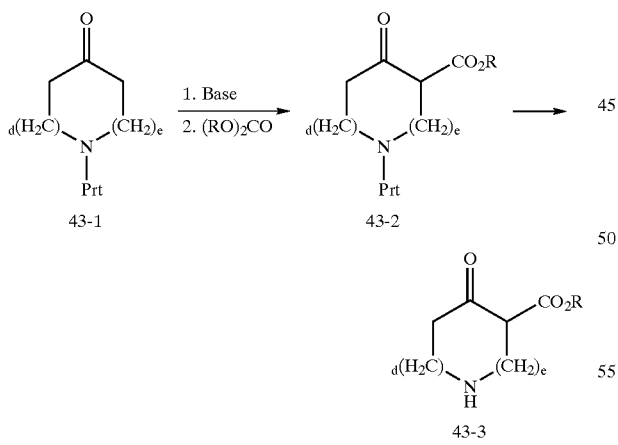

Treatment of a compound of formula 43-1 with a base such as sodium hydride in a solvent such as DMF followed by treatment with diethylcarbonate generates the ethyl ester of compound 43-2 (R is an alkyl group). Deprotection of the amine transforms 43-2 into 43-3. It will be recognized by one skilled in the art that 19-1 is equivalent to 43-3.

SCHEME 44

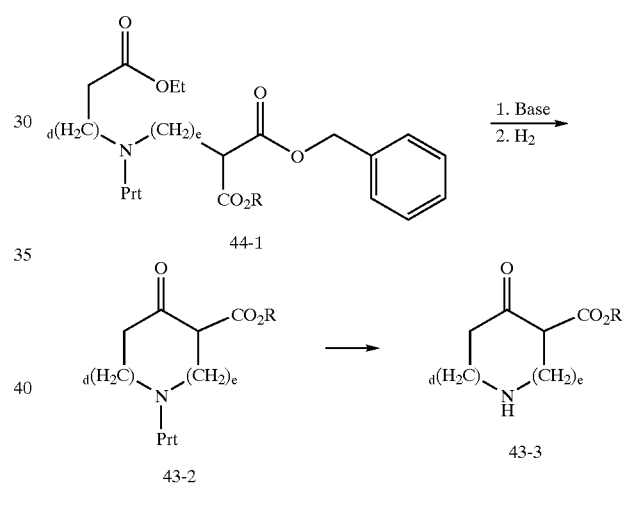

Treatment of a malonic ester of formula 44-1 (R is an alkyl group) with a base such as sodium hydride in a solvent such as DMF and subsequent hydrogenolysis of the benzyl group with hydrogen and a catalyst such as palladium in a suitable solvent such as methanol produces the ester of formula 43-2. Deprotection of the amine generates compounds of formula 43-3. It will be recognized by one skilled in the art that 19-1 is equivalent to 43-3.

SCHEME 45

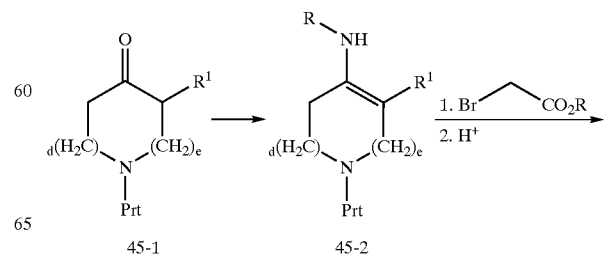

-continued

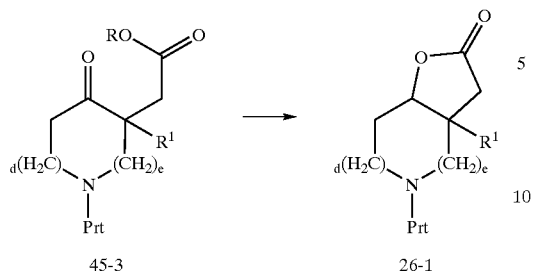

45-3 → 26-1

Treatment of a ketone of formula 45-1 with a secondary amine such as piperidine in a suitable solvent such as benzene with removal of water affords an enamine of formula 45-2 (each R is an alkyl group). Alkylation of the enamine with an alpha-haloester such as ethylbromoacetate in a suitable solvent such as benzene or THF using a suitable base such as LDA or NaN(SiMe$_3$)$_2$ affords a ketoester of formula 45-3. Reduction with a mild reducing agent such as sodium borohydride in methanol and subsequent cyclization then affords 26-1.

SCHEME 46

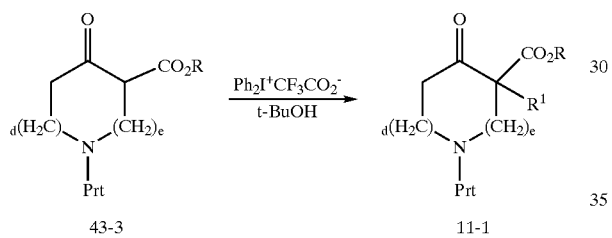

43-3 → 11-1

Treatment of a ketoester of formula 43-3 (R is an alkyl group) with an iodonium salt such as diphenyliodonium trifluoroacetate in a suitable solvent such as t-butanol generates a ketoester of formula 11-1 where $R^1$ is phenyl. See Synthesis, (9), 1984 p. 709 for a detailed description.

SCHEME 47

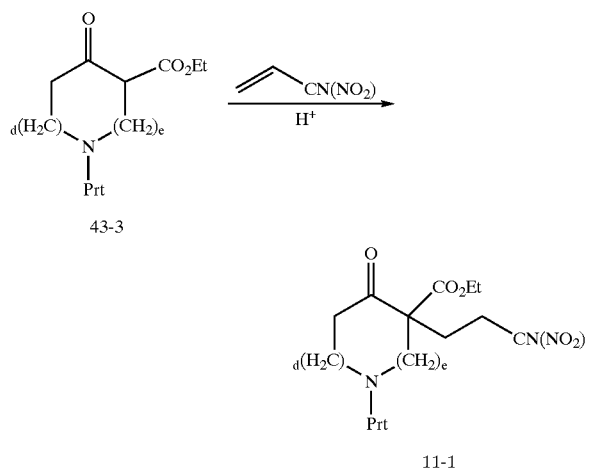

43-3 → 11-1

Treatment of a ketoester of formula 43-3 with an olefin such as acrylonitrile or nitroethylene generates a ketoester of formula 11-1 where $R^1$ is $CH_2CH_2CN$ or $R^1$ is $CH_2CH_2NO_2$.

SCHEME 48

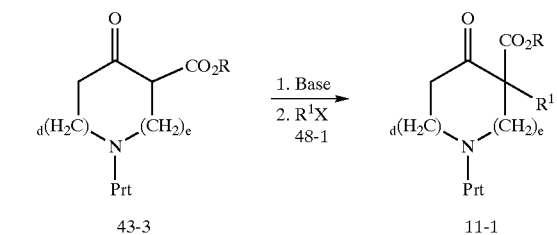

43-3 → 11-1

Treatment of an ester of formula 43-3 (R is an alkyl group) with a base such as sodium hydride in a solvent such as DMF followed by an alkyl halide 48-1 generates a compound of formula 11-1 as illustrated in Scheme 48.

SCHEME 49

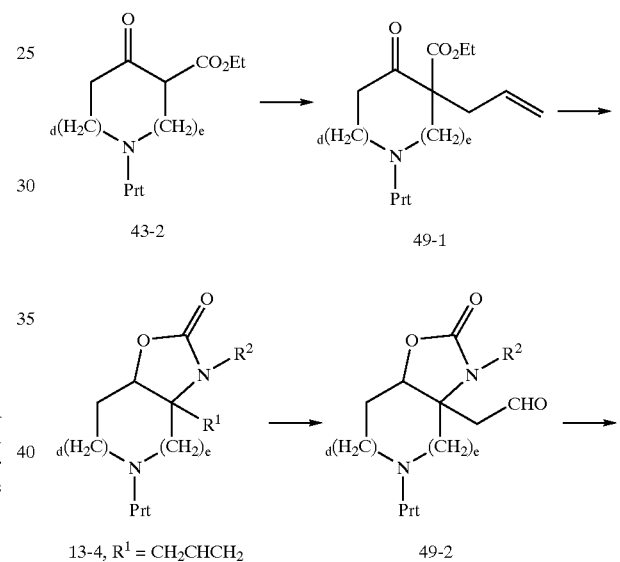

43-2 → 49-1

13-4, $R^1 = CH_2CHCH_2$ → 49-2

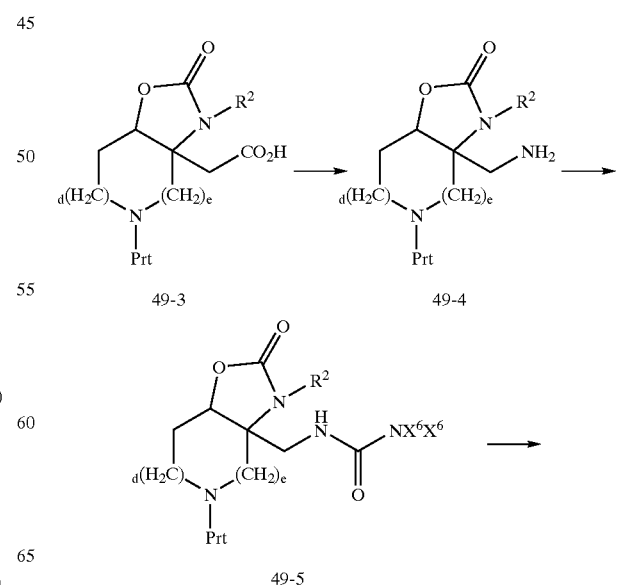

49-3 → 49-4

49-5

61

-continued

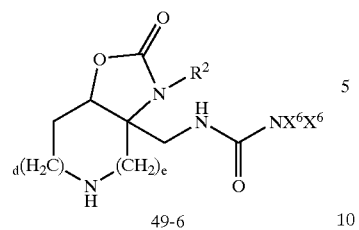

49-6

Treatment of a ketoester of formula 43-2 with allyl bromide and a suitable base such as sodium hydride in a suitable solvent such as DMF affords a ketoester of formula 49-1 (11-1, $R^2$ is allyl). Compound 49-1 may then be converted to 12-4 as described in Scheme 13. Ozonolysis of 13-4 in a suitable solvent such as methylene chloride followed by treatment with a reducing agent such as dimethylsulfide affords an aldehyde of formula 49-2. Oxidation of 49-2 affords a carboxylic acid of formula 49-3. Curtius rearrangement of 49-3, followed by hydrolysis of the intermediate isocyanate affords a primary amine of formula 49-4. Treatment of a compound of formula 49-4 with an isocyanate or carbamate affords a urea of formula 49-5. Deprotection of the nitrogen affords compounds of formula 49-6 (13-5, $R^1$ is $CH_2NHCONX^6X^6$). Those skilled in the art will recognize that other heterocycles, prepared in previous schemes, could be transformed analogously to the conversion of 13-4 to 49-6.

SCHEME 50

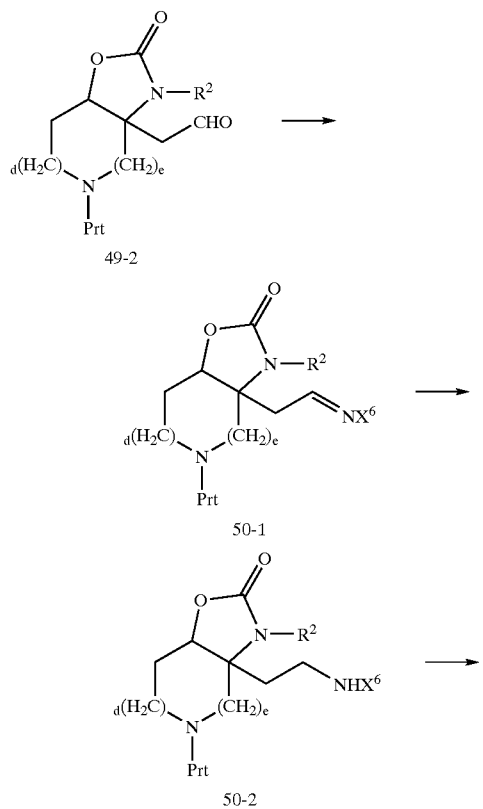

62

-continued

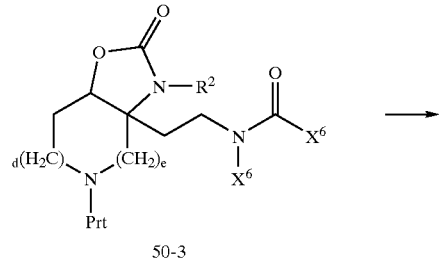

50-3

50-4

Treatment of a compound of formula 49-2 with a primary amine of formula $HZNX^6$ affords an imine of formula 50-1. Reduction of a compound of formula 50-1 affords a compound of formula 50-2. Treatment of a compound of formula 50-2 with an acylating agent affords a compound of formula 50-3. Deprotection of the nitrogen affords compounds of formula 50-4 (13-5, $R^1$ is $CH_2CH_2NX^6COX^6$). Those skilled in the art will recognize that other heterocycles, prepared in previous schemes, could be transformed in a manner analogous to the conversion of 49-2 to 50-4.

SCHEME 51

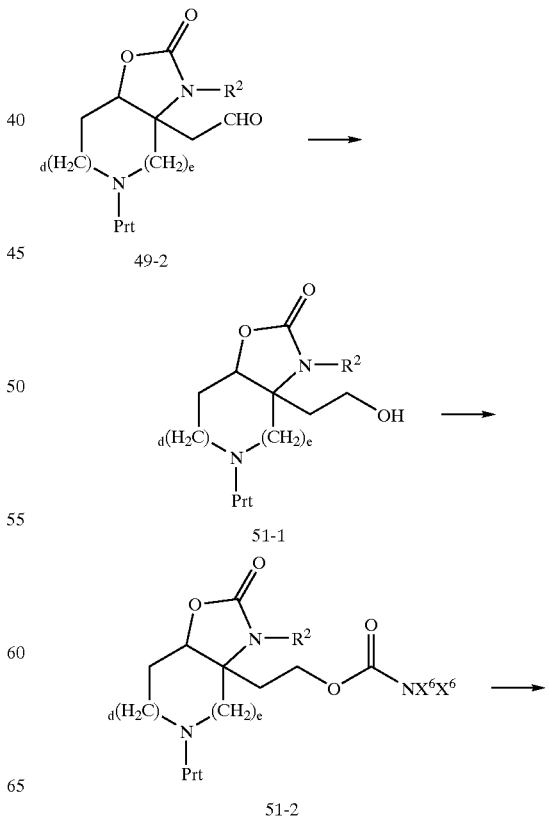

-continued

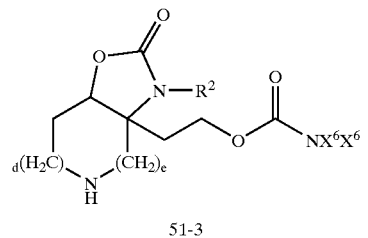

51-3

Treatment of a compound of formula 49-2 with a reducing agent such as sodium borohydride affords a compound of formula 51-1. Reaction of 51-1 with an acylating agent such as an isocyanate or carbamate affords compounds of formula 51-2. Deprotection of the nitrogen affords compounds of formula 51-3. Those skilled in the art will recognize that other heterocycles, prepared in previous schemes, could be transformed in a manner analogous to the conversion of 49-2 to 51-3.

SCHEME 52

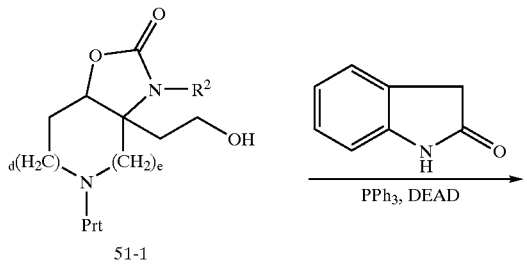

52-1

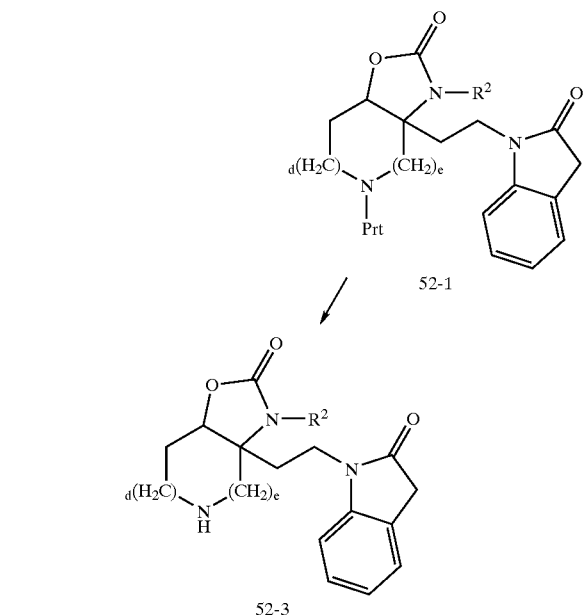

52-3

Treatment of a compound of formula 51-1 with a phosphine such as triphenyl phosphine and an azo compound such as diethylazodicarboxylate and an oxindole affords a compound of formula 52-1. Deprotection of the nitrogen affords the compound of formula 52-3. Those skilled in the art will recognize that other heterocycles, prepared in previous schemes, could be transformed in a manner analogous to the conversion of 49-2 to 52-3.

SCHEME 53

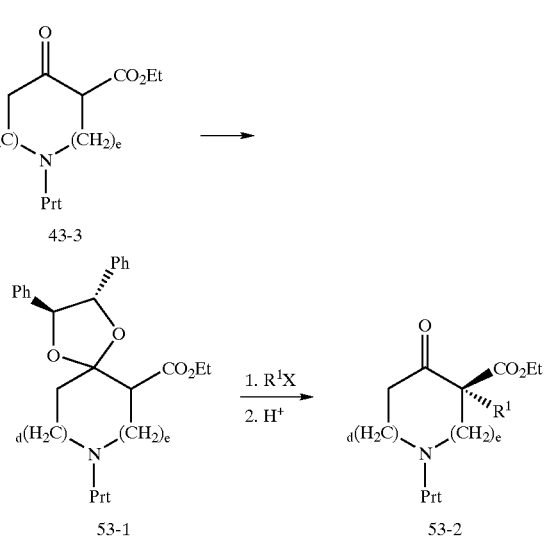

Treatment of a ketoester of formula 43-3 with a chiral diol and acid catalyst with removal of water in a suitable solvent such as benzene affords a chiral ketal like formula 53-1. Alkylation of 53-1 with an alkyl halide in the presence of a base such as LDA followed by acid-catalyzed hydrolysis of the ketal affords chiral ketoesters of formula 53-2. Ketoester 53-2 is a single enantiomer of 11-1 and may be homologated in a similar fashion to give various heterocycles.

SCHEME 54

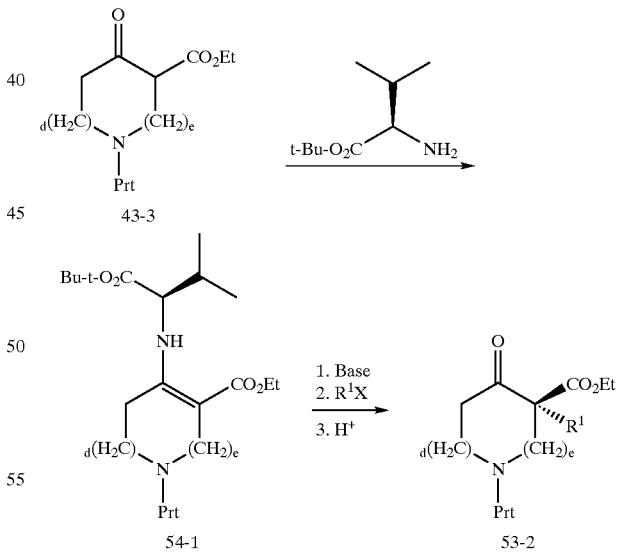

Treatment of a ketoester of formula 43-3 with a chiral amino acid ester such as valine t-butyl ester affords a chiral enamine of formula 54-1. Alkylation of 54-1 with an alkyl halide in the presence of a base such as LDA followed by acid-catalyzed hydrolysis of the enamine affords chiral ketoesters of formula 53-2.

SCHEME 55

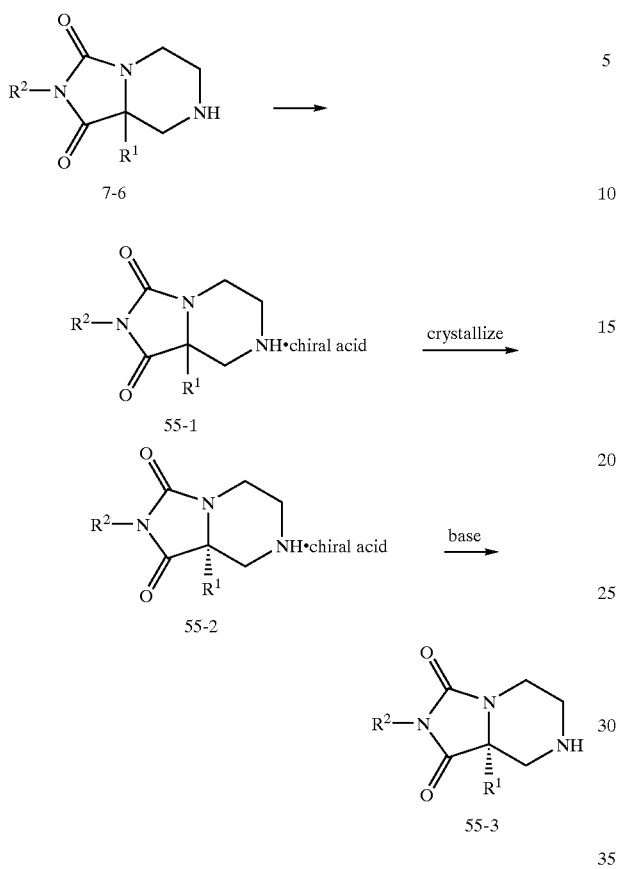

Salt formation of 7-6 with a chiral acid affords a mixture of diastereomeric salts of formula 55-1. Crystallization of the diastereomeric salts affords the acid salt of chiral compounds of formula 55-2. Decomposition of the salt 55-2 with base liberates chiral compounds of formula 55-3. This resolution scheme could be applied to the resolution of other HET-bicyclic compounds described above.

SCHEME 56

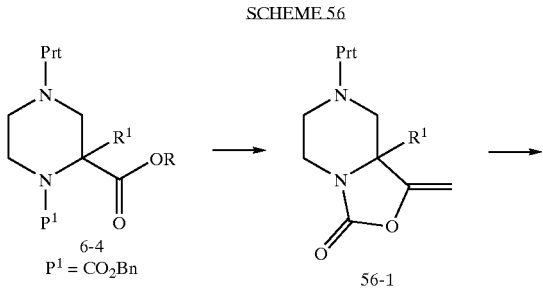

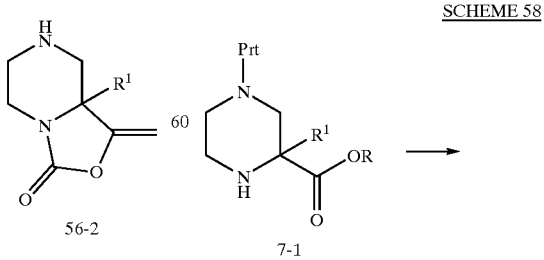

As illustrated in Scheme 56, treatment of 6-4 ($P^1$ is $CO_2Bn$) with an alkyl metal reagent like methyl magnesium bromide affords 56-1. Deprotection as usual then affords 56-2.

SCHEME 57

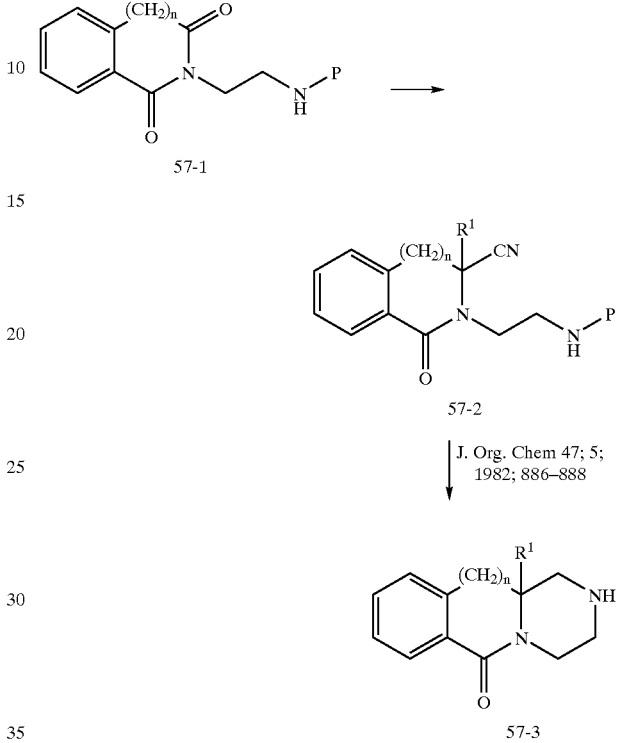

Compounds of formula 57-3 can be prepared from known phthalic or homophthalic anhydrides by methods previously described by Welch, Willard M. (J.Org.Chem 47; 5; 1982; 886–888. J.Org.Chem.; 47; 5; 1982; 886–888) or Machida, Minoru et al. (Heterocycles; 14; 9; 1980; 1255–1258). Alternatively, the analogous phthalimides or homophthalimides of formula 57-1 can be treated with the appropriate hydride reagent (e.g., $NaBH_4$) or organometallic reagent (e.g., methyl Grignard), followed by treatment with sodium or potassium cyanide to produce an intermediate of the formula 57-2. Compounds of formula 57-2 can be converted to compounds of formula 57-3 as previously described by Welch, Willard M. (J.Org.Chem 47; 5; 1982; 886–888).

SCHEME 58

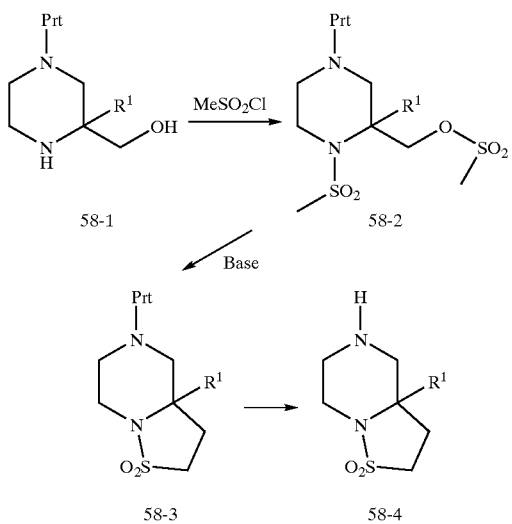

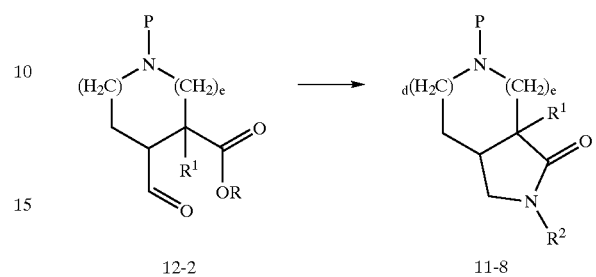

As illustrated in Scheme 58, intermediates of formula 58-4 can be prepared in four steps from compounds of formula 7-1. Compounds of formula 7-1 are treated with a suitable reducing agent such as Super Hydride® in a suitable solvent, preferably THF at a temperature of −20 to 50° C., preferably at around 25° C. to give compounds of formula 58-1. Amino alcohols of formula 58-1 are then treated with at least two equivalents of methanesulfonyl chloride and at least two equivalents of a suitable base, preferably pyridine in a suitable solvent, preferably pyridine at a temperature of −20 to 50° C. preferably around 25° C. to give intermediates of formula 58-2. Treatment of 58-2 with a strong base, preferably sec-butyllithium at a temperature of around −78° C. followed by warming to a temperature of around 25° C. affords intermediates of formula 58-3. Removal of the protecting group as described above, transforms 58-3 into 58-4.

An alternative synthesis of lactam 11-8 is illustrated in Scheme 59. An aldehyde of formula 12-2 can be employed in a reductive amination with an amine and reducing agent, for example sodium triacetoxyborohydride. Subsequent cyclization of the amine with the adjacent ester group affords 11-8. One skilled in the art will recognize that an $R^{1A}$ substituent could have been introduced adjacent to the aldehyde by alkylating aldehyde 12-2 according to well known procedures.

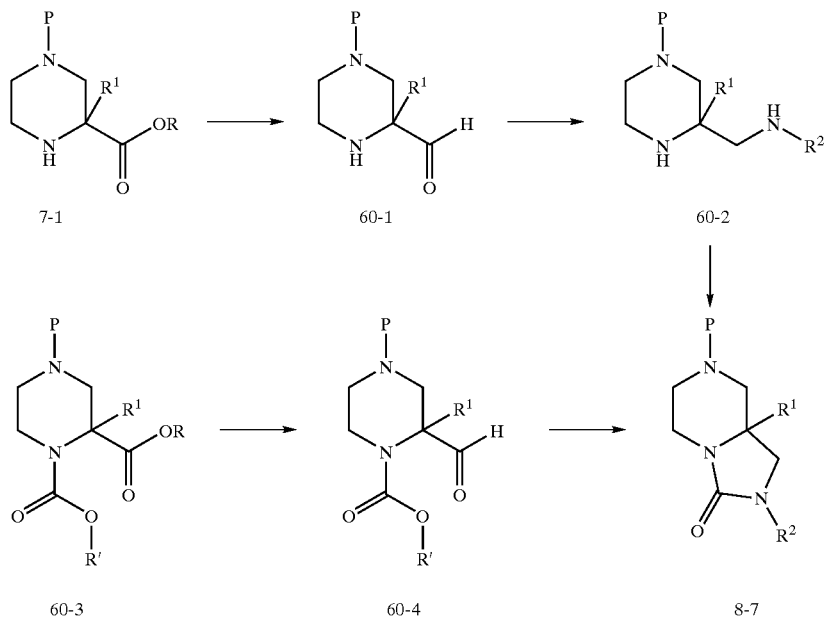

Aldehydes of formula 60-1 can be prepared by reducing 7-1 with an agent like diisobutylaluminum hydride at a suitable temperature, preferably −78° C. to 0° C. in a suitable solvent, such as THF, methylene chloride, toluene or ether. This aldehyde may then be converted to amines of the formula 60-2 by the methods described in Scheme 8 to convert 8-3 to 8-5. In addition, an oxime may be formed by treating the aldehyde with hydroxylamine hydrochloride. Reduction of this oxime, such as with Raney-nickel provides 60-2 where $R^2$ is hydrogen. Treatment of this material with phosgene, triphosgene, carbonyl diimidazole, or other equivalent in the presence of a base, preferably a tertiary amine base, provides a route to ureas of formula 8-7. Those skilled in the art will recognize that $R^2$ may have been a group, such as a benzyl or allyl group, which could be cleaved to give 8-7 where $R^2$ is hydrogen.

Alternatively, compounds of the formula 8-7 may be prepared by reducing carbamate protected ester 60-3, for example when $R^1=CH_2$-2-Pyr, according to well known reduction techniques to afford aldehyde 60-4 which may then be converted to an amine, as described above, which is then reacted with the carbamate at a suitable temperature to provide 8-7.

conditions, such as by treating 61-3 with a strong base, e.g., lithium diisopropylamide or LHMDS in a reaction inert solvent such as THF at a suitable temperature, preferably −78° C. The anion generated is treated with alkylating reagents such as alkyl halides or alkyl tosylates, such as methyl iodide, to give 61-4. This process may be repeated to introduce a second substituent. Deprotection affords compounds of formula 61-5. Those skilled in the art will recognize that a $R^9$ substituent can be introduced β to the lactam by conjugate addition to 61-1, such as would be afforded by the use of an alkyl cuprate reagent.

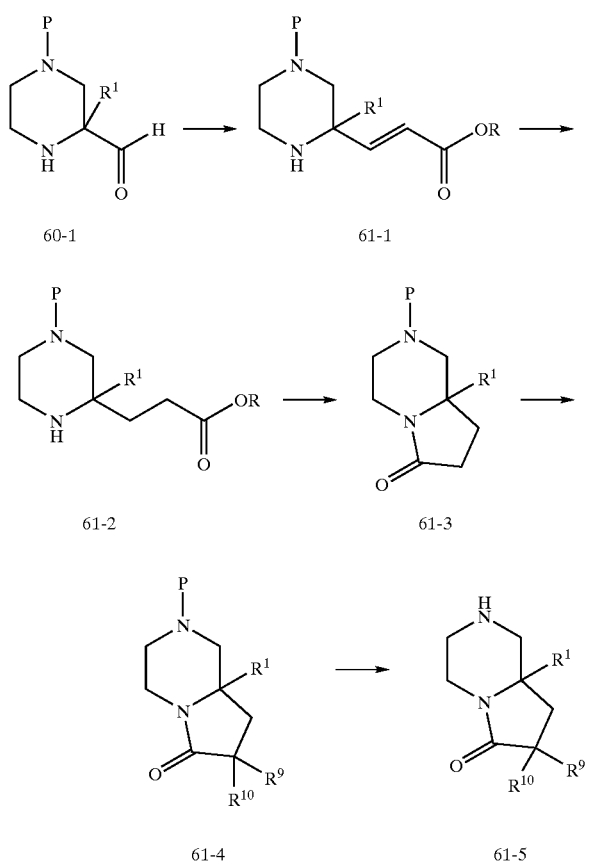

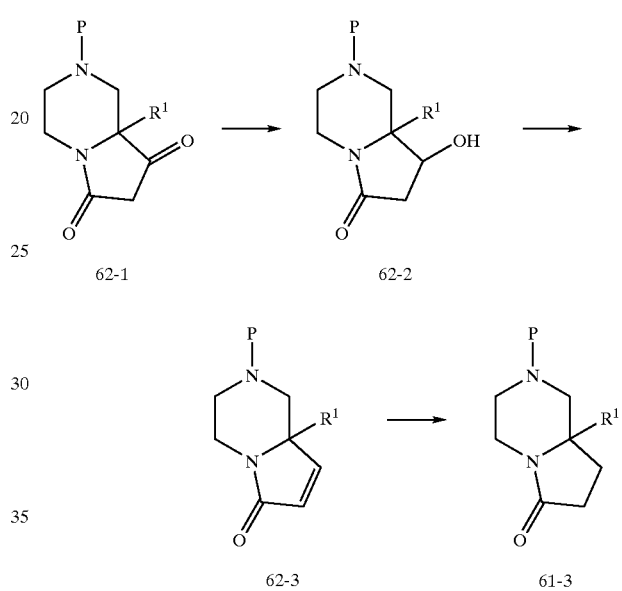

An alternate synthesis of 61-3 is shown above. Reduction of ketoamide 62-1, which is equivalent to 10-2 where $R^9$ and $R^{10}$ are hydrogen, with a reducing agent such sodium borohydride, in an reaction inert solvent such as methanol at a suitable temperature such as 0° C. affords alcohol 62-2. The alcohol is reacted under standard elimination conditions well known to those skilled in the art to provide unsaturated lactam 61-3. Suitable elimination conditions include activating the alcohol, such as by converting it to the corresponding tosylate or mesylate, and then treating the activated alcohol with base at a suitable temperature, for instance with 1,8-diazabicyclo[5.4.0]undec-7-ene in refluxing toluene, or by deprotonating the amide with a strong base such as LHMDS. The alcohol may also be eliminated at suitable temperatures in the presence of a strong base or strong acid. Those skilled in the art will recognize that these conditions may also cleave the protecting group (P). Reduction of 62-3, by methods such as catalytic hydrogenation (see Scheme 11) or conjugate reduction with an agent such as the alkali metal salt of a trialklyborohydride, like lithium tri-sec-butylborohydride, will then provide 61-3. Those skilled in the art will recognize that a $R^9$ substituent could have been introduced β to the lactam by conjugate addition of a reagent, such as a cuprate, to the unsaturated lactam.

Olefin 61-1 may be prepared by olefinating aldehyde 60-1 with a reagent such as the anion generated upon treating a trialkylphosphono acetate with an appropriate base, such as NaHMDS in a suitable solvent, such as THF. Reduction of the olefin, by methods such as catalytic hydrogenation (see Scheme 11) or conjugate reduction with an agent such as the alkali metal salt of a trialkylborohydride, such as lithium tri-sec-butylborohydride, provides the compounds of formula 61-2. This material is cyclized at elevated temperatures in a reaction inert solvent using cyclization conditions well known to those skilled in the art. Those skilled in the art will recognize that the cyclization reaction may require the addition of a base such as potassium carbonate. Generally the reaction is carried out at reflux in a solvent such as methanol. Deprotection of 61-3 affords compounds of formula 61-5 where $R^9$ and $R^{10}=H$. Those skilled in the art will recognize that 61-3 can be alkylated under a variety of

SCHEME 63

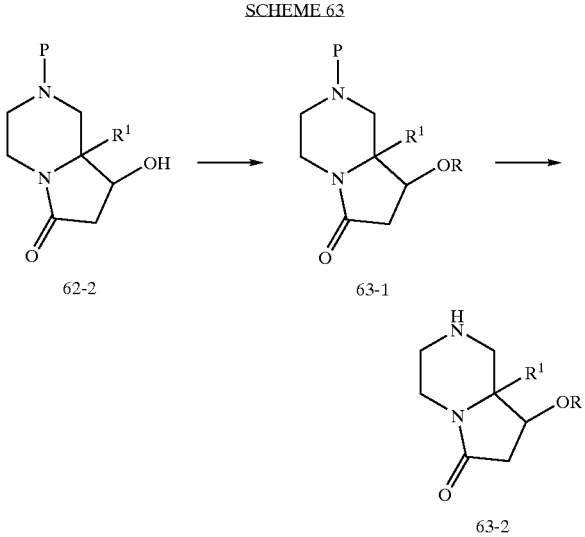

Compounds of formula 63-1 are prepared by deprotonating the alcohol with a strong base such as sodium hydride, LHMDS, KHMS or NaHMDS in a suitable solvent such as DMF or THF followed by treatment with an alkylating agent such as an alkyl halide, mesylate or tosylate, for instance, methyl iodide. The product is then deprotected according to methods well known to those skilled in the art to provide 63-2.

2-Amino-N-(1(R)-benzyloxymethyl-2-(1,3-dioxo-8a(S)-pyridin-2-ylmethyl-2-(2,2,2-trifluoro-ethyl)-hexahydro-imidazo[1,5-a]pyrazin-7-yl)-2-oxo-ethyl)-2-methyl-propionamide, having the following structure:

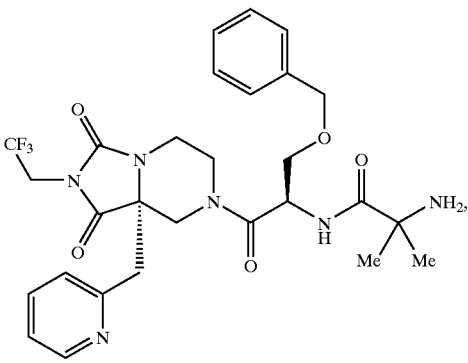

is within the scope of the disclosure of U.S. Provisional Application No. 60/050764 and may be prepared as described in Examples Five and Six.

The expression "prodrug" refers to compounds that are drug precursors which, following administration, release the drug in vivo via some chemical or physiological process (e.g., a prodrug on being brought to the physiological pH is converted to the desired drug form). A prodrug of the compounds of formula I or a prodrug of the compounds of formula IV, or a prodrug of both, may be used in the methods and compositions of the instant invention. Exemplary prodrugs upon cleavage release the corresponding free acid, and such hydrolyzable ester-forming residues of the compounds of this invention include but are not limited to carboxylic acid substituents (e.g., when $R^1$ of formula IV is —$(CH_2)_q$C(O)O$X^6$ where $X^6$ is hydrogen, or when $R^2$ or $A^1$ of formula IV contains carboxylic acid) wherein the free hydrogen is replaced by ($C_1$–$C_4$)alkyl, ($C_2$–$C_{12}$) alkanoyloxymethyl, ($C_4$–$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di($C_1$–$C_2$)alkylcarbamoyl-($C_1$–$C_2$)alkyl and piperidino-, pyrrolidino- or morpholino($C_2$–$C_3$)alkyl.

Other exemplary prodrugs are derivatives of an alcohol of the active compounds used in this invention wherein the free hydrogen of the hydroxyl substituent (e.g., when $R^1$ of formula IV contains hydroxyl) is replaced by ($C_1$–$C_6$) alkanoyloxymethyl, 1-(($C_1$–$C_6$)alkanoyloxy)ethyl, 1-methyl-1-(($C_1$–$C_6$)alkanoyloxy)ethyl, ($C_1$–$C_6$) alkoxycarbonyloxymethyl, N-($C_1$–$C_6$) alkoxycarbonylamino-methyl, succinoyl, ($C_1$–$C_6$)alkanoyl, α-amino($C_1$–$C_4$)alkanoyl, arylacetyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O ($C_1$–$C_6$)alkyl)$_2$ or glycosyl (the radical resulting from detachment of the hydroxyl of the hemiacetal of a carbohydrate).

Prodrugs of this invention where a carboxyl group in a carboxylic acid of the active compounds used in this invention is replaced by an ester may be prepared by combining the carboxylic acid with the appropriate alkyl halide in the presence of a base such as potassium carbonate in an inert solvent such as DMF at a temperature of about 0° C. to 100° C. for about 1 to about 24 hours. Alternatively, the acid is combined with the appropriate alcohol as solvent in the presence of a catalytic amount of acid such as concentrated sulfuric acid at a temperature of about 20° C. to 120° C., preferably at reflux, for about 1 hour to about 24 hours. Another method is the reaction of the acid in an inert solvent such as THF, with concomitant removal of the water being produced by physical (e.g., Dean Stark trap) or chemical (e.g., molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as DMF at a temperature of about 0° C. to 100° C. for about 1 to about 24 hours. Alkanoylaminomethyl ethers may be obtained by reaction of the alcohol with a bis-(alkanoylamino)methane in the presence of a catalytic amount of acid in an inert solvent such as THF, according to a method described in U.S. Pat. No. 4,997,984. Alternatively, these compounds may be prepared by the methods described by Hoffman et al. in J. Org. Chem. 1994, 59, p. 3530.

In the above structural formulas and throughout the instant application, the following terms have the indicated meanings unless expressly stated otherwise:

The alkyl groups are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, ethynyl, propenyl, butadienyl, hexenyl and the like.

When the definition $C_0$-alkyl occurs in the definition, it means a single covalent bond.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, 2-propynyloxy, isobutenyloxy, hexenyloxy and the like.

The term "halogen" or "halo" is intended to include the halogen atoms fluorine, chlorine, bromine and iodine.

The term "halogenated alkyl" is intended to include an alkyl group as defined hereinabove substituted by one or more halogen atoms as defined hereinabove.

The term "halogenated cycloalkyl" is intended to include a cycloalkyl group substituted by one or more halogen atoms as defined hereinabove.

The term "aryl" is intended to include phenyl and naphthyl and aromatic 5- and 6-membered rings with 1 to 4 heteroatoms or fused 5- and/or 6-membered bicyclic rings with 1 to 4 heteroatoms of nitrogen, sulfur or oxygen. Examples of such heterocyclic aromatic rings are pyridine, thiophene (also known as thienyl), furan, benzothiophene, tetrazole, indole, N-methylindole, dihydroindole, indazole, N-formylindole, benzimidazole, thiazole, pyrimidine, and thiadiazole.

Certain of the above defined terms may occur more than once in the above formula and upon such occurrence each term shall be defined independently of the other.

Many protected amino acid derivatives are commercially available, where the protecting groups, Prt, Prt' or Prt", are, for example, BOC, CBZ, FMOC, benzyl or ethoxycarbonyl groups. Other protected amino acid derivatives can be prepared by literature methods well-known to one skilled in the art. Some substituted piperazines and piperidines are commercially available, and many other piperazines and 4-substituted piperidines are known in the literature. Various heterocyclic substituted piperidines and piperazines can be prepared following literature methods using derivatized heterocyclic intermediates. Alternatively, the heterocyclic rings of such compounds can be derivatized by standard means, such as coupling with CDI, hydrogenation of aromatic heterocycles, etc. as is well-known to those skilled in the art.

Many of the schemes illustrated above describe compounds which contain protecting groups Prt, Prt' or Prt", which can be any suitable protecting group known to those skilled in the art. Benzyloxycarbonyl groups can be removed by a number of methods including, catalytic hydrogenation with hydrogen in the presence of a palladium or platinum catalyst in a protic solvent such as methanol. Preferred catalysts are palladium hydroxide on carbon or palladium on carbon. Hydrogen pressures from 1–1000 psi can be employed; pressures from 10 to 70 psi are preferred. Alternatively, the benzyloxycarbonyl group can be removed by transfer hydrogenation.

Removal of BOC protecting groups can be carried out using a strong acid such as trifluoroacetic acid or hydrochloric acid with or without the presence of a cosolvent such as dichloromethane or methanol at a temperature of about −30° to 70° C., preferably about −5° to about 35° C.

Benzyl groups on amines can be removed by a number of methods including catalytic hydrogenation with hydrogen in the presence of a palladium catalyst in a protic solvent such as methanol. Hydrogen pressures from 1–1000 psi can be employed; pressures from 10 to 70 psi are preferred. The addition and removal of these and other protecting groups are discussed in detail by T. Greene in Protective Groups in Organic Synthesis, John Wiley & Sons, New York, 1981.

The variables shown in the above schemes are as described for compounds of Formula IV, above, unless otherwise indicated.

The compounds of formulas I and IV used in the methods and combinations of the instant invention all have at least one asymmetric center as noted, e.g., by the asterisk in the structural Formula IV-A and by the wedge-shaped bond shown in the compound of formula II. Additional asymmetric centers may be present in the compounds of Formulas I and IV depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the methods and combinations of the instant invention. In the case of the asymmetric center represented by the asterisk, it has been found that the absolute stereochemistry of the more active and thus more preferred isomer is shown in Formula IV-A.

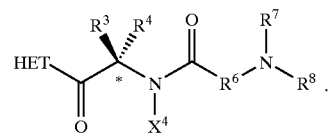

IV-A

With the $R^4$ substituent as hydrogen, the spatial configuration of the asymmetric center corresponds to that in a D-amino acid. In most cases this is also designated an R-configuration although this will vary according to the values of $R^3$ and $R^4$ used in making R- or S-stereochemical assignments.

The compounds of Formulas I and IV used in the methods and combinations of the instant invention may contain acidic moieties which are suitable for reaction with an appropriate base to form a pharmaceutically acceptable cationic salt of said compounds. The compounds of Formulas I and IV form pharmaceutically acceptable cationic salts by reacting the free carboxylic acid with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, a salt is preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The instant compounds of Formulas I and IV used in the methods and compositions of the instant invention may also contain basic moieties which are suitable for reaction with an appropriate acid to form pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. Such pharmaceutically acceptable acid addition salts are formed by taking about 1 equivalent of a free base form of a compound of Formula I or IV and reacting it with about 1 equivalent of the appropriate corresponding acid of the salt which is desired. Workup and isolation of the resulting salt is well-known to those of ordinary skill in the art.

The administration of the combinations used in the methods of this invention for purposes of stimulating the release of endogenous growth hormone can have the same effects or uses as growth hormone itself. These varied uses of growth hormone may be summarized as follows: stimulating growth hormone release in elderly humans or companion animals especially dogs, cats, cattle, camels and horses; treating growth hormone deficient adult humans or other animals especially dogs, cats, cattle, camels and horses; preventing catabolic side effects of glucocorticoids, treating osteoporosis, stimulating the immune system, accelerating wound healing, accelerating bone fracture repair, treating growth retardation, treating congestive heart failure as disclosed in PCT publications WO 95/28173 and WO 95/28174 (an example of a method for assaying growth hormone secretagogues for efficacy in treating congestive heart failure is disclosed in R. Yang et al., Circulation, Vol. 92, No. 2, p.262, 1995), treating acute or chronic renal failure or insufficiency; treating physiological short stature including growth hormone deficient children, treating short stature associated with chronic illness, treating obesity, treating growth retardation associated with Prader-Willi syndrome and Turner's syndrome; accelerating the recovery and reducing hospitalization of burn patients or following major surgery such as gastrointestinal surgery; treating intrauterine growth retardation, skeletal dysplasia, hypercortisonism and Cushing's syndrome; replacing growth hormone in stressed patients; treating osteochondrodysplasias, Noonan's syndrome, sleep disorders, Alzheimer's disease, delayed wound healing, and psychosocial deprivation; treating pulmonary dysfunction and ventilator dependency; attenuating protein catabolic response after a major operation; treating malabsorption syndromes, reducing cachexia and protein loss due to chronic illness such as cancer or AIDS; accelerating weight gain and protein accretion in patients on TPN (total parenteral nutrition); treating hyperinsulinemia including nesidioblastosis; adjuvant treatment for ovulation induction and to prevent and treat gastric and duodenal ulcers; stimulating thymic development and preventing age-related decline of thymic function; adjunctive therapy for patients on chronic hemodialysis; treating immunosuppressed patients and enhancing antibody response following vaccination; improving muscle strength, increasing muscle mass, mobility, maintenance of skin thickness, metabolic homeostasis, renal homeostasis in the frail elderly; stimulating osteoblasts, bone remodeling, and cartilage growth; treating neurological diseases such as peripheral and drug induced neuropathy, Guillian-Barre Syndrome, amyotrophic lateral sclerosis, multiple sclerosis, cerebrovascular accidents and demyelinating diseases; and stimulating wool growth in sheep.

Uses of the combinations of this invention in farm animals raised for meat production such as chickens, turkeys, sheep, pigs and cattle include stimulation of pre- and postnatal growth, enhanced feed efficiency in animals raised for meat production, improved carcass quality (increased muscle to fat ratio) (Campbell, R. G. et al., (1989), J. Anim. Sci. 67, 1265; Dave, D. J., Bane, D. P., (1990), The Compendium Food Anual, Vol. 12(1), 117; Holden, P. J., (1990), Agri-Practice, 11(3), 25; Claus, R., Weiber, U., (1994), Livestock Production Science, 37, 245; Roeder, R. et al., (1994), Growth Regulation, 4, 101); increased milk production in dairy cattle (McBride, B. W. et al., (1988), Research and Development in Agriculture 5(1), 1; McDowell, G. H. et al., (1988), Aust. J. Biol. Sci., 41, 279); improved body composition; modification of other growth hormone-dependent metabolic (Claus, R. and Weiber, U., (1994), Livestock Production Science, 37, 245) and immunologic functions such as enhancing antibody response following vaccination or improved developmental processes; and may have utility in aquaculture to accelerate growth and improve the protein-to-fat ratio in fish.

Preferred uses in companion animals include stimulating endogenous growth hormone release in companion animals such as dogs, cats and horses; treating disorders of aging (Detenbeck, L. C., Jowsey, J., Clinical Orthopedics and Related Research, July–August 1969, No. 65, pp. 76–80); stimulating thymic development and preventing age-related decline of thymic function (Goff, B. L. et al., Clinical and Experimental Immunology, 1987, 68:3, pp. 580–587; Morrison, W. B. et al., Am. J. Vet. Res., Jan. 1990, 51:1, pp. 65–70; Roth, J. A. et al., Am. J. Vet. Res., 1984, Vol. 45, pp. 1151–1155); preventing age-related decline of thymic function; preventing age-related decline in cognition; accelerating wound healing (Jacks, T. et al., Vet. Surg. 1996, 25, (5), 430); accelerating bone fracture repair (Pandey, S. K., Udupa, K. N., Indian J. Vet. Surg. 1 (2): 73–78, July 1980); stimulating osteoblasts, bone remodelling and cartilage growth (Harris, W. H. et al., Calc. Tiss. Res., 10, 1972, pp. 1–13; Heaney, R. P. et al., Calc. Tiss. Res. 10, 1972, pp. 14–22; Mankin. H. J. et al., of Bone and Joint Surgery, Vol. 60-A, #8, December 1978, pp. 1071–1075); attenuating protein catabolic response after major surgery, accelerating recovery from burn injuries and major surgeries such as gastrointestinal surgery; stimulating the immune system and enhancing antibody response following vaccination; treating congestive heart failure, treating acute or chronic renal failure or insufficiency; treating obesity; treating growth retardation, skeletal dysplasia and osteochondrodysplasias; preventing catabolic side effects of glucocorticoids; treating Cushing's syndrome; treating malabsorption syndromes, reducing cachexia and protein loss due to chronic illness such as cancer; accelerating weight gain and protein accretion in animals receiving total parenteral nutrition; providing adjuvant treatment for ovulation induction and to prevent gastrointestinal ulcers; improving muscle mass, strength and mobility; maintenance of skin thickness; and improving vital organ function and metabolic homeostasis.

Assay for Stimulation of Growth Hormone Release From Rat Pituicytes

Compositions having the ability to stimulate GH secretion from cultured rat pituitary cells are identified using the following protocol. This test is also useful for comparison to standards to determine dosage levels.

Cells are isolated from pituitaries of 6-week old male Wistar rats. Following decapitation, the anterior pituitary lobes are removed into cold, sterile Hank's balanced salt solution without calcium or magnesium (HBSS). Tissues are finely minced, then subjected to two cycles of mechanically assisted enzymatic dispersion using 10 U/mL bacterial protease (EC 3.4.24.4, Sigma P-6141, St. Louis, Mo.) in HBSS. The tissue-enzyme mixture is stirred in a spinner flask at 30 rpm in a 5% $CO_2$ atmosphere at about 37° C. for about 30 min., with manual trituration after about 15 min. and about 30 min. using a 10-mL pipet. This mixture is centrifuged at 200×g for about 5 min. Horse serum (35% final concentration) is added to the supernatant to neutralize excess protease. The pellet is resuspended in fresh protease (10 U/mL), stirred for about 30 min. more under the previous conditions, and manually triturated, ultimately through a 23-gauge needle. Again, horse serum (35% final concentration) is added, then the cells from both digests are combined, pelleted (200×g for about 15 min.), resuspended in culture medium (Dulbecco's Modified Eagle Medium (D-MEM) supplemented with 4.5 g/L glucose, 10% horse serum, 2.5% fetal bovine serum, 1% non-essential amino acids, 100 U/mL nystatin and 50 mg/mL gentamycin sulfate, Gibco, Grand Island, N.Y.) and counted. Cells are plated at 6.0–6.5×10$^4$ cells per cm$^2$ in 48-well Costar™ (Cambridge, Mass.) dishes and cultured for 3–4 days in culture medium.

Just prior to GH secretion assay, culture wells are rinsed twice with release medium, then equilibrated for about 30 minutes in release medium (D-MEM buffered with 25 mM Hepes, pH 7.4 and containing 0.5% bovine serum albumin at 37° C. ). Test compositions are dissolved in DMSO, then diluted into pre-warmed release medium. Assays are run in quadruplicate. The assay is initiated by adding 0.5 mL of release medium (with vehicle or test compound) to each culture well. Incubation is carried out at about 37° C. for about 15 minutes, then terminated by removal of the release medium, which is centrifuged at 2000×g for about 15 minutes to remove cellular material. Rat growth hormone concentrations in the supernatants are determined by a standard radioimmunoassay protocol described below.

Measurement of Rat Growth Hormone

Rat growth hormone concentrations are determined by double antibody radioimmunoassay using a rat growth hormone reference preparation (NIDDK-rGH-RP-2) and rat growth hormone antiserum raised in monkey (NIDDK-anti-rGH-S-5) obtained from Dr. A. Parlow (Harbor-UCLA Medical Center, Torrence, Calif.). Additional rat growth hormone (1.5 U/mg, #G2414, Scripps Labs, San Diego, Calif.) is iodinated to a specific activity of approximately 30 $\mu$Ci/pg by the chloramine T method for use as tracer. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation according to methods well known to those skilled in the art. This assay has a working range of 0.08–2.5 $\mu$g rat growth hormone per tube above basal levels.

Assay for Exogenously-stimulated Growth Hormone Release in the Rat After Intravenous Administration of Test Compounds Twenty-one day old female Sprague-Dawley rats (Charles River Laboratory, Wilmington, Mass.) are allowed to acclimate to local vivarium conditions (24° C., 12 hr light, 12 hr dark cycle) for approximately 1 week before testing of a combination of this invention. All rats are allowed access to water and a pelleted commercial diet (Agway Country Food, Syracuse N.Y.) ad libitum. The experiments are conducted in accordance with the NIH Guide for the Care and Use of Laboratory Animals.

On the day of the experiment, test compositions are dissolved in vehicle containing 1% ethanol, 1 mM acetic acid and 0.1% bovine serum albumin in saline. Each test is conducted in three rats. Rats are weighed and anesthetized via intraperitoneal injection of sodium pentobarbital (Nembutol®, 50 mg/kg body weight). Fourteen minutes after anesthetic administration, a blood sample is taken by nicking the tip of the tail and allowing the blood to drip into a microcentrifuge tube (baseline blood sample, approximately 100 $\mu$l). Fifteen minutes after anesthetic administration, a test composition is delivered by intravenous injection into the tail vein, with a total injection volume of 1 mL/kg body weight. Additional blood samples are taken from the tail at 5, 10 and 15 minutes after administration of a composition of this invention. Blood samples are kept on ice until serum separation by centrifugation (1430×g for 10 minutes at 10° C.). Serum is stored at −80° C. until serum growth hormone determination by radioimmunoassay as described above.

Assessment of Exogenously-stimulated Growth Hormone Release in the Dog After Oral Administration On the day of dosing, the test composition is weighed out for the appropriate dose and dissolved in water. Doses are delivered at a volume of 0.5–3 mL/kg by oral gavage to 2–4 dogs for each dosing regimen. Blood samples (5 mL) are collected from the jugular vein by direct vena puncture pre-dose and at 0.17, 0.33, 0.5, 0.75, 1, 2, 4, 6, 8 and 24 hours post dose using 5 mL vacutainers containing lithium heparin. The prepared plasma is stored at −20° C. until analysis.

Measurement of Canine Growth Hormone

Canine growth hormone concentrations are determined by a standard radioimmunoassay protocol using canine growth hormone (antigen for iodination and reference preparation AFP-1983B) and canine growth hormone antiserum raised in monkey (AFP-21452578) obtained from Dr. A. Parlow (Harbor-UCLA Medical Center, Torrence, Calif.). Tracer is produced by chloramine T-iodination of canine growth hormone to a specific activity of 20–40 $\mu$Ci/$\mu$g. Immune complexes are obtained by adding goat antiserum to monkey IgG (ICN/Cappel, Aurora, Ohio)plus polyethylene glycol, MW 10,000–20,000 to a final concentration of 4.3%; recovery is accomplished by centrifugation according to methods well known to those skilled in the art. This assay has a working range of 0.08–2.5 $\mu$g canine GH/tube.

Assessment of Canine Growth Hormone and Insulin-like Growth Factor-1 Levels in the Dog After Chronic Oral Administration The dogs receive test compound daily for either 7 or 14 days. Each day of dosing, the test composition is weighed out for the appropriate dose and dissolved in water. Doses are delivered at a volume of 0.5–3 ml/kg by gavage to 5 dogs for each dosing regimen. Blood samples are collected at days 0, 3, 7, 10 and 14. Blood samples (5 ml) are obtained by direct venipuncture of the jugular vein at pre-dose, 0.17, 0.33, 0.5, 0.754, 1, 2, 3, 6, 8, 12 and 24 hours post administration on days 0, 7 and 14 using 5 ml vacutainers containing lithium heparin. In addition, blood is drawn pre-dose and 8 hours on days 3 and 10. The prepared plasma is stored at −20° C. until analysis.

Female Rat Study

This study evaluates the effect of chronic treatment with a growth hormone secretagogue on weight, body composition and non-fasting plasma concentrations of glucose, insulin, lactate and lipids in estrogen-deficient and estrogen-replete female rats. Acute responsiveness of serum growth hormone levels to i.v. administration of the growth hormone secretagogue is assessed on the last day of dosing. Body weight is monitored weekly throughout the treatment period; additionally, body composition and plasma levels of glucose, insulin, lactate, cholesterol and triglycerides are assessed at the end of treatment.

Virgin female Sprague-Dawley rats are obtained from Charles River Laboratories (Wilmington, Mass.) and undergo bilateral ovariectomy (Ovx) or sham-surgery (Sham) at approximately 12 weeks of age. For sham surgeries, ovaries are exteriorized and replaced into the abdominal cavity. Following surgery the rats are housed individually in 20 cm×32 cm×20 cm cages under standard vivarium conditions (about 24° C. with about 12 hours light/12 hours dark cycle). All rats are allowed free access to water and a pelleted commercial diet (Agway ProLab 3000, Agway Country Food, Inc., Syracuse, N.Y.). The experiment is conducted in accordance with NIH Guidelines for the Care and Use of Laboratory Animals.

Approximately seven months post-surgery, Sham and Ovx rats are weighed and randomly assigned to groups. Rats are dosed daily by oral gavage with 1 mL of either vehicle (1% ethanol in distilled-deionized water), 0.5 mg/kg or 5 mg/kg of a growth hormone secretagogue for 90 days. Rats are weighed at weekly intervals throughout the study. Twenty-four hours after the last oral dose, the acute response of serum growth hormone (GH) to test composition is assessed by the following procedure. Rats are anesthetized with sodium pentobarbital 50 mg/kg. Anesthetized rats are weighed and a baseline blood sample (~100 μl) is collected from the tail vein. A combination of this invention or vehicle is then administered intravenously via the tail vein in 1 mL. Approximately ten minutes after injection, a second 100 μl blood sample is collected from the tail. Blood is allowed to clot at about 4° C., then centrifuged at 2000×g for about 10 minutes. Serum is stored at about −70° C. Serum growth hormone concentrations are determined by radioimmunoassay as previously described. Following this procedure, each anesthetized rat undergoes whole body scanning by dual-energy X-ray absorptiometry (DEXA, Hologic QDR 1000/W, Waltham Mass.). A final blood sample is collected by cardiac puncture into heparinized tubes. Plasma is separated by centrifugation and stored frozen as described above.

Plasma insulin is determined by radioimmunoassay using a kit from Binax Corp. (Portland, Me.). The interassay coefficient of variation is ≦10%. Plasma triglycerides, total cholesterol, glucose and lactate levels are measured using Abbott VP™ and VP Super System® Autoanalyzer (Abbott Laboratories, Irving, Tex.), using the A-Gent™ Triglycerides, Cholesterol and Glucose Test reagent systems, and a lactate kit from Sigma, respectively. The plasma insulin, triglycerides, total cholesterol and lactate lowering activity of a combination of this invention, are determined by statistical analysis (unpaired t-test) with the vehicle-treated control group.

The combinations of this invention, i.e., a $\beta_3$ adrenergic agonist and growth hormone or a growth hormone secretagogue, may be tested for hypoglycemic activity according to the following procedure.

Five to eight week old C57 BL/6J-ob/ob mice (obtained from Jackson Laboratory, Bar Harbor, Me.) are housed five per cage under standard animal care practices. After a one week acclimation period, the animals are weighed and 25 microliters of blood are collected via an ocular bleed prior to any treatment. The blood sample is immediately diluted 1:5 with saline containing 2% sodium heparin, and held on ice for glucose analysis. Animals are then regrouped, in groups of five per cage, such that the mean glucose values of the groups are similar, dosed daily for five days with test composition (0.01–100 mg/kg), a positive control such as englitazone or ciglitazone (50 mg/kg p.o.), (U.S. Pat. No. 4,467,902; Sohda et al., *Chem. Pharm. Bull.*, vol. 32, pp. 4460–4465, 1984)), or vehicle. All drugs are administered by oral gavage in a vehicle consisting of 0.25% w/v methyl cellulose. On day 5, the animals are weighed again and bled (via the ocular route) for blood glucose levels. The freshly collected samples are centrifuged for two minutes at 10,000×g at room temperature. The supernatant is analyzed for glucose, for example, by the ABA 200 Bichromatic Analyzer™, using the A-gent™ glucose UV reagent system[2] (hexokinase method) using 20, 60 and 100 mg/dl standards. Plasma glucose is then calculated by the equation, Plasma glucose (mg/dl)=Sample value×5×1.67=8.35×Sample value where 5 is the dilution factor and 1.67 is the plasma hematocrit adjustment (assuming the hematocrit is 40%).

[™]A registered trademark of Abbott Laboratories, Diagnostics Division, 820 Mission Street, So. Pasadena, Calif. 91030.
A modification of the method of Richterrich and Dauwalder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). The glucose lowering activity of test compositions is expressed in terms of % glucose normalization. For example, a glucose level which is the same as the positive control is expressed as 100%.

Combinations and methods of this invention, i.e., a $\beta_3$ adrenergic agonist and growth hormone or a growth hormone secretagogue, lower triglyceride levels and cholesterol levels and raise high density lipoprotein levels and are therefore of use in combating medical conditions wherein such lowering (and raising) is thought to be beneficial. Thus they may be used in the treatment of hypertriglyceridaemia, hypercholesterolemia and conditions of low HDL (high density lipoprotein) levels in addition to the treatment of atherosclerotic disease such as of coronary, cerebrovascular and peripheral arteries, cardiovascular disease and related conditions.

The compounds and combinations of this invention can be administered by oral, parenteral (e.g., intramuscular, intraperitoneal, intravenous or subcutaneous injection, or implant), nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders and granules and for companion animals the solid dosage forms include an admixture with food and chewable forms. In such solid dosage forms, the compounds and combinations of this invention can be admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings. In the case of chewable forms, the dosage form may comprise flavoring agents and perfuming agents.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of active ingredients in the compositions and methods of this invention may be varied; however, it is necessary that the amount of the active ingredients in such compositions be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals, to obtain effective release of growth hormone.

A preferred dosage range in humans is 0.01 to 5.0 mg/kg of body weight daily which can be administered as a single dose or divided into multiple doses.

A preferred dosage range in animals other than humans is 0.01 to 10.0 mg/kg of body weight daily which can be administered as a single dose or divided into multiple doses. A more preferred dosage range in animals other than humans is 0.1 to 5 mg/kg of body weight daily which can be administered as a single dose or divided into multiple doses.

The present invention includes within its scope the use of a combination of this invention, e.g., a $\beta_3$ adrenergic agonist and a growth hormone secretagogue or growth hormone, for the prevention or treatment of sleep disorders and/or sleep disturbances in mammals. The preferred mammal for purposes of this invention is human.

Since the present invention has an aspect that relates to treatment with a combination of active ingredients which may be administered separately, the invention also relates to combining separate pharmaceutical compositions in kit form. The kit comprises two separate pharmaceutical compositions: a $\beta_3$ adrenergic agonist, a prodrug thereof or a pharmaceutically acceptable salt of said $\beta_3$ adrenergic agonist or said prodrug; and a growth hormone secretagogue, a prodrug thereof or a pharmaceutically acceptable salt of said growth hormone secretagogue or said prodrug. The kit comprises a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the dosage form so specified should be ingested. Another example of such a memory aid is a calendar printed on the card e.g., as follows "First Week, Monday, Tuesday, . . . etc, . . . Second Week, Monday, Tuesday, . . . " etc. Other variations of memory aids will be readily apparent. A "daily dose" can be a single tablet or capsule or several tablets or capsules to be taken on a given day. Also, a daily dose of a $\beta_3$ adrenergic agonist, a prodrug thereof or a pharmaceutically acceptable salt of said $\beta_3$ adrenergic agonist or said prodrug can consist of one tablet or capsule while a daily dose of the growth hormone secretagogue, prodrug thereof or pharmaceutically acceptable salt of said growth hormone secretagogue or said prodrug can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

General Experimental Procedures

Amicon silica 30 $\mu$M, 60 Å pore size, was used for column chromatography. Melting points were taken on a Buchi 510 apparatus and are uncorrected. Proton and carbon NMR spectra were recorded on a Varian XL-300, Bruker AC-300, Varian Unity 400 or Bruker AC-250 at 25° C. Chemical shifts are expressed in parts per million down field from trimethylsilane. Particle beam mass spectra were obtained on a Hewlett-Packard 5989A spectrometer using ammonia as the source of chemical ionization. For initial sample dissolution, chloroform or methanol was employed. Liquid secondary ion mass spectra (LSIMS) were obtained on a Kratos Concept-1S high resolution spectrometer using cesium ion bombardment on a sample dissolved in a 1:5 mixture of dithioerythritol and dithiothreitol or in a thioglycerol matrix. For initial sample dissolution chloroform or methanol was employed. Reported data are sums of 3–20 scans calibrated against cesium iodide. TLC analyses were performed using E. Merck Kieselgel 60 F254 silica plates visualized (after elution with the indicated solvent(s)) by staining with 15% ethanolic phosphomolybdic acid and heating on a hot plate.

General Procedure A: (Peptide coupling using EDC): A 0.2–0.5M solution of the primary amine (1.0 equivalent) in dichloromethane (or a primary amine hydrochloride and 1.0–1.3 equivalents of triethylamine) is treated sequentially with 1.0–1.2 equivalents of the carboxylic acid coupling partner, 1.5–1.8 equivalents hydroxybenzotriazole hydrate (HOBT) or 1-Hydroxy-7-azabenzotriazole (HOAT) and 1.0–1.2 equivalents (stoichiometrically equivalent to the quantity of carboxylic acid) 1-(3-dimethylaminopropyl)-3-ethylcarbodiimide hydrochloride (EDC) and the mixture is stirred overnight in an ice bath (the ice bath is allowed to warm, thus the reaction mixture is typically held at about 0–20° C. for about 4–6 h and about 20–25° C. for the remaining period). The mixture is diluted with ethyl acetate or other solvent as specified, and the resulting mixture washed twice with 1N NaOH, twice with 1N HCl (if the product is not basic), once with brine, dried over $Na_2SO_4$, and concentrated giving the crude product which is purified as specified. The carboxylic acid component can be used as the dicyclohexylamine salt in coupling to the primary amine or hydrochloride of the latter; in this case no triethylamine is employed.

General Procedure B. (Cleavage of a t-BOC-protected amine using concentrated HCl). The t-Boc amine was dissolved in a minimum volume of ethanol and the resulting solution was cooled to about 0° C. and concentrated HCl (typically about 1–4 mL per mmol amine) was added and the reaction was warmed to room temperature and stirred for about 1–2.5 hours (the time required for complete disappearance of the starting material to a more polar product as judged by TLC). The resulting solution or suspension was concentrated, and the residue coevaporated several times with added ethanol to give the free amine which was used without further purification or purified as specified.

General Procedure C. (Cleavage of a CBZ-protected amine using 10% palladium on carbon) The CBZ amine, ethanol (typically about 1 mL per every 0.03–0.08 mmol of amine), and 10% palladium on carbon (typically about 20–100% of the weight of the amine used) were combined and hydrogenated at about 40–50 psi hydrogen on a Parr® shaker overnight. The mixture was then filtered through a bed of Celite®. The Celite® was washed with ethanol, and the filtrate was concentrated in vacuo to give the de-benzylated amine which was used without further purification or purified as specified.

EXAMPLE ONE (4-(2-(2-(6-Aminopyridin-3-yl)-2(R)-hydroxyethylamino)ethoxy)acetic Acid

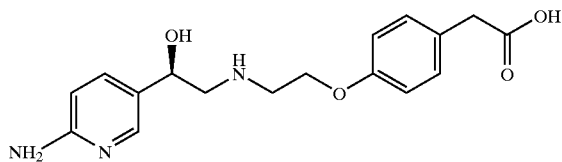

A. Methyl (4-(2-t-butoxycarbonylaminoethoxy)phenyl) acetate. To a stirred solution of methyl 4-hydroxphenyl acetate (4.00 g, 24.1 mmol) and triphenylphosphine (9.50 g, 36.1 mmol) in THF (24 mL) were added solutions of 2-(t-butoxycarbonylamino)ethanol (5.80 g, 36.1 mmol) and diethylazodicarboxylate (5.70 mL, 36.1 mmol) in THF (6 mL, each) simultaneously over a 1.5 h period. After an additional 3 h, the reaction was concentrated in vacuo and subjected to flash chromatography (600 g silica gel, 20% ethyl acetate/hexanes) to afford a golden oil, 5.78 g. $^1$H NMR (CDCl$_3$) δ 7.15 (d, 2H), 6.80 (d, 2H), 4.95 (br s, 1H), 3.98 (m, 2H), 3.65 (s, 3H), 3.54 (s, 2H), 3.48 (m, 2H), 1.44 (s, 9H).

B. Methyl (4-(2-aminoethoxy)phenyl)acetate. To a cooled (5° C.), stirred solution of methyl (4-(2-t-butoxycarbonylamino-ethoxy)phenyl) acetate (prepared as described in Example One, Step A, 5.75 g, 18.6 mmol) in dichloromethane (20 mL) was added trifluoroacetic acid (6 mL). The resulting solution was stirred at ambient temperature for 2 h, diluted in ethyl acetate, washed with half-saturated sodium carbonate, brine, dried (Na$_2$SO$_4$) and concentrated in vacuo to afford an orange oil, 3.25 g. $^1$H NMR (CDCl$_3$) δ 7.10 (d, 2H), 6.77 (d, 2H), 3.92 (t, 2H), 3.60 (s, 3H), 2.49 (s, 2H), 3.00 (t, 2H).

C. Methyl (4-(2-(2(R)-hydroxy-2-tetrazolo[1,5-a]pyridin-6-ylethylamino)ethoxy)phenyl)acetate. A solution of methyl (4-(2-aminoethoxy)phenyl)acetate (prepared as described in Example One, Step B, 0.56 g, 2.71 mmol) and (2R)-(tetrazolo[1,5-a]pyrid-6-yl)oxirane (0.40 g, 2.47 mmol), generated as in Example 1 of U.S. Pat. No. 5,030,640, in methanol (7.5 mL) was heated at reflux temperature for 7 h. Concentration of the reaction solution in vacuo afforded a solid which was subjected to flash chromatography (3% methanol/chloroform) to afford the title compound of Step C as a colorless solid, 0.52 g. $^1$H NMR (CDCl$_3$) δ 8.86 (s, 1H), 7.92 (d, 1H), 7.57 (d, 1H), 7.15 (d, 2H), 6.81 (d, 2H), 4.83 (dd, 1H), 4.06 (t, 2H), 3.66 (s, 3H), 3.56 (s, 2H), 3.20–3.02 (m, 3H), 2.76 (dd, 1H).

D. Methyl (4-(2-(2-(6-aminopyridin-3-yl)-2(R)-hydroxyethylamino)-ethoxy)phenyl)acetate. A slurry of methyl (4-(2-(2(R)-hydroxy-2-tetrazolo[1,5-a]pyridin-6-ylethylamino)-ethoxy)phenyl) acetate (prepared as described in Example One, Step C, 0.51 g, 1.37 mmol) and stannous chloride-dihydrate (0.93 g, 4.12 mmol) in methanol (7 mL) was heated at 60° C. for 3 h. The resulting clear solution was diluted into methylene chloride, washed with one-half saturated aqueous sodium carbonate, brine, dried (Na$_2$SO$_4$) and concentrated in vacuo to a foam, 0.42 g. Flash chromatography (10% methanol/dichloromethane) afforded a colorless solid, 0.22 g; m.p. 90–93° C. $^1$H NMR (CDCl$_3$) δ 7.95 (s, 1H), 7.40 (d, 1H), 7.10 (d, 2H), 6.78 (d, 2H), 6.42 (d, 1H), 4.54 (dd, 1H), 4.36 (s, 2H), 4.00 (t, 2H), 3.63 (s, 3H), 3.52 (s, 2H), 3.06–2.92 (m, 2H), 2.86 (dd, 1H), 2.68 (dd, 1H).

E. (4-(2-(2-(6-Aminopyridin-3-yl)-2(R)-hydroxyethylamino)ethoxy)phenyl)-acetic acid. To a stirred solution of the product of Example One, Step D, methyl (4-(2-(2-(6-aminopyridin-3-yl)-2(R)-hydroxyethylamino) ethoxy)phenyl)acetate (0.11 g, 0.03 mmol), in methanol (6 mL) were added water (1.5 mL) and potassium hydroxide (0.07 g, 1.3 mmol). The resulting solution was stirred at room temperature for 4 h and concentrated in vacuo. The resulting mixture was dissolved in water (2 mL) and the pH adjusted to 5.5 with 1N aqueous hydrochloric acid. The precipitate was filtered and dried at 80° C. in vacuo to afford the title compound of this Example as a colorless solid, 0.10 g; m.p. 233–235° C. $^1$H NMR (DMSO-d$_6$) δ 7.81 (s, 1H), 7.33 (d, 1H), 7.13 (d, 2H), 6.86 (d, 2H), 6.40 (d, 1H), 6.00 (brs, 2H), 4.78 (dd, 1H), 4.23 (t, 2H), 3.46 (s, 2H), 3.33 (t, 2H), 3.09 (t, 2H).

EXAMPLE TWO

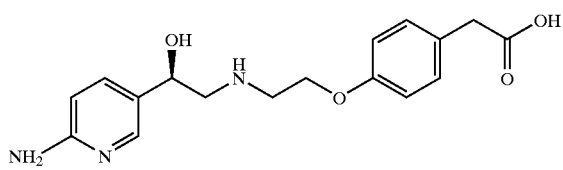

(4-(2-(2-(6-Aminopyridin-3-yl)-2-(R)-hydroxyethylammonium)-ethoxy)-phenyl)-acetate A mechanically stirred slurry of the title compound of Preparation Five (50.0 gm, 0.2806 mol, 1.0 eq) and the title compound of Preparation Nine (99.4 gm, 0.477 mol, 1.7 eq) in 5:1 (vol/vol)::toluene:DMSO (375 mL) was heated on a steam bath. The slurry became homogenous at about 70° C., and the temperature was maintained at 90° C.–95° C. for 3 to 16 hrs. The solution was cooled to 10° C.–15° C. This resulted in the formation of a precipitate. Di-t-butyldicarbonate (129 mL, 0.561 mol, 2.0 eq) was added dropwise over a one hour period. The resulting homogenous solution was stirred at room temperature overnight. The solution was poured into a mixture of ethyl acetate (1 L) and water (850 mL). After stirring for 10 min, the phases were allowed to separate, at which time a heavy red oil fell out into the aqueous layer. The aqueous layer, with oil, was removed. The organic layer was washed with water (500 mL) and concentrated to an amber oil. This amber oil was taken up in 6N HCl (300 mL) and heated on the steam bath overnight. The solution was cooled to room temperature, and the solids which precipitated were filtered. (These solids are the amino acid of the excess side chain which was used in the coupling with the epoxide.) The acidic solution containing the title compound was concentrated under vacuum to a semi-solid. The semi-solid was treated with water and then reconcentrated (twice) to remove excess HCl. The solid was dissolved in water and brought to pH 7 with potassium hydroxide. The solid which precipitated was filtered and washed first with water and then with THF. The solids were dried on the filter funnel to a weight of 22.5 gm. The crude solid was redissolved in 30 volumes of 90° C. water and treated with decolorizing carbon. After filtration to remove the carbon, the filtrate was cooled and concentrated by evaporation of some of the water. The precipitate which formed was filtered to provide 9.5 gm of the title compound. NMR (400 MHz, DMSO-d$_6$+D$_2$O): d=7.79 (d, 1H, J=1.87), 7.34–7.32 (m, 1H), 7.11 (d, 2H, J=8.51), 6.79 (d, 2H, J=8.51), 6.41 (d, 1H, J=8.51), 4.54–4.51 (m, 1H), 4.01–3.99 (m, 2H), 3.35 (s, 2H), 2.97–2.94 (m, 2H), 2.79–2.69 (m, 2H). MS (APCI) m/z 332.2 (MH$^+$), 314.2, 159.1, 156.9.

EXAMPLE THREE

2-Amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide Hydrochloride and 2-Amino-N-[2-(3a-(S)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide Hydrochloride

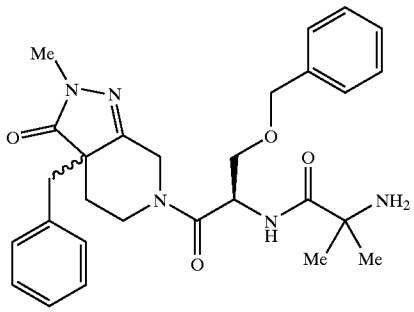

A. {1-[2-(3a-(R,S)-Benzyl-2-methyl-3-oxo-2,3,3a,4,6,7-hexahydro-pyrazolo[4,3-c]pyridin-5-yl)-1-(R)-benzyloxymethyl-2-oxo-ethylcarbamoyl]-1-methyl-ethyl}-carbamic acid tert-butyl ester. According to the method outlined in General Procedure A, 1.12 g (4.6 mmol) of the compound of Preparation Thirteen and 1.75 g (0.51 mmol) of the compound of Preparation Ten were coupled to give a mixture of diastereomers. The residue was purified by silica gel chromatography using an elution gradient of (1:1 v/v ethyl acetate:hexane) to 100% ethyl acetate to give 350 mg of the less polar isomer of Example Three, Step A and 250 mg of the more polar isomer of Example Three, Step A. MS (Cl, NH$_3$) 606 (MH$^+$) for both isomers.

B. 2-Amino-N-[2-(3a-(R)-benzyl-2-methyl-3-oxo-2,3,3a,4,6,7-hexahydropyrazolo[4,3-c]pyridin-5-yl)-1-(R)-benzyloxymethyl-2-oxo-ethyl]-isobutyramide hydrochloride. To 250 mg (0.41 mmol) of the less polar isomer of Example Three, Step A in 15 mL of ethanol was added 5 mL of concentrated HCl and the mixture was stirred at room temperature for about 5 h. The mixture was concentrated and the residue was precipitated from ethanol/hexane and dried under vacuum to give 130 mg of the title compound of Example Three, Step B. MS (Cl, NH$_3$) 506 (MH$^+$). $^1$HNMR (CD$_3$OD): δ 7.33 (m, 5H), 7.14 (m, 5H), 5.22 (m, 1H), 4.57 (m, 3H), 3.80 (m, 2H), 3.14 (m, 1H), 3.04 (s, 3H), 2.96 (m, 2H), 2.61 (m, 2H), 1.63 (m, 7H).

C. 2-Amino-N-[2-(3a-(S)-benzyl-2-methyl-3-oxo-2,3,3a,4,6,7-hexahydropyrazolo[4,3-c]pyridin-5-yl)-1-(R)-benzyloxymethyl-2-oxo-ethyl]-isobutyramide hydrochloride. To 250 mg (0.41 mmol) of the more polar isomer of Example Three, Step A in 15 mL of ethanol was added 5 mL of concentrated HCl and the mixture was stirred at room temperature for about 5 h. The mixture was concentrated and the residue was precipitated from ethanol/hexane and dried under vacuum to give 120 mg of the title compound of Example Three, Step C. MS (Cl, NH$_3$) 506 (MH$^+$). $^1$HNMR (CD$_3$OD): δ 7.31 (m, 5H), 7.13 (m, 5H), 6.78 (m, 1H), 5.28 (m, 1H), 4.62 (m, 3H), 3.81 (M, 2H), 3.14 (m, 1H), 2.62 (m, 3H), 1.58 (m, 7H).

D. 2-Amino-N-[2-(3a-(R)-benzyl-2-methyl-3-oxo-2,3,3a, 4,6,7-hexahydropyrazolo[4,3-c]pyridin-5-yl)-1-(R)-benzyloxymethyl-2-oxo-ethyl]-isobutyramide methanesulfonate. Saturated aqueous sodium bicarbonate was added to 3.60 g (6.6 mmol) of the compound of Example Three, Step B and the mixture was extracted with ethyl acetate. The organic layer was dried over MgSO$_4$ and concentrated. The residue was dissolved in ethyl acetate, cooled to about 0° C., 0.43 mL (6.6 mmol) of methane-sulfonic acid was added and the mixture was stirred for about 0.5 h. Hexane (200 mL) was added to the solution and the mixture was stirred for about 1 h and filtered to give 3.40 g of a white solid. The solid was recrystallized from 3% aqueous ethyl acetate to give 2.55 g of the title compound of Example Three, Step D as a white crystalline solid. MS (Cl, NH$_3$) 506 (MH$^+$).

EXAMPLE FOUR

2-Amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c]pyridin-5-yl)-ethyl)-2-methyl-propionamide The title compound of this Example was prepared according to the scheme illustrated below by coupling the pyrazalone-piperidine (prepared in a manner analogous to the procedure set forth in Preparations Twelve and Thirteen, using the appropriate starting materials) in the below scheme with the (D)-OBnSer derivative (prepared in a manner analogous to the procedure set forth in Preparation Ten, using the appropriate starting materials) in the below scheme in an analogous manner to the procedures described in General Procedures A and B.

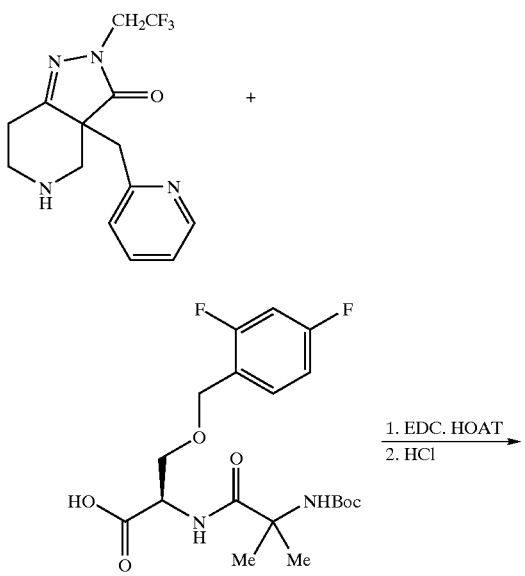

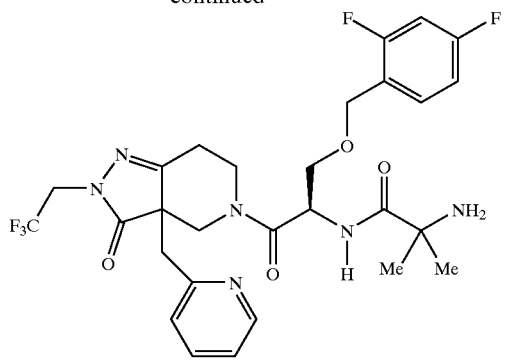

EXAMPLE FIVE

2-Amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl-2-oxo-ethyl}-2-methylpropionamide, Hydrochloride

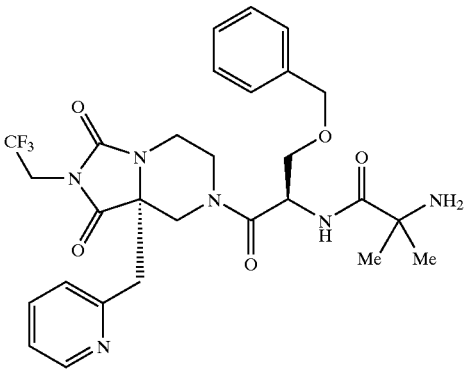

A. 2-Pyridin-2-ylmethyl-piperazine-1,2,4-tricarboxylic acid 1-benzyl ester 4-tert-butyl ester 2-methyl ester. A stirred solution of piperazine-1,2,4-tricarboxylic acid 1-benzyl ester 4-tert-butyl ester 2-methyl ester (200 g, 529 mol), prepared as described by Bigge et al. (Tetrahedron Let. 1989, 30, 5193), in tetrahydrofuran (200 mL) and DMF (1.5 L) was cooled to about −78° C., and a 0.5 M solution of potassium bis(trimethylsilyl)amide in THF (1.27 L) was added. After the above solution had stirred for about one hour, the free base of 2-picolyl chloride was generated by extracting the corresponding hydrochloride salt (217 g, 1.32 mol) from saturated sodium bicarbonate solution with methylene chloride. The combined organic extracts were dried (MgSO$_4$), concentrated, immediately dissolved in DMF (100 mL), and then added dropwise to the enolate containing solution. The reaction was stirred for about 4 hours at about −78° C., then slowly warmed to room temperature and stirred overnight. The toluene and THF were removed under reduced pressure. The residue was extracted from water (1.5 L) with ethyl acetate (3×1 L), the combined extracts were then washed with water (1.5 L), dried (MgSO$_4$) and then concentrated in vacuo to give 240 g of crude product of the title compound of Example Five, Step A which was carried on to the next step: +APCI MS (M+H)$^+$ 470, (M-$^t$Bu+H) 436; $^1$H NMR=400 MHz (methanol-d$_4$) d: 8.4 (arom, m, 1H), 7.65–7.2 (arom, m, 7H), 6.94 (arom, m, 1H), 5.18

(CbzNCHH, m, 1H), 5.05 (CbzNCHH, m, 1H), 2.54 (m, 1H), 1.41 (Boc, s, 9H).

B. 3-Pyridin-2-ylmethyl-piperazine-1,3-dicarboxylic acid 1-tert-butyl ester 3-methyl ester. The title compound of Example Five, Step A, (240 g) in methanol (1 L), and 10% palladium on carbon (10 g, added in 100 mL water) were combined and hydrogenated at about 40–50 psi hydrogen on a Parr® shaker for about 2 days. The mixture was then filtered through a bed of diatomaceous earth. The diatomaceous earth was washed with ethanol, and the filtrate was concentrated in vacuo to give the de-benzylated amine. Two of the above alkylation/reductions were combined and purified by silica gel chromatography using 1:1 ethyl acetate/hexanes to ethyl acetate to 1:9 methanol/ethyl acetate as eluent and yielded the title compound of Example Five, Step B (217 g, 61%): +APCI (M+1)$^+$ 336; $^1$H NMR=400 MHz (methanol-d$_4$) d: 8.45 (arom, d, 1H), 7.72 (arom, t, 1H), 7.26–7.11 (arom, m, 2H), 4.38 (br s, 1H), 3.57 (MeO, s, 3H), 1.41 (Boc, s, 9H).

C. 1,3-Dioxo-8a-pyridin-2-ylmethyl-2-(2,2,2-trifluoro-ethyl)-hexahydro-imidazo[1,5-a]pyrazine-7-carboxylic acid tert-butyl ester. To a suspension of N,N'-carbonyldiimidazole (69 g, 426 mmol) and 2,2,2-trifluoro-ethylamine hydrochloride (71 g, 527 mmol) in dichloromethane (500 mL) was added triethylamine (76 mL, 544 mmol) at about 0° C. dropwise. The reaction was then warmed to room temperature and stirred at room temperature for about 30 minutes. A solution of the title compound of Example Five, Step B (57 g, 170 mmol) in dichloromethane (100 mL) was then added, and the reaction was heated to about 40° C. and then stirred for approximately 2 days. The reaction was quenched with saturated sodium bicarbonate solution, and the mixture was then extracted twice with dichloromethane. The combined organic layers were extracted twice with water, dried over anhydrous magnesium sulfate, filtered and concentrated in vacuo to give crude product. Purification by silica gel chromatography using 1:9 to 1:2 to 1:1 ethyl acetate/hexanes as eluent afforded the title compound of Example Five, Step C (68.3 g, 94%) as an amorphous solid: +APCI MS (M+H)$^+$ 429; $^1$H NMR=400 MHz (CDCl$_3$) δ: 8.4 (arom, d, 1H), 7.54 (arom, t, 1H), 7.12 (arom, t, 1H), 7.04 (arom, d, 1H), 4.16–4.00 (CF$_3$CH$_2$, m, 2H), 3.41 (PyrCH$_2$, Ab$_q$, 2H), 1.50 (Boc, s, 9H).

D. 8a-Pyridin-2-ylmethyl-2-(2,2,2-trifluoro-ethyl)-tetrahydro-imidazo[1,5-a]pyrazine-1,3-dione. The title compound of Example Five, Step C (22.8 g, 53.2 mmol) was deprotected according to the method described in General Procedure B to give a pink solid. The residue was extracted from saturated aqueous NaHCO$_3$ with methylene chloride, the combined organic layers were washed with brine, dried (MgSO$_4$) and concentrated to give the title compound of Example Five, Step D as a light yellow solid (13.7 g, 78%): +APCI MS (M+H)$^+$ 329; $^1$H NMR=400 MHz (CDCl$_3$) δ: 8.42 (arom, ddd, 1H), 7.55 (arom, td, 1H), 7.37–7.07 (arom, m, 2H); 4.15–3.98 (CF$_3$CH$_2$, m, 2H), 3.87 (NCHHCH$_2$, m, 1H), 3.79 (CCHHNH, d, 1H), 3.40 (CCHHNH, d, 1H), 3.25 (PyrCHH, d, 1H), 3.13 (NCHHCH$_2$, ddd, 1H), 3.02 (NCH$_2$CHHNH, dd, 1H), 2.74 (PyrCHH, d, 1H), 2.66 (NCH$_2$CHHNH, td, 1H).

E. (1-{1(R)-Benzyloxymethyl-2-[1,3-dioxo-8a-pyridin-2-ylmethyl-2-(2,2,2-trifluoro-ethyl)-hexahydro-imidazo[1,5-a]pyrazin-7-yl]-2-oxo-ethylcarbamoyl}-1-methyl-ethyl)-carbamic acid tert-butyl ester. According to General Procedure A, the title compound of Example Five, Step D (5.6 g, 15.4 mmol) was coupled to the title compound of Preparation Fifteen (5.84 g, 15.4 mmol), and the product was purified by silica gel chromatography using 2:1 ethyl acetate/hexanes as eluent to give the title compound of Example Five, Step E (34513-284-1) as a colorless solid (7.3 g, 69%): +APcI MS (M+H)$^+$ 691; $^1$H NMR=400 MHz (CDCl$_3$) δ: 8.35 (arom, m, 1H), 5.23–5.10 (m, 2H), 2.60 (t, 1H).

F. 2-Amino-N-1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl]2-methyl-propionamide, hydrochloride. The title compound of Example Five, Step E (410 mg, 0.59 mmol) was deprotected according to the method described in General Procedure B to give a colorless solid (6.23 g, 94%).

HPLC separation of the isomers provided the shorter retained isomer (2.65 g, 85%): A 70×500 mm Inertsil 15 micron C-8 column (Phenomenex Inc, 2320 W. 205th St., Torrance, Calif. 90501) was equilibrated with 100% 0.050M KH$_2$PO$_4$ adjusted to pH 2.20 with H$_3$PO$_4$. The sample was dissolved in 20 ml mobile phase along with a few drops of H$_3$PO$_4$ and was injected onto the column. The column was eluted at 237.5 ml/min., 100% buffer for 1 min., ramped to 75% buffer 25% CH$_3$CN in 12.5 min., and then held for 21.5 min. (total run time 35 min.). The column was then rinsed off with 50% water 50% CH$_3$CN. The product was observed at 254 nm, and was found in fractions 7–11 (24–29 min.). These fractions were combined, adjusted to a pH of about 7.5 with NaHCO$_3$ and then extracted with CHCl$_3$ (2×1000 ml). The organics were combined, dried (Na$_2$SO$_4$) and concentrated to a colorless foam (86.5% diastereomer excess).

HPLC analysis was performed on an Hewlett-Packard 1050 system with a 1050 DAD, autosampler and solvent delivery system (Hewlett-Packard Company, Analytical Business Center, 2850 Centerville Road, Wilmington, Del. 19808-1610). Data was imported into a HP Vectra XM series 3 running HP Chemstation ver A.4.02. A 10 μL sample dissolved in the mobile phase at 1 mg/ml was injected for analysis. A Prodigy 3.2×250 mm 5 micron C-8 column (Phenomenex Inc, 2320 W. 205th St., Torrance, Calif. 90501) was employed with the following solvents: A=0.050 M KH$_2$PO$_4$ adjusted to pH 2.20 with H$_3$PO$_4$; C=acetonitrile. An isocratic elution was employed using 65% A and 35% C with a flow rate of 0.5 ml/min. detecting at uv, 254 nm. The desired enantiomer eluted at 5.7 min., while the less desired enantiomer eluted at 6.3 min.

The desired enantiomer was taken up in ethanol (150 mL), slowly treated with concentrated aqueous HCl (75 mL) at about 0° C., and the solvent was then removed under reduced pressure. The residue was then concentrated from ethanol (4x) to remove residual water. The product was triturated with ethyl ether to give the title compound of Example Five (2.72 g, 97%): +APcI MS (M+H)$^+$ 591; $^1$H NMR=400 MHz (methanol-d$_4$) δ: 8.83–6.90 (NH and arom, series of m, 10H), 5.18–2.90 (aliphatic, series of m, 15H), 1.59 (Me, s, 6H); $^{13}$C NMR=100 MHz (methanol-d$_4$) δ: 172.4, 148.1, 143.4, 130.3, 129.5, 129.0, 127.7, 74.4, 69.7, 64.6, 58.2, 52.3, 47.9, 46.9, 40.8, 40.5, 39.2, 36.0, 24.2, 24.1.

EXAMPLE SIX

2-Amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, Hydrochloride

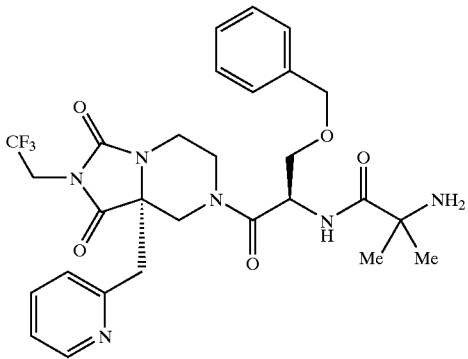

A. 1,3-Dioxo-8a(S)-pydridin-2-ylmethyl-2-(2,2,2-trifluoro-ethyl)-hexahydro-imidazo[1,5-a]pyrazine-7-carboxylic acid tert-butyl ester. To a solution of the title compound of Example Five, Step D (206 g, 628 mmol) in 10:1 acetone/water (4.5 L) was added D-tartaric acid (94.2 g, 628 mmol). After several minutes a colorless precipitate formed. After stirring for about 2 days the solid was collected by filtration (144 g, 80% ee). The precipitate was then placed in acetone (2 L) and was heated for about 15 hours at about 55° C. The mixture was cooled and the solid collected by filtration (117 g, 94% ee). The tartrate salt was then extracted from aqueous sodium bicarbonate with 3:1 chloroform/isopropanol to give the free base compound of Example Six, Step A (81.7 g, 78% ee) as an off-white solid. HPLC analysis of the compound indicated that the material had an enantiomeric excess of 96%: +APcI MS (M+H)+ 329.

HPLC analysis was performed on an Hewlett-Packard 1050 system with a 1050 DAD, autosampler and solvent delivery system. Data was imported into a HP Vectra XM series 3 running HP Chemstation ver A.4.02. When possible, samples were dissolved in the mobile phase at 1 mg/ml. A Chiracel AD 4.6×250 mm column (Chiral Technologies, 730 Springfield Drive, P.O. Box 564, Exton Pa. 19341) was employed with the following solvents: A=hexane+0.1% diethylamine (v/v); C=isopropanol+0.1% diethylamine (v/v). An isocratic elution was employed using 85% A and 15% C with a flow rate of 1 ml/min, detecting at uv, 254 nm. The desired enantiomer eluted at 11.8 min., while the less desired enantiomer eluted at 15.6 min.

B. (1-{1(R)-Benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethylcarbamoyl}-1-methyl-ethyl)-carbamic acid tert-butyl ester. To a solution of the title compound of Example Six, Step A at about 0° C. (10.0 g, 30.5 mmol) and the title compound of Preparation Fifteen (13.9 g, 36.6 mmol) in ethyl acetate (200 mL) was added triethylamine (17 mL, 122 mmol), followed by slow addition of a 50% solution of 1-propanephosphonic acid cyclic anhydride in ethyl acetate (18.1 mL, 30.5 mmol) and the reaction was allowed to warm to room temperature. After about 15 hours, the reaction was extracted from saturated aqueous sodium bicarbonate with ethyl acetate, the combined organics were washed with water and then brine, dried (MgSO4), concentrated in vacuo, and the product then purified by silica gel chromatography using 0% to 1% to 5% methanol in chloroform as eluent to give the title compound of Example Six, Step B (19.5 g, 92%) as a colorless foam.

C. 2-Amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, hydrochloride. The title compound of Example Five, Step E (17.5 g, 25.3 mmol) was deprotected according to the method described in General Procedure C to give a colorless solid. The product was triturated with ethyl ether to give the title compound of Example Six, Step C (13.6 g, 90%): +APcI MS (M+H)+ 591.

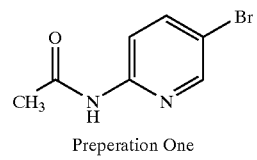

Preperation One

N-(5-Bromo-pyridin-2-yl)-acetamide. A solution of 2-amino-5-bromopyridine (25.0 g, 144 mmol) in acetic acid (50 ml) and acetic anhydride (25.0 g) was heated at reflux for two hours. The reaction mixture was then cooled and poured into water (750 ml) with stirring. After one hour, the solution was adjusted to pH 10 with 50% sodium hydroxide and the precipitate was filtered, washed with water and dried to give 26.5 g (85%) of the title product as a white flaky solid. mp 175–176° C. $^1$H NMR (CDCl$_3$): δ=8.29 (d, 1H); 8.12 (d, 1H); 7.96 (br, 1H); 7.78 (d of d, 1H); 2.19 (s, 3H). MS (EI): m/z=214, 216 (M+, Br isotopes).

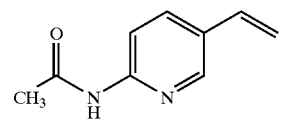

Preparation Two

N-(5-Vinyl-pyridin-2-yl)-acetamide. A solution of of N-(5-bromo-pyridin-2-yl)-acetamide (prepared as described in Preparation One, 4.30 g, 20 mmol) in acetonitrile (15 ml) and triethylamine (5.04 ml) was treated with palladium acetate (45 mg, 0.2 mmol) and tri-o-tolylphosphine (203 mg, 0.66 mmol). The mixture was placed in a pressure reactor under 50 psig of ethylene pressure and heated at 85° C. for 66 hours. The reaction mixture was cooled, vented, and partitioned between phosphate buffer (0.1M, pH 6.6) and ethyl acetate. The aqueous phase was extracted with ethyl acetate twice more. The combined ethyl acetate extracts were washed with additional phosphate buffer, brine and dried over sodium sulfate. The extracts were filtered and evaporated to afford 2.06 g (63%) of the title product as a flaky crystalline residue. Recrystallization from ethyl acetate/cyclohexane gave colorless flakes. mp 120–121° C. $^1$H NMR (CDCl$_3$): δ=8.55 (br, 1H); 8.24 (d, 1H); 8.15 (d, 1H); 7.76 (d of d, 1H); 6.64 (d of d, 1H); 5.73 (d, 1H); 5.28 (d, 1H); 2.19 (s, 3H). MS (CI): m/z=163 (M+H+).

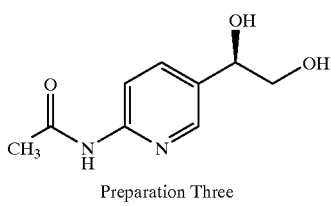

Preparation Three

R)-N-(5-(1,2-Dihydroxy-ethyl)-pydridin-2-yl)-acetamide. A suspension of AD-Mix-B® (56.33 g) in water (200 ml) and t-butanol (200 ml) was cooled to 5° C. and N-(5-vinyl-pyridin-2-yl)-acetamide (prepared as described in Preparation Two, 6.52 g, 40.2 mmol) was added followed by 2-propanol (400 ml). The mixture was stirred at 5° C. for 12 hours and then at 20° C. for 12 hours. The reaction mixture was then treated with sodium sulfite (60.4 g), stirred for 30 minutes and then diluted with 500 ml of 2-propanol and stirred for an additional one hour. The mixture was filtered and the alcoholic phase was separated and evaporated to dryness. The residue was slurried in 500 ml of 2-propanol and evaporated again. The residue was dried to afford 6.35 g (80%) of the title product as colorless crystals. The crystals were recrystallized by dissolving in hot glacial acetic acid, diluting 7-fold with 2-propanol, cooling and seeding to give the title product as crystals. mp 184–185° C. [1] H NMR (dmso-$d_6$): δ=8.22 (d, 1H); 7.99 (d, 1H); 7.68 (d of d, 1H); 4.52 (t, 1H); 3.44 (m, 2H); 2.07 (s, 3H). MS (CI): m/z=197 (M+H$^+$). Optical Rotation: –4.52° (c=0.05, acetic acid). Analysis: Calculated for $C_9H_{12}N_2O_3$: C, 55.09%; H, 6.17%; N, 14.28%. Found: C, 55.43%; H, 5.97%; N,13.96%.

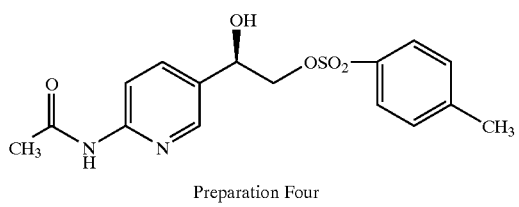

Preparation Four (R)-Toluene-4-sulfonic acid 2-(6-acetylamino-pyridin-3-yl)-2-hydroxy-ethyl ester. A slurry of (R)-N-(5-(1,2-dihydroxy-ethyl)-pyridin-2-yl)-acetamide (prepared as described in Preparation Three, 71.2 g, 362 mmol) in anhydrous pyridine (362 ml) was cooled to 5° C. and treated with p-toluenesulfonyl chloride (69.18 g, 362 mmol) in one portion. The reaction mixture was stirred at 5° C. for 20 minutes, then the cooling bath was removed and the mixture was stirred at ambient temperature for two hours. The mixture was then concentrated, dissolved in 30 ml of methanol, concentrated and dissolved in toluene (300 ml) and concentrated again. The residue was treated again with methanol and toluene, then the residue was dissolved in ethyl acetate and washed sequentially with half-saturated brine, brine and dried over sodium sulfate. The filtrate was evaporated to afford 102.2 g (80%) of the title product as light buff crystals. Recrystallization from ethanol-cyclohexane afforded the title product as colorless crystals. mp 124–126° C. $^1$H NMR (dmso-$d_6$): δ=10.5 (br, 1H); 8.21 (d, 1H); 7.94 (d, 1H); 7.68 (d, 2H); 7.51 (d of d, 1H); 7.41 (d, 1H); 5.87 (d, 1H); 4.76 (d of d, 1H); 4.05 (d, 2H); 2.41 (s, 3H); 2.10 (s, 3H). MS (CI): m/z=351 (M+H$^+$). Optical Rotation: –36.181° (c=1.19, acetone). Analysis: Calculated for $C_{16}H_{18}N_2O_5S$: C, 54.85%; H, 5.18%; N, 7.99%. Found: C, 54.91%; H, 5.34%; N, 8.06%.

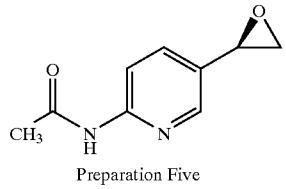

Preparation Five (R)-N-(5-Oxiranyl-pyridin-2-yl)-acetamide. A solution of (R)-toluene-4-sulfonic acid 2-(6-acetylamino-pyridin-3-yl)-2-hydroxy-ethyl ester (prepared as described in Preparation Four, 200 g, 0.57 mol) in THF (2.4 L) was cooled to –15° C. and potassium t-butoxide (542 ml, 0.542 mol, 1M in THF) was added slowly at –15° C. to –10° C. over a two hour period. Stirring was continued at –15° C. for an additional 40 minutes. The reaction mixture was filtered with the aid of Celite®. The filtration was done through cloth precoated with Celite®. The filter cake was washed with tetrahydrofuran. The filtrate was concentrated under vacuum to afford 300 ml of an oil. The oil was diluted with 1.2 liters of hexanes which resulted in the formation of a solid. The suspension was stirred at room temperature for one hour to granulate the solid. The suspension was filtered and the filtrate was washed with hexanes to afford 80.0 g (78.8%) of the title product as a solid. mp 96–98° C. $^1$H NMR (CDCl$_3$): δ=8.70 (br, 1H); 8.21 (m, 2H); 7.57 (d of d, 1H); 3.86 (m, 1H); 3.17 (m, 1H); 2.83 (m, 1H); 2.19 (s, 3H). MS (CI): m/z=179 (M+H$^+$).

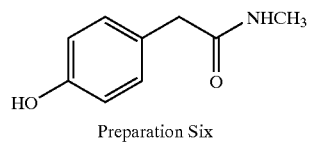

Preparation Six

N-Methyl 4-hydroxyphenylacetamide. Monomethylamine, (22.43 kg, 722.15 mol, 6 eq.) was added over a 7-hour period to a solution of methyl-4-hydroxyphenylacetate (20.0 kg, 120.35 mol, 1.0 eq.) in methanol (31.7 gal, 120 L) and stirred overnight at room temperature. Methanol was then displaced under vacuum with ethyl acetate. The resulting slurry (about 20 gal, 75.7 L) was stirred at +10° C. for 1 hour, then filtered and dred under vacuum at 45° C. to yield the title compound(18.68 kg, 94% of theory).

mp 124–125° C. NMR (300 MHz, $d_6$-DMSO): δ=9.26 (s, 1H), 8.00–7.65 (br s, 1H), 7.21–6.90 (m, 2H), 6.86–6.55 (m, 2H), 3.26 (s, 2H), 2.75–2.45 (m, 3H).

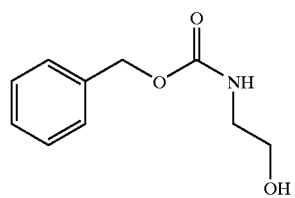

Preparation Seven

N-Benzyloxycarbonyl-2-aminoethanol. Benzylchloroformate (44.95 kg, 263.5 mol, 1.0 eq.) was added over a 2 hour period at room temperature to a solution of ethanolamine (16.1 kg, 263.5 mol, 1.0 eq.) in water (34 gal, 128.7 L). After stirring for 30 minutes, this was added to a cold (5–10° C.) solution of NaHCO₃ (33.2 kg, 395.25 mol, 1.5 eq) in H₂O (330 L) over a 30 min period and then allowed to stir at room temperature overnight. Ethyl acetate (22 gal, 83.3 L) was added, the layers separated, and the aqueous layer extracted again with ethyl acetate (22 gal., 83.3 L). The combined organic extracts were concentrated under vacuum to a volume of 10 gal (37.9 L), and the remainder displaced with isopropyl ether. The resulting slurry was stirred and cooled to 10° C. for 2 hours, then filtered. The solids were washed with isopropyl ether and vacuum dried to give the title compound (39.1 kg, 71.1%). mp 61–63° C. NMR (300 MHz, d₆-DMSO): δ=7.50–7.37 (m, 5H), 7.37–7.16 (m, 1H), 5.05 (s, 2H), 4.70–4.63 (m, 1H), 3.46–3.37 (m, 2H), 3.13–3.03 (m, 2H).

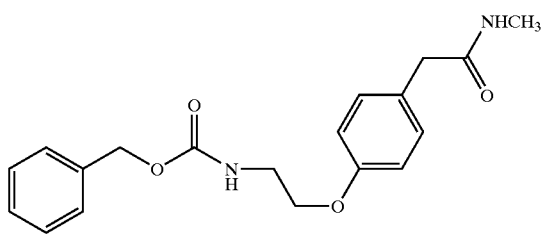

Preparation Eight

Methyl 4-(2-(N-benzyloxycarbonylamino)ethoxy) phenylacetamide. The title compound of Preparation Six (18.68 kg, 113.14 mol, 1.0 eq.) and the title compound of Preparation Seven (33.13 kg, 169.75 mol, 1.5 eq.) were dissolved in THF (40 gal, 151.4 L). Triphenylphosphine (44.5 kg, 169.75 mol, 1.5 eq.) was added and the mixture cooled to −5° C. Diisopropyl azodicarboxylate (34.3 kg, 169.75 mol, 1.5 eq.) was added over an 8 hour period, and the reaction allowed to warm to room temperature overnight. Ethyl acetate (20 gal, 75.7 L) was added to the resulting white slurry, stirring was continued for 6 hours, and the solids filtered off and dried to yield crude title compound. (29.6 kg, 76.5% of theory, mp 131–133° C.). The crude product was slurried in ethyl acetate (39.1 gal, 148 L) for 3 hours at 10° C., then filtered, washed with 10° C. ethyl acetate (14 gal, 53 L), and vacuum dried to yield the title compound(26.1 kg, 88.2% recovery, 67.5% overall). mp 134–136° C. NMR (300 MHz, d₆-DMSO): δ=7.98–7.82 (m, 1H), 7.58–7.49 (m, 1H), 7.42–7.28 (m, 5H), 7.20–7.10 (d, 2H), 6.90–6.80 (d, 2H), 5.06 (s, 2H), 4.02–3.93 (m, 2H), 3.47–3.29 (m, 4H), 2.62–2.54 (d, 3H).

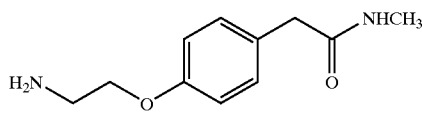

Preparation Nine

Methyl 4-(2-aminoethoxy)phenylacetamide. The title compound of Preparation Eight (18.4 kg, 53.73 mol) and 1.84 kg 10% palladium on carbon (50% water wet) were suspended in methanol (73 gal, 276.3 L) under nitrogen (N₂), and the reaction vessel pressurized to 50 psig (35.5× 10³ kg/m²) with hydrogen (H₂) gas. This H₂ pressure maintained by additional charges of H₂ until there was no further uptake of H₂ (approx. 20 hours) and the reaction was complete by tlc. After purging the vessel with N₂, the mixture was heated to 45° C. and filtered at this temperature through Celite®. The solvent was displaced with toluene until a final volume of 8 gal (30.3 L) was achieved. After cooling to 5° C., the resulting solids were filtered off, washed with cold toluene, and vacuum dried to give the title compound (9.95 kg, 88.9% of theory). NMR (300 MHz, d₆-DMSO): δ=7.99–7.57 (m, 1H), 7.20–7.10 (d, 2H), 6.90–6.80 (d, 2H), 3.93–3.83 (m, 2H), 3.30 (s, 2H), 3.00–2.62 (m, 4H), 2.57 (d, 2H).

Preparation Ten (R)-3-Benzyloxy-2-(2-tert-butoxycarbonylamino-2-methyl-propionylamino)-propionic acid. To 1.83 g (6.2 mmol) of N-t-BOC-O-benzyl-D-serine in 35 mL of DMF was added 1.02 g (7.4 mmol) of potassium carbonate followed by 0.92 g (6.5 mmol) of iodomethane. The mixture was stirred overnight at about 24° C. under an atmosphere of nitrogen. The reaction mixture was diluted with 200 mL of water, and extracted three times with ethyl acetate. The combined organics were washed five times with water and once with brine, dried over MgSO₄ and concentrated. The crude (R)-3-benzyloxy-2-tert-butoxycarbonyl-amino-propionic acid methyl ester was dissolved in 15 mL of cold trifluoroacetic acid at about 0° C. and the mixture was stirred for about 2 h. The mixture was concentrated and the residue was diluted with 1N NaOH and extracted three times with ethyl acetate. The combined organic extracts were washed with brine and dried over Na₂SO₄ to give 0.84 g (4.02 mmol) of the resulting (R)-2-amino-3-benzyloxy-propionic acid methyl ester which was coupled to 0.81 g (4.02 mmol) of N-t-BOC-α-c-methylalanine to give 1.80 g of (R)-3-benzyloxy-2-(2-tert-butoxycarbonylamino-2-methyl-propionylamino)-propionic acid methyl ester. The crude product was dissolved in 20 mL of 4:1 THF:water and a solution of 335 mg (7.98 mmol) of lithium hydroxide hydrate in 1 mL of water was added to the solution and the mixture was stirred overnight at room temperature. The mixture was concentrated and the residue was diluted with ethyl acetate and acidified with aqueous HCl and extracted three times with ethyl acetate. The organic extracts were combined and washed once with brine, dried over Na₂SO₄ and concentrated to give 1.60 g of the title compound as an oil which solidified on standing. ¹H NMR (CDCl₃ 300 MHz) δ 7.30 (m, 5H), 7.10 (d, 1H), 5.07 (bs, 1H), 4.68 (m, 1H), 4.53 (q, 2H), 4.09 (m, 1H), 3.68 (m, 1H), 1.3–1.5 (m, 15H).

Preparation Eleven

4-Oxo-piperidine-1,3-dicarboxylic acid 1-tert-butyl ester 3-methyl ester. To a mixture of 7.00 g (36.2 mmol) of 4-oxo-piperidine-3-carboxylic acid methyl ester and 8.82 g (72.3 mmol) of 4,4-dimethylaminopyridine in 200 mL of methylene chloride at about 0° C. was added a solution of 7.88 g (36.2 mmol) of di-tert-butyldicarbonate in 150 mL of methylene chloride over about 30 min. The mixture was warmed to room temperature and then stirred for about 17 h. The mixture was concentrated and the residue was diluted with chloroform and washed three times each with 10% aqueous HCl, saturated aqueous sodium bicarbonate solution and brine, dried over MgSO₄ and concentrated to give 9.18 g of a clear yellow oil.

Preparation Twelve 3-(R,S)-Benzyl-4-oxo-piperidine-1,3-dicarboxylic acid 1-tert-butyl ester 3-methyl ester. To a solution of 5.00 g (19.4 mmol) the compound of Preparation Eleven in 10 mL of DMF was added 745 mg (7.4 mmol) of sodium hydride (60% oil dispersion) and the mixture was stirred at room temperature for about 15 min. A solution of 3.32 g (19.4 mmol) benzylbromide in 15 mL of DMF was added to the stirring solution by cannula and the mixture was stirred for about 42 h at room temperature. The mixture was diluted with ethyl acetate and over $MgSO_4$, and concentrated to give 6.0 g of the title compound as a yellow oil. MS (Cl, $NH_3$) 348 (washed once with water and four times with brine, dried MH+).

Preparation Thirteen 3a-(R,S)-Benzyl-2-methyl-3-oxo-2,3,3a,4,6,7-hexahydro-pyrazolo[4,3-c]-pyridine-5-carboxylic acid tert-butyl ester. A mixture of 4.00 g (11.5 mmol) of the title compound of Preparation Twelve and 530 mg (11.5 mmol) of methylhydrazine in 100 mL of ethanol was heated at reflux for about 8 h. The mixture was concentrated and the residue was dissolved in 100 mL toluene and heated at reflux for about 17 h. The mixture was concentrated and the residue was purified by silica gel chromatography sing an elution gradient of (15:85 v/v ethyl acetate:hexane) to (75:25 v/v ethyl acetate:hexane) to give 2.6 g of the title compound as a clear colorless oil. MS (Cl, $NH_3$) 344 (MH+).

Preparation Fourteen 2-tert-Butoxycarbonylamino-2-methyl-propionic acid 2,5-dioxo-pyrrolidin-1-yl ester. A stirred solution of N-hydroxysuccinimide (112 g, 0.973 mol), N-t-butoxycarbonyl-α-methylalanine (197 g, 0.969 mol), and 1-(3-dimethylaminopropyl)-3-ethylcarbodiimide (186 g, 0.970 mol) in anhydrous dichloromethane (1.4 L) was stirred at room temperature for about 18 hours under nitrogen atmosphere. The reaction mixture was washed three times each with saturated sodium bicarbonate solution and then brine. The organic layer was dried over sodium sulfate, filtered and concentrated in vacuo to give the title compound as a white solid (256 g, 88%): PBMS (M+18)+ 318; $^1$H NMR=250 MHz ($CDCl_3$) δ: 4.91 (NH, br s, 1H), 2.84 (—CO($CH_2$)$_2$CO—, s, 4H), 1.67 (Me, s, 6H), 1.48 (BOC, s, 9H).

Preparation Fifteen

3-Benzyloxy-2-(2-tert-butoxycarbonylamino-2-methyl-propionylamino)-propionic acid. To a solution of D-O-benzylserine (106 g, 0.532 mol) and the title compound of Preparation Fourteen (160 g, 0.532 mol) in water/dioxane (250/1000 mL) was slowly added triethylamine (223 mL, 1.60 mol) at room temperature. The reaction was heated to about 50° C. and stirred for about 15 hours under nitrogen atmosphere. The solvent was then removed in vacuo, ethyl acetate was added, and the stirred mixture was acidified with 10% aqueous HCl solution to pH 2–3. The organic layer was dried over sodium sulfate, filtered and concentrated in vacuo to give the title compound (200 g, 99%): -APCI MS (M-1)- 379; $^1$H NMR=300 MHz (methanol-$d_4$) δ: 7.69 (NH, d, 1H), 7.32 (Ph, m, 5H), 4.60 —(CHCO$_2$H, m, 1H), 4.51 —(CH:Ph, s, 2H), 3.81 (CHOBz, m, 2H), 1.41 (Me, s, 6H), 1.40 (BOC, s, 9H).

While the foregoing specification discloses the principles of the present invention, with examples provided for the purpose of illustration, it will be understood that the practice of the invention encompasses all of the usual variations, adaptations or modifications as come within the scope of the following claims and its equivalents.

What is claimed is:

1. A method for treating non-insulin dependent diabetes mellitus in a mammal comprising administering to said mammal a $β_3$ adrenergic agonist and a growth hormone secretagogue for a time and under conditions effective to ameliorate said diabetes mellitus, wherein said $β_3$ adrenergic agonist is a compound of formula I:

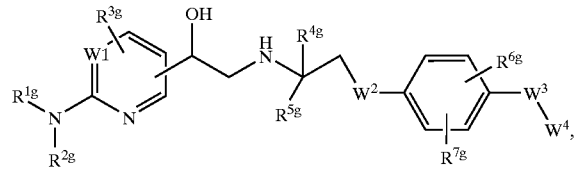

wherein:
$R^{1g}$, $R^{2g}$, $R^{4g}$ and $R^{5g}$ are independently hydrogen or $(C_1–C_6)$alkyl;

$R^{3g}$, $R^{6g}$ and $R^{7g}$ are independently hydrogen, halogen, $(C_1–C_6)$alkyl, nitro, cyano, trifluoromethyl, $SO_2R^{8g}$, $SO_2NR^{9g}R^{10g}$, $NR^{9g}R^{10g}$, $COR^{11g}$, $CO_2R^{9g}$, $(C_1–C_6)$ alkoxy, $NR^{9g}SO_2R^{8g}$, $NR^{9g}COR^{11g}$, $NR^{9g}CO_2R^{9g}$ or $OR^{9g}$;

$R^{8g}$ is independently $(C_1–C_6)$alkyl or $(C_1–C_6)$alkoxy $(C_1–C_6)$alkyl;

$R^{9g}$ and $R^{10g}$ are independently hydrogen, $(C_1–C_6)$alkyl, cycloalkyl($C_3–C_8$), or $(C_1–C_6)$alkoxy($C_1–C_6$)alkyl;

$R^{11g}$ is independently hydrogen, $(C_1–C_6)$alkyl, $NR^{9g}R^{10g}$, $(C_3–C_8)$cycloalkyl, or $(C_1–C_6)$alkoxy($C_1–C_6$)alkyl;

$W^1$ is N, CH, or, when $R^{3g}$ is bonded to $W^1$, $CR^{3g}$ wherein $R^{3g}$ can be any of the values listed above for $R^{3g}$ in addition to H;

$W^2$ and $W^3$ are independently a direct link, oxygen, sulfur, or $NR^{1g}$ wherein $R^{1g}$ is as defined above;

$W^4$ is $(CH_2)_yOR^{9g}$, $(CH_2)_zCO_2 R^{11g}$, $(CH_2)_zCOR^{11g}$, $(CH_2)_zSO_2NR^{9g}R^{10g}$, $(CH_2)_z$—$NR^{9g}SO_2R^{8g}$, $(CH_2)_zP(O)(OR^{1g})(OR^{2g})$, $(CH_2)_z$—O—$(CH_2)_yCO_2R^{11g}$, $(CH_2)_n$—O—$(CH_2)_yCOR^{11g}$, $(CH_2)_z$—O—$(CH_2)_yP(O)(OR^{1g})(OR^{2g})$, $(CH_2)_z$—O—$(CH_2)_ySO_2NR^{9g}R^{10g}$, or $(CH_2)_z$—O—$(CH_2)_y$—$NR^{9g}SO_2R^{8g}$;

wherein $R^{1g}$, $R^{2g}$, $R^{8g}$, $R^{9g}$, $R^{10g}$, and $R^{11g}$ are as defined above;

y is 1 to 6;

z is 0 to 6, provided that if Y is O or S, z is not 0;

a pharmaceutically acceptable prodrug of said compounds; or a pharmaceutically acceptable salt of said compounds and said prodrugs;

and further wherein said growth hormone secretagogue is a compound of the Formula IV:

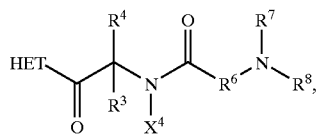

or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug, wherein:

HET is a heterocyclic moiety selected from the group consisting of

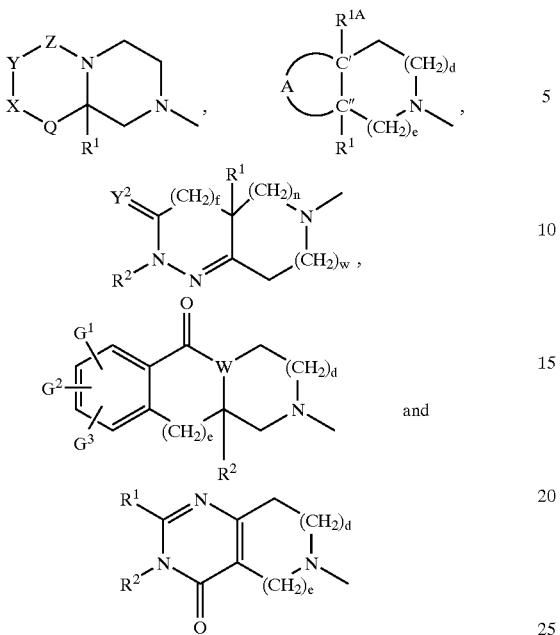

d is 0, 1 or 2;
e is 1 or 2;
f is 0 or 1;
n and w are 0, 1 or 2, provided that n and w cannot both be 0 at the same time;
$y^2$ is oxygen or sulfur;
A is a divalent radical, where the left hand side of the radical as shown below is connected to C" and the right hand side of the radical as shown below is connected to C', selected from the group consisting of
—$NR^2$—C(O)—$NR^2$—, —$NR^2$—S(O)$_2$—$NR^2$—, —O—C(O)—$NR^2$—, —$NR^2$—C(O)—O—, —C(O)—$NR^2$—C(O)—, —C(O)—$NR^2$—C($R^9R^{10}$)—, —C($R^9R^{10}$)—$NR^2$—C(O)—, —C($R^9R^{10}$)—C($R^9R^{10}$)—C($R^9R^{10}$)—, —S(O)$_2$—C($R^9R^{10}$)—C($R^9R^{10}$)—, —C($R^9R^{10}$)—O—C(O)—, —C($R^9R^{10}$)—O—C($R^9R^{10}$)—, —$NR^2$—C(O)—C($R^9R^{10}$)—, —O—C(O)—C($R^9R^{10}$)—, —C($R^9R^{10}$)—C(O)—$NR^2$—, —C(O)—$NR^2$—C(O)—, —C($R^9R^{10}$)—C(O)—O—, —C(O)—$NR^2$—C($R^9R^{10}$)—C($R^9R^{10}$)—, —C(O)—O—C($R^9R^{10}$)—, —C($R^9R^{10}$)—C($R^9R^{10}$)—C($R^9R^{10}$)—C($R^9R^{10}$)—, —S(O)$_2$—$NR^2$—C($R^9R^{10}$)—C($R^9R^{10}$)—, —C($R^9R^{10}$)—C($R^9R^{10}$)—$NR^2$—C(O)—, —C($R^9R^{10}$)—C($R^9R^{10}$)—O—C(O)—, —$NR^2$—C(O)—C($R^9R^{10}$)—C($R^9R^{10}$)—, —$NR^2$—S(O)$_2$—C($R^9R^{10}$)—C($R^9R^{10}$)—, —O—C(O)—C($R^9R^{10}$)—C($R^9R^{10}$)—, —C($R^9R^{10}$)—C($R^9R^{10}$)—C(O)—$NR^2$—, —C($R^9R^{10}$)—C($R^9R^{10}$)—C(O)—, —C($R^9R^{10}$)—$NR^2$—C(O)—O—, —C($R^9R^{10}$)—O—C(O)—$NR^2$—, —$NR^2$—C(O)—O—C($R^9R^{10}$)—, —$NR^2$—C(O)—$NR^2$—C($R^9R^{10}$)—, —$NR^2$—S(O)$_2$—$NR^2$—C($R^9R^{10}$)—, —O—C(O)—$NR^2$—C($R^9R^{10}$)—, —C(O)—N=C($R^{11}$)—$NR^2$—, —C(O)—$NR^2$—C($R^{11}$)=N—, —C($R^9R^{10}$)—$NR^{12}$—C($R^9R^{10}$)—, —$NR^{12}$—C($R^9R^{10}$)—, —$NR^{12}$—C($R^9R^{10}$)—C($R^9R^{10}$)—, —C(O)—O—C($R^9R^{10}$)—C($R^9R^{10}$)—, —$NR^2$—C($R^{11}$)=N—C(O)—, —C($R^9R^{10}$)—C($R^9R^{10}$)—N($R^{12}$)—, —C($R^9R^{10}$)—$NR^{12}$—, —N=C($R^{11}$)—$NR^2$—C(O)—, —C($R^9R^{10}$)—C($R^9R^{10}$)—$NR^2$—S(O)$_2$—, —C($R^9R^{10}$)—C($R^9R^{10}$)—S(O)$_2$—$NR^2$—, —C($R^9R^{10}$)—C($R^9R^{10}$)—C(O)—O—, —C($R^9R^{10}$)—S(O)$_2$—C($R^9R^{10}$)—, —C($R^9R^{10}$)—C($R^9R^{10}$)—S(O)$_2$—, —O—C($R^9R^{10}$)—C($R^9R^{10}$)—, —C($R^9R^{10}$)—C($R^9R^{10}$)—O—, —C(O)—C($R^9R^{10}$)—C($R^9R^{10}$)— and —C($R^9R^{10}$)—$NR^2$—S(O)$_2$—$NR^2$—;

Q is a covalent bond or $CH_2$;
W is CH or N;
X is $CR^9R^{10}$, C=$CH_2$ or C=O;
Y is $CR^9R^{10}$, O or $NR^2$;
Z is C=O, C=S or S(O)$_2$;
$G^1$ is hydrogen, halo, hydroxy, nitro, amino, cyano, phenyl, carboxyl, —$CONH_2$, —$C_1$-$C_4$)alkyl optionally substituted with one or more phenyl, one or more halogens or one or more hydroxy groups, —($C_1$-$C_4$)alkoxy optionally independently substituted with one or more phenyl, one or more halogens or one or more hydroxy groups, —($C_1$-$C_4$)alkylthio, phenoxy, —COO($C_1$-$C_4$)alkyl, N,N-di-($C_1$-$C_4$)alkylamino, —($C_2$-$C_6$)alkenyl optionally independently substituted with one or more phenyl, one or more halogens or one or more hydroxy groups, —($C_2$-$C_6$)alkynyl optionally independently substituted with one or more phenyl, one or more halogens or one or more hydroxy groups, —($C_3$-$C_6$)cycloalkyl optionally independently substituted with one or more ($C_1$-$C_4$)alkyl groups, one or more halogens or one or more hydroxy groups, —($C_1$-$C_4$)alkylamino carbonyl or di-($C_1$-$C_4$) alkylamino carbonyl;
$G^2$ and $G^3$ are each independently selected from the group consisting of hydrogen, halo, hydroxy, —($C_1$-$C_4$)alkyl optionally independently substituted with one to three halo groups and —($C_1$-$C_4$)alkoxy optionally independently substituted with one to three halo groups;
$R^1$ is hydrogen, —CN, —$(CH_2)_qN(X^6)C(O)X^6$, —$(CH_2)_qN(X^6)C(O)(CH_2)_t$—$A^1$, —$(CH_2)_qN(X^6)S(O)_2(CH_2)_t$—$A^1$, —$(CH_2)_qN(X^6)S(O)_2X^6$, —$(CH_2)_q N)C(O)N(X^6)(CH_2)_t$—$A^1$, —$(CH_2)_qN(X^6)C(O)N(X^6)(X^6)$, —$(CH_2)_qC(O)N(X^6)(X^6)$, —$(CH_2)_qC(O)N(X^6)(CH_2)_t$—$A^1$, —$(CH_2)_qC(O)$ $OX^6$, —$(CH_2)_qC(O)O(CH_2)_t$—$A^1$, —$(CH_2)_qOX^6$, —$(CH_2)_qOC(O)X^6$, —$(CH_2)_qOC(O)(CH_2)_t$—$A^1$, —$(CH_2)_qOC(O)N(X^6)(CH_2)_t$—$A^1$, —$(CH_2)_qOC(O)$ $N(X^6)(X^6)$, —$(CH_2)_qC(O)X^6$, —$(CH_2)_qC(O)$ $CH_2)_t$—$A^1$, —$(CH_2)_qN(X^6)C(O)OX^6$, —$(CH_2)_qN$ $(X^6)S(O)_2N(X^6)(X^6)$, —$(CH_2)_qS(O)_mX^6$, —$(CH_2)_q$ $S(O)_m(CH_2)_t$—$A^1$, —($C_1$-$C_{10}$)alkyl, —$(CH_2)_t$—$A^1$, —$(CH_2)_q$—($C_3$-$C_7$)cycloalkyl, —$(CH_2)_q$—$Y^1$— ($C_1$-$C_6$)alkyl, —$(CH_2)_q$—$Y^1$—$(CH_2)_t$—$A^1$ or —$(CH_2)_q$—$Y^1$—$(CH_2)_t$—($C_3$-$C_7$)cycloalkyl;
where the alkyl and cycloalkyl groups in the definition of $R^1$ are optionally substituted with ($C_1$-$C_4$) alkyl, hydroxy, ($C_1$-$C_4$)alkoxy, carboxyl, —$CONH_2$, —S(O)$_m$($C_1$-$C_6$)alkyl, —$CO_2$($C_1$-$C_4$) alkyl ester, 1H-tetrazol-5-yl or 1, 2 or 3 fluoro groups;
$Y^1$ is O, S(O)$_m$, —C(O)$NX^6$—, —CH=CH—, —C≡C—, —N($X^6$)C(O)—, —C(O)$NX^6$—, —C(O)O—, —OC(O)N($X^6$)— or —OC(O)—;

q is 0, 1, 2, 3 or 4;

t is 0, 1, 2 or 3;

said —$(CH_2)_q$ group and $(CH_2)_t$ group in the definition of $R^1$ are optionally independently substituted with hydroxy, $(C_1-C_4)$alkoxy, carboxyl, —$CONH_2$, —$S(O)_m(C_1-C_6)$alkyl, —$CO_2(C_1-C_4)$ alkyl ester, 1H-tetrazol-5-yl, 1, 2 or 3 fluoro groups or 1 or 2 $(C_1-C_4)$alkyl groups;

$R^{1A}$ is selected from the group consisting of hydrogen, F, Cl, Br, I, $(C_1-C_6)$alkyl, phenyl$(C_1-C_3)$alkyl, pyridyl$(C_1-C_3)$alkyl, thiaolyl$(C_1-C_3)$alkyl and thienyl$(C_1-C_3)$alkyl, provided that $R^{1A}$ is not F, Cl, Br or I when a heteroatom is vicinal to C";

$R^2$ is hydrogen, $(C_1-C_8)$alkyl, —$(C_0-C_3)$alkyl-$(C_3-C_8)$ cycloalkyl, —$(C_1-C_4)$alkyl-$A^1$ or $A^1$;

where the alkyl groups and the cycloalkyl groups in the definition of $R^2$ are optionally substituted with hydroxy, —$C(O)OX^6$, —$C(O)N(X^6)(X^6)$, —$N(X^6)(X^6)$, —$S(O)_m(C_1-C_6)$alkyl, —$C(O)A^1$, —$C(O)(X^6)$, $CF_3$, CN or 1, 2 or 3 independently selected halo groups;

$R^3$ is selected from the group consisting of $A^1$, $(C_1-C_{10})$alkyl, —$(C_1-C_6)$alkyl-$A^1$, —$(C_1-C_6)$alkyl-$(C_3-C_7)$cycloalkyl, —$(C_1-C_5)$alkyl-$X^1$—$(C_1-C_5)$alkyl, —$(C_1-C_5)$alkyl-$X^1$—$(C_0-C_5)$alkyl-$A^1$ and —$(C_1-C_5)$alkyl-$X^1$—$(C_1-C_5)$alkyl-$(C_3-C_7)$ cycloalkyl;

where the alkyl groups in the definition of $R^3$ are optionally substituted with —$S(O)_m(C_1-C_6)$alkyl, —$C(O)OX^3$, 1, 2, 3, 4 or 5 independently selected halo groups or 1, 2 or 3 independently selected —$OX^3$ groups;

$X^1$ is O, $S(O)_m$, —$N(X^2)C(O)$—, —$C(O)N(X^2)$—, —$OC(O)$—, —$C(O)O$—, —$CX^2$=$CX^2$—, —$N(X^2)C(O)O$—, —$OC(O)N(X^2)$— or —C≡C—;

$R^4$ is hydrogen, $(C_1-C_6)$alkyl or $(C_3-C_7)$cycloalkyl, or $R^4$ is taken together with $R^3$ and the carbon atom to which they are attached and form $(C_5-C_7)$cycloalkyl, $(C_5-C_7)$cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;

$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;

$R^6$ is a bond or is

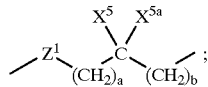

where a and b are each independently 0, 1, 2 or 3;

$X^5$ and $X^{5a}$ each independently selected from the group consisting of hydrogen, $CF_3$, $A^1$ and optionally substituted $(C_1-C_6)$alkyl;

the optionally substituted $(C_1-C_6)$alkyl in the definition of $X^5$ and $X^{5a}$ is optionally substituted with a substituent selected from the group consisting of $A^1$, $OX^2$, —$S(O)_m(C_1-C_6)$ alkyl, —$C(O)OX^2$, $(C_3-C_7)$cycloalkyl, —$N(X^2)(X^2)$ and —$C(O)N(X^2)(X^2)$;

or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then only one of $X^5$ or $X^{5a}$ is on the carbon atom and only one of $R^7$ or $R^8$ is on the nitrogen atom and further provided that when two alkylene bridges are formed then $X^5$ and $X^{5a}$ cannot be on the carbon atom and $R^7$ and $R^8$ cannot be on the nitrogen atom;

or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;

or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$Z^1$ is a bond, O or N—$X^2$, provided that when a and b are both 0 then $Z^1$ is not N—$X^2$ or O;

$R^7$ and $R^8$ are each independently hydrogen or optionally substituted $(C_{1-6})$alkyl;

where the optionally substituted $(C_1-C_6)$alkyl in the definition of $R^7$ and $R^8$ is optionally independently substituted with $A^1$, —$C(O)O$—$(C_1-C_6)$ alkyl, —$S(O)_m(C_1-C_6)$alkyl, 1 to 5 halo groups, 1 to 3 hydroxy groups, 1 to 3 —O—$C(O)(C_1-C_{10})$ alkyl groups or 1 to 3 $(C_1-C_6)$alkoxy groups; or $R^7$ and $R^8$ can be taken together to form —$(CH_2)_r$—L—$(CH_2)_r$—;

where L is $C(X^2)(X^2)$, $S(O)_m$ or $N(X^2)$;

$R^9$ and $R^{10}$ are each independently selected from the group consisting of hydrogen, fluoro, hydroxy and $(C_1-C_5)$alkyl optionally independently substituted with 1–5 halo groups;

$R^{11}$ is selected from the group consisting of $(C_1-C_5)$alkyl and phenyl optionally substituted with 1–3 substitutents each independently selected from the group consisting of $(C_1-C_5)$alkyl, halo and $(C_1-C_5)$alkoxy;

$R^{12}$ is selected from the group consisting of $(C_1-C_5)$ alkylsulfonyl, $(C_1-C_5)$alkanoyl and $(C_1-C_5)$alkyl where the alkyl portion is optionally independently substituted by 1–5 halo groups; $A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, on one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —$OX^6$, —$C(O)N(X^6)(X^6)$, —$C(O)OX^6$, oxo, $(C_1-C_6)$alkyl, nitro, cyano, benzyl, —$S(O)_m(C_1-C_6)$alkyl, 1H-tetrazol-5-yl, phenyl, phenoxy, phenylalkyloxy, halophenyl, methylenedioxy, —$N(X^6)(X^6)$, —$N(X^6)C(O)(X^6)$, —$S(O)_2N(X^6)(X^6)$, —$N(X^6)S(O)_2$-phenyl, —$N(X^6)S(O)_2X^6$, —$CONX^{11}X^{12}$, —$S(O)_2NX^{11}X^{12}$, —$NX^6S(O)_2X^{12}$, —$NX^6CONX^{11}X^{12}$, —$NX^6S(O)_2NX^{11}X^{12}$, —$NX^6C(O)X^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted $(C_1-C_6)$alkyl;

the optionally substituted $(C_1-C_6)$alkyl defined for $X^{11}$ is optionally independently substituted with phenyl, phenoxy, $(C_1-C_6)$alkoxycarbonyl, —$S(O)_m(C_1-C_6)$alkyl, 1 to 5 halo groups, 1 to 3 hydroxy groups, 1 to 3 $(C_1-C_{10})$alkanoyloxy groups or 1 to 3 $(C_1-C_6)$alkoxy groups;

$X^{12}$ is hydrogen, $(C_1-C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, $CH_3$, $OCH_3$, $OCF_3$ and $CF_3$;

or $X^{11}$ and $X^{12}$ are taken together to form —$(CH_2)_r$—$L^1$—$(CH_2)_r$—;

$L^1$ is $C(X^2)(X^2)$, O, $S(O)_m$ or $N(X^2)$;

r for each occurrence is independently 1, 2 or 3;

$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with —$S(O)_m(C_1-C_6)$alkyl, —$C(O)OX^3$, 1 to 5 halo groups or 1–3 $OX^3$ groups;

$X^3$ for each occurrence is independently hydrogen or $(C_1-C_6)$alkyl;

$X^6$ for each occurrence is independently hydrogen, optionally substituted $(C_1-C_6)$alkyl, $(C_2-C_6)$halogenated alkyl, optionally substituted $(C_3-C_7)$cycloalkyl, $(C_3-C_7)$-halogenated cycloalkyl, where optionally substituted $(C_1-C_6)$alkyl and optionally substituted $(C_3-C_7)$cycloalkyl in the definition of $X^6$ is optionally independently mono- or di-substituted with $(C_1-C_4)$alkyl, hydroxy, $(C_1-C_4)$alkoxy, carboxyl, $CONH_2$, —$S(O)_m(C_1-C_6)$alkyl, carboxylate $(C_1-C_4)$alkyl ester or 1H-tetrazol-5-yl; or when there are two $X^6$ groups on one atom and both $X^6$ are independently $(C_1-C_6)$alkyl, the two $(C_1-C_6)$ alkyl groups may be optionally joined and, together with the atom to which the two $X^6$ groups are attached, form a 4- to 9-membered ring optionally having oxygen, sulfur or $X^7$ as a ring member;

$X^7$ is hydrogen or $(C_1-C_6)$alkyl optionally substituted with hydroxy;

m for each occurrence is independently 0, 1 or 2;

with the proviso that:

$X^6$ and $X^{12}$ cannot be hydrogen when attached to $C(O)$ or $S(O)_2$ in the form $C(O)X^6$, $C(O)X^{12}$, $S(O)_2X^6$ or $S(O)_2X^{12}$; and when $R^6$ is a bond then L is $N(X^2)$ and each r in the definition —$(CH_2)_r$—L—$(CH_2)_r$— is independently 2 or 3.

2. A method of claim 1 wherein said $\beta_3$ adrenergic agonist is (4-(2-(2-(6-aminopyridin-3-yl)-2(R)-hydroxyethylamino) ethoxy)phenyl)acetic acid, a prodrug thereof or a pharmaceutically acceptable salt of said $\beta_3$ adrenergic agonist or said prodrug.

3. A method of claim 1 wherein said growth hormone secretagogue is 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide, a prodrug thereof or a pharmaceutically acceptable salt of said growth hormone secretagogue or said prodrug.

4. A method of claim 1 wherein said growth hormone secretagogue is 2-amino-N-(1-(R)-(2,4-difluoro-benzyloxymethyl)-2-oxo-2-(3-oxo-3a-(R)-pyridin-2-ylmethyl)-2-(2,2,2-trifluoro-ethyl)-2,3,3a,4,6,7-hexahydro-pyrazolo-[4,3-c]pyridin-5-yl)-ethyl)-2-methyl-propionamide, a prodrug thereof or a pharmaceutically acceptable salt of said growth hormone secretagogue or said prodrug.

5. A method of claim 1 wherein said growth hormone secretagogue is 2-amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide, a prodrug thereof or a pharmaceutically acceptable salt of said growth hormone secretagogue or said prodrug.

* * * * *